(12) United States Patent
Hamprecht et al.

(10) Patent No.: US 6,472,349 B1
(45) Date of Patent: Oct. 29, 2002

(54) PYRIDINE-2,3-DICARBOXYLIC ACID DIAMIDES

(75) Inventors: Gerhard Hamprecht, Weinheim; Markus Menges, Harthausen; Olaf Menke, Altleiningen; Robert Reinhard, Ludwigshafen; Ingo Sagasser, Eppelheim; Cyrill Zagar, Ludwigshafen; Karl-Otto Westphalen, Speyer; Martina Otten, Ludwigshafen; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/937,843
(22) PCT Filed: Mar. 31, 2000
(86) PCT No.: PCT/EP00/02899
§ 371 (c)(1), (2), (4) Date: Sep. 28, 2001
(87) PCT Pub. No.: WO00/58288
PCT Pub. Date: Oct. 5, 2000

(30) Foreign Application Priority Data

Mar. 31, 1999 (DE) .......................................... 199 14 721

(51) Int. Cl.$^7$ ....................... C07D 213/81; A01N 43/40
(52) U.S. Cl. ....................... 504/130; 546/336; 546/337
(58) Field of Search ........................... 546/336, 337; 514/357; 504/130

(56) References Cited

FOREIGN PATENT DOCUMENTS

EP             799825        * 10/1997

* cited by examiner

*Primary Examiner*—Zinna Northington Davis
(74) *Attorney, Agent, or Firm*—Keil & Weinkauf

(57) ABSTRACT

Pyridine-2,3-dicarboxamides of the formula I

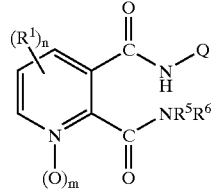

in which the variables are as defined in the description, which are suitable for use as herbicides or for the desiccation or defoliation of plants are described.

20 Claims, No Drawings

PYRIDINE-2,3-DICARBOXYLIC ACID DIAMIDES

The application is a 371 of PCT/EP 00/02899, Mar. 31, 2000.

The present invention relates to pyridine-2,3-dicarboxamides of the formula I

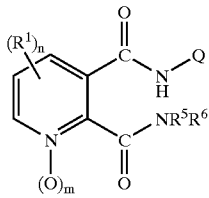

where:

$R^1$ is halogen, CN, $NO_2$, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl, $C_1$–$C_3$-haloalkylsulfonyl, $C_3$–$C_6$-cycloalkyl, $C_3$–$C_6$-cycloalkyl-$C_1$–$C_3$-alkyl, $C_2$–$C_4$-alkenyl, $C2$–$C_4$-haloalkenyl, $C_2$–$C_4$-alkynyl, $C_3$–$C_4$-haloalkynyl, amino, $C_1$–$C_3$-monoalkylamino or $C_1$–$C_3$-alkylcarbonyl;

Q is one of the radicals $Q_1$–$Q_7$ $Q_1$

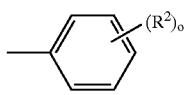

$Q_2$

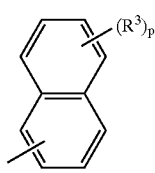

$Q_3$

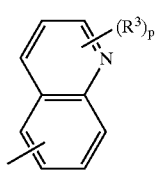

$Q_4$

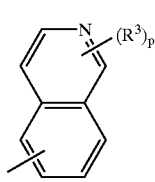

$Q_5$

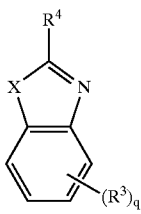

$Q_6$

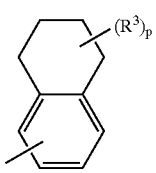

$Q_7$

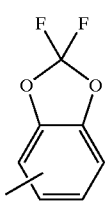

$R^2$ is halogen, CN, $NO_2$, formyl, carbamoyl, $C_1$–$C_4$-alkylcarbonyl, $C_1$–$C_3$-alkoximinomethyl, $C_1$–$C_3$-alkyl, $C_1$–$C_3$-haloalkyl, $C_1$–$C_3$-alkoxymethyl, $C_1$–$C_3$-alkoxy, $C_1$–$C_3$-haloalkoxy, $C_1$–$C_3$-alkoxycarbonyl, $C_1$–$C_3$-alkylthiocarbonyl, $C_1$–$C_3$-alkylcarbamoyl or $C_1$–$C_3$-alkoxycarbonyl-$C_1$–$C_3$-alkoxy, $C_3$–$C_4$-alkenyloxy, $C_3$–$C_4$-haloalkenyloxy, $C_3$–$C_4$-alkynyloxy, $C_3$–$C_4$-haloalkenyloxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl or $C_1$–$C_3$-haloalkylsulfonyl;

$R^3$ is halogen, CN, $NO_2$, $C_1$–$C_3$-alkyl, $C_1$–$C_3$-alkoxy, $C_1$–$C_3$-haloalkyl or $C_1$–$C_3$-haloalkoxy;

$R^4$ is hydrogen, $C_1$–$C_3$-alkyl, $C_1$–$C_3$-haloalkyl, $C_1$–$C_3$-alkoxy, saturated or unsaturated $C_3$–$C_7$-cycloalkyl, 3- to 7-membered saturated or unsaturated heterocyclyl having 1, 2 or 3 heteroatoms selected independently of one another from the group consisting of N, O and S, where each cycloalkyl and/or heterocyclyl ring may be unsubstituted or have 1 or 2 substituents selected independently of one another from the group consisting of halogen, $C_1$–$C_3$-alkyl, $C_1$–$C_3$-haloalkyl or $C_1$–$C_3$-alkoxy;

$R^5$ is hydrogen, $C_1$–$C_3$-alkyl, OH or $C_1$–$C_4$-alkoxy;

$R^6$ is hydrogen, $C_1$–$C_6$-alkyl, $C_1$–$C_6$-haloalkyl, $C_1$–$C_6$-cyanoalkyl, $C_3$–$C_6$-cycloalkyl, $C_3$–$C_6$-cycloalkenyl, $C_3$–$C_6$-cycloalkyl-$C_1$–$C_3$-alkyl, $C_3$–$C_6$-cycloalkyl having 1 or 2 substituents which are selected independently of one another from the group consisting of halogen and $C_1$–$C_3$-alkyl, is $C_3$–$C_6$-cycloalkoxy-$C_1$–$C_3$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkoxycarbonyl-$C_1$–$C_6$-alkyl, $C_3$–$C_6$-alkenyl, $C_3$–$C_6$-alkynyl, amino, $C_1$–$C_4$-monoalkylamino, di-$C_1$–$C_4$-alkylamino or $R^6$ together with $R^5$ is a 5- or 6-membered heterocycle having 1, 2 or 3 heteroatoms which are selected independently of one another from the group consisting of N, O and S, and which is unsubstituted or has 1 or 2 substituents selected independently of one another from the group consisting of halogen, $C_1$–$C_3$-alkyl, $C_1$–$C_3$-alkoxy and $C_1$–$C_3$-haloalkyl;

X is O or S;

m is 0 or 1;

n is 0, 1, 2 or 3;

o is 0, 1, 2, 3, 4 or 5;

p is 0, 1, 2, 3 or 4;

q is 0, 1, 2 or 3, where n is 2 or 3 if Q is $Q_1$, and salts thereof, in particular to the agriculturally useful salts of the compounds of the formula I.

Moreover, the invention relates to the use of the compounds I as herbicides, herbicidal compositions comprising the compounds I as active substances, methods for controlling undesirable plant growth using the compounds I.

EP 799 825 A describes certain pyridine-2,3-dicarboxamides for use as herbicides.

It is an object of the present invention to provide novel herbicidally active pyridine-2,3-dicarboxamides which allow better selective control of undesirable plants than the known pyridine-2,3-dicarboxamides.

We have found that this object is achieved by the above-mentioned pyridine-2,3-dicarboxamides of the formula I.

Furthermore, we have found herbicidal compositions which comprise these compounds and have very good herbicidal activity. Moreover, we have found methods for controlling undesirable vegetation using the compounds I.

Depending on the substitution pattern, the compounds of the formula I can contain one or more chiral centers, in which case they exist in the form of enantiomers or diastereomer mixtures. The invention provides both the pure enantiomers and diastereomers and mixtures thereof.

Suitable agriculturally useful salts are, in particular, the acid addition salts with those acids whose anions do not adversely affect the herbicidal activity of the compounds of the formula I.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate. They can be formed by reacting the compounds of the formula I with an acid of the appropriate anion, preferably hydrochloric acid, hydrobromic acid, sulfuric acid, phosphoric acid or nitric acid.

The organic molecular moieties mentioned in the definition of the substituents $R^1$ to $R^6$ or as radicals on saturated cycloalkyl or saturated heterocyclic rings are—like the term halogen—collective terms for individual listings of the individual group members. All hydrocarbon chains, i.e. all alkyl, alkenyl, alkynyl, haloalkyl, haloalkenyl, haloalkynyl, cyanoalkyl, aminoalkyl, alkoxy, haloalkoxy, alkylthio, haloalkylthio, alkylsulfinyl, haloalkylsulfinyl, alkylsulfonyl, haloalkylsulfonyl, alkoxycarbonyl and alkoxycarbonylalkoxy radicals, etc., can be straight-chain or branched. Halogenated substituents preferably carry 1, 2, 3, 4 or 5 identical or different halogen atoms. The term halogen represents in each case fluorine, chlorine, bromine and iodone, preferably fluorine and chlorine.

Examples of particular meanings are:

$C_1$–$C_3$-alkyl: methyl, ethyl, n-propyl, 1-methylethyl;

$C_1$–$C_4$-alkyl: $C_1$–$C_3$-alkyl as mentioned above, and also n-butyl, 1-methylpropyl, 2-methylpropyl and 1,1-dimethylethyl;

$C_1$–$C_6$-alkyl: $C_1$–$C_4$-alkyl as mentioned above, and also n-pentyl, 1-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

($C_1$–$C_3$-alkyl)carbonyl: methylcarbonyl, ethylcarbonyl, n-propylcarbonyl, 1-methylethylcarbonyl; in particular methylcarbonyl, ethylcarbonyl or 1-methylethylcarbonyl;

$C_2$–$C_4$-alkenyl: eth-1-en-1-yl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl;

$C_3$–$C_6$-alkenyl: $C_3$–$C_4$-alkenyl as mentioned above, n-penten-1-yl, n-penten-2-yl, n-penten-3-yl, n-penten-4-yl, 1-methylbut-1-en-1-yl, 2-methyl-but-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-2-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-3-en-1-yl, 2,3-dimethylbut-2-en-1-yl, 2,3-dimethylbut-3-en-1-yl, 3,3-dimethylbut-2-en-1-yl, 3,3-dimethylbut-2-en-1-yl, 1-ethyl-but-1-en-1-yl, 1-ethylbut-2-en-1-yl, 1-ethylbut-3-en-1-yl, 2-ethylbut-2-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, preferably ethenyl and prop-2-en-1-yl;

$C_2$–$C_4$-alkynyl: eth-1-yn-1-yl, prop-1-yn-1-yl, prop-2-yn-3-yl, n-but-1-yn-1-yl, n-but-1-yn-4-yl, n-but-2-yn-1-yl;

$C_3$–$C_6$-alkynyl: $C_3$–$C_4$-alkynyl as mentioned above, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl, 1-methylprop-2-yn-1-yl;

$C_3$–$C_6$-cycloalkyl-$C_1$–$C_3$-alkyl: cyclopropylmethyl, cyclobutylmethyl, cyclopentylmethyl, cyclohexylmethyl, 1-(cyclopropyl)ethyl, 1-(cyclobutyl)ethyl, 1-(cyclopentyl)ethyl, 1-(cyclohexyl)ethyl, 2-(cyclopropyl)ethyl, 2-(cyclobutyl)ethyl, 2-(cyclopentyl)ethyl, 2-(cyclohexyl)ethyl, 2-(cyclopropyl)ethyl, 3-(cyclopropyl)ethyl, 3-(cyclopropyl)propyl, 3-(cyclobutyl)propyl, 3-(cyclopentyl)propyl, 3-(cyclohexyl)propyl, in particular cyclopentylmethyl or cyclohexylmethyl;

$C_1$–$C_3$-alkoxy: $OCH_3$, $OC_2H_5$, $OCH_2$–$C_2H_5$, $OCH(CH_3)_2$, in particular $OCH_3$ or $OC_2H_5$;

$C_1$–$C_6$-alkoxy: $C_1$–$C_3$-alkoxy as mentioned above, and also, for example, n-butoxy, 1-methylpropoxy, 2-methylpropoxy or $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular $OCH_3$, $OC_2H_5$ or $OCH(CH_3)_2$;

($C_1$–$C_6$-alkoxy)carbonyl: ($C_1$–$C_4$-alkoxy)carbonyl such as $COOCH_3$, $COOC_2H_5$, n-propoxycarbonyl, $COOCH(CH_3)_2$, n-butoxycarbonyl, 1-methylpropoxycarbonyl, 2-methylpropoxycarbonyl, $COO(CH_3)_3$, ($C_4$–$C_6$-alkoxy)carbonyl such as, for example, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutbxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl, ethoxycarbonyl or 1-methylethoxycarbonyl;

cyano-$C_1$–$C_6$-alkyl: $CH_2CN$, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular $CH_2CN$ or 2-cyanoethyl;

$C_1$–$C_6$-haloalkyl and $C_1$–$C_3$-haloalkyl: $C_1$–$C_6$-alkyl and $C_1$–$C_3$-alkyl, respectively, as mentioned above which are partially or fully substituted by fluorine, chlorine and/or bromine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-chloroethyl, 2-fluoroethyl, 2,2-difluoroethyl, 2,2,2-trifluoroethyl, 2-chloro-2-fluoroethyl, 2-chloro-2,2-difluoroethyl, 1-chloro-1,2,2-trifluoroethyl, 2,2-dichloro-2-fluoroethyl, 2,2,2-trichloroethyl, pentafluoroethyl and 3-chloropropyl, 1,2,2-trifluoroethyl, preferably trifluoromethyl;

$C_3$–$C_4$-haloalkenyl: $C_3$–$C_4$-alkenyl as mentioned above which is partially or fully substituted by fluorine, chlorine and/or bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

$C_3$–$C_4$-haloalkynyl: $C_3$–$C_4$-alkynyl as mentioned above which is partially or fully substituted by fluorine, chlorine and/or bromine, i.e., for example, 3-chloropropargyl, 3-bromopropargyl, 3-fluoropropargyl, 3,3,3-trifluoropropargyl, 4-chlorobut-2-ynyl, 4-bromobut-2-ynyl, 4,4,4-trifluorobut-2-ynyl, 1,4-dichlorobut-2-ynyl, preferably 3-chloropropargyl, 3,3,3-trifluoropropargyl, 4,4,4-trifluorobut-2-ynyl;

$C_1$–$C_3$-haloalkoxy: a $C_1$–$C_3$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$–$C_2F_5$, $OCF_2$–$C_2F_5$, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

$C_3$–$C_4$-alkenyloxy: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, preferably ethenyloxy and prop-2-en-1-yloxy;

$C_3$–$C_4$-alkynyloxy: propargyloxy, prop-1-yn-1-yloxy, but-1-yn-3-yloxy, in particular propargyloxy;

$C_1$–$C_6$-alkylthio-$C_1$–$C_6$-alkyl: $C_1$–$C_6$-alkyl as mentioned above which is substituted by $C_1$–$C_6$-alkylthio, i.e., for example, methylthiomethyl, ethylthiomethyl, n-propylthiomethyl, (1-methylethylthio)methyl, n-butylthiomethyl, (1-methylpropylthio)methyl, (2-methylpropylthio)methyl, (1,1-dimethylethylthio)methyl, 2-(methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2- methylpropylthio)ethyl, 2-(1,1-dimethylethylthio)ethyl, 2-(methylthio)propyl, 2-(ethylthio)-propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl, 4-(1,1-dimethylethylthio)butyl, 5-(methylthio)pentyl, 5-(ethylthio)pentyl, 5-(n-propylthio)pentyl, 5-(1-methylethylthio)pentyl, 5-(n-butylthio)pentyl, 5-(1-methylpropylthio)pentyl, 5-(2-methylpropylthio)pentyl, 5-(1,1-dimethylethylthio)pentyl, 6-(methylthio)hexyl, 6-(ethylthio)hexyl, 6-(n-propylthio)hexyl, 6-(1-methylethylthio)hexyl, 6-(n-butylthio)hexyl, 6-(1-methylpropylthio)hexyl, 6-(2-methylpropylthio)hexyl or 6-(1,1-dimethylethylthio)hexyl, in particular methylthiomethyl or ethylthioethyl;

$C_1–C_3$-alkylthio: $SCH_3$, $SC_2H_5$, $SCH_2–C_2H_5$ and $SCH(CH_3)_2$, in particular $SCH_3$ or $SC_2H_5$; for $C_1–C_3$-haloalkylthio, what has been said for $C_1–C_3$-haloalkyl and $C_1–C_3$-alkylthio applies correspondingly;

$C_1–C_3$-alkylsulfonyl: methylsulfonyl, ethylsulfonyl, n-propylsulfonyl and 1-methylethylsulfonyl, in particular methylsulfonyl or ethylsulfonyl; for $C_1–C_3$-haloalkylsulfonyl, what has been said for $C_1–C_3$-haloalkyl and $C_1–C_3$-alkylsulfonyl applies correspondingly;

$C_1–C_3$-alkylsulfinyl: methylsulfinyl, ethylsulfinyl, n-propylsulfinyl and 1-methylethylsulfinyl, in particular methylsulfinyl or ethylsulfinyl; for $C_1–C_3$-haloalkylsulfinyl, what has been said for $C_1–C_3$-haloalkyl and $C_1–C_3$-alkylsulfinyl applies correspondingly;

$C_1–C_4$-alkoxy-$C_1–C_4$-alkyl: $C_1–C_4$-alkyl which is substituted by $C_1–C_4$-alkoxy such as methoxy, ethoxy, n-propoxy, 1-methylethoxy, n-butoxy, 1-methylpropoxy, 2-methylpropoxy and 1,1-dimethylethoxy, i.e., for example, $CH_2OCH_3$, $CH_2OC_2H_5$, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably n-propoxymethyl, (1-methylethoxy)methyl, 2-(n-propoxy)ethyl and 2-(1-methylethoxy)ethyl and particularly preferably $CH_2OCH_3$, $CH_2OC_2H_5$, 2-methoxyethyl or 2-ethoxyethyl;

$C_1–C_6$-alkoxy-$C_1–C_6$-alkyl: $C_1–C_6$-alkyl which is substituted by $C_1–C_6$-alkoxy as mentioned above, i.e., for example, methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

($C_1–C_6$-alkoxy)carbonyl-$C_1–C_2$-alkyl: $C_1–C_2$-alkyl which is substituted by ($C_1–C_6$-alkoxy)carbonyl such as $COOCH_3$, $COOC_2H_5$, n-propoxycarbonyl, $COOCH(CH_3)_2$, n-butoxycarbonyl, 1-methylpropoxycarbonyl, 2-methylpropoxycarbonyl, $COOC(CH_3)_3$, n-pentoxycarbonyl, 1-methylbutoxycarbonyl and n-hexoxycarbonyl, i.e., for example, $CH_2$—$COOCH_3$, $CH_2$—$COOC_2H_5$, n-propoxycarbonylmethyl, $CH_2$—$COOCH(CH_3)_2$, n-butoxycarbonylmethyl, (1-methylpropoxycarbonyl)methyl, (2-methylpropoxycarbonyl)methyl, $CH_2$—$COOC(CH_3)_3$, n-pentoxycarbonylmethyl, (1-methylbutoxycarbonyl)methyl, n-hexoxycarbonylmethyl, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 1-(n-pentoxycarbonyl)ethyl, 1-(1-methylbutoxycarbonyl)ethyl, 1-(n-hexoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)

ethyl, 2-(2-methylpropoxycarbonyl)ethyl, 2-(1,1-dimethylethoxycarbonyl)ethyl;

($C_1$–$C_6$-alkoxy)carbonyl-$C_1$–$C_4$-alkyl: ($C_1$–$C_6$-alkoxy)carbonyl-$C_1$–$C_2$-alkyl as mentioned above, and also 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbbnyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably $CH_2$—$COOCH_3$, $CH_2$—$COOC_2H_5$, 1-(methoxycarbonyl)ethyl, 2-(methoxycatbonyl)ethyl or 1-(ethoxycarbonyl)ethyl;

$C_1$–$C_4$-alkylcarbonyl: acetyl, propionyl, butyryl, isobutyryl;

$C_1$–$C_4$-alkoximinomethyl: methoxyiminomethyl, ethoxyiminomethyl, propoxyiminomethyl, isopropoxyiminomethyl, n-butoxyiminomethyl, sec-butoxyiminomethyl, isobutoxyiminomethyl, tert-butoxyiminomethyl;

($C_1$–$C_6$-alkoxy)carbonyl-$C_1$–$C_6$-alkyl: $C_1$–$C_6$-alkyl which is substituted by ($C_1$–$C_6$-alkoxy)carbonyl as mentioned above, i.e., for example, methoxycarbonylmethyl, ethoxycarbonylmethyl, 1-(methoxycarbonyl)ethyl, 2-(methQxycarbonyl)ethyl, 2-(ethoxycarbonyl)ethyl, 3-(methoxycarbonyl)propyl, 4-(methoxycarbonyl)butyl, 5-(methoxycarbonyl)pentyl or 6-(methoxycarbonyl)hexyl;

$C_3$–$C_6$cycloalkoxy-$C_1$–$C_3$-alkyl: cyclopropyloxymethyl, cyclobutyloxymethyl, cyclopentyloxymethyl, cyclohexyloxymethyl, 1-(cyclopropyloxy)ethyl, 1-(cyclobutyloxy)ethyl, 1-(cyclopentyloxy)ethyl, 1-(cyclohexyloxy)ethyl, 2-(cyclopropyloxy)ethyl, 2-(cyclobutyloxy)ethyl, 2-(cyclopentyloxy)ethyl, 2-(cyclohexyloxy)ethyl, 3-(cyclopropyloxy)propyl, 3-(cyclobutyloxy)propyl, 3-(cyclopentyloxypropyl or 3-(cyclohexyloxy)propyl, in particular cyclopentyloxymethyl, cyclohexyloxymethyl or 2-(cyclopentyloxy)ethyl;

$C_3$–$C_6$- or $C_3$–$C_7$-cycloalkyl: cyclopropyl, cyclobutyl, cyclopentyl, cyclohexyl or cycloheptyl;

$C_3$–$C_6$-cycloalkenyl: 1-cyclopropen-3-yl, 1-cyclobuten-3-yl, 1-cyclobuten-4-yl, 1-cyclopenten-3-yl, 1-cyclopenten-4-yl, 1-cyclohexen-3-yl or 1-cyclohexen-4-yl;

Examples of saturated 3- to 7-membered heterocyclyl are: oxiranyl, thiiranyl, oxetan-2-yl, oxetan-3-yl, thietan-2-yl, thietan-3-yl, tetrahydrofuran-2-yl, tetrahydrofuran-3-yl, tetrahydrothiophen-2-yl, tetrahydrothiophen-3-yl, 1,3-dioxolan-2-yl, 1,3-dioxolan-4-yl, 1,3-dithiolan-2-yl, 1,3-dithiolan-4-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-6-yl, 1,4-dioxepan-2-yl or 1,4-dioxepan-7-yl.

Examples of unsaturated 3- to 7-membered heterocyclyl are: oxirenyl, thiirenyl, oxet-3-yl, thiet-3-yl, 1,2-dihydrofuran-2-yl, 1,2-dihydrofuran-3-yl, 1,2-dihydrothiophen-2-yl, 1,2-dihydrothiophen-3-yl, furan-2-yl, furan-3-yl, pyrrol-2-yl, pyrrol-3-yl, thiophen-2-yl, thiophen-3-yl, 1,3-dioxol-2-yl, 1,3-oxathiol-2-yl, 1,3-dithiol-2-yl, 2,3-dihydropyran-4-yl, 2,3-dihydropyran-5-yl, 2,3-dihydropyran-6-yl, 2,3-dihydrothiopyran-4-yl, 2,3-dihydrothiopyran-5-yl, 2,3-dihydrothiopyran-6-yl, oxazol-2-yl, oxazol-4-yl, oxazol-5-yl, isoxazol-3-yl, isoxazol-4-yl, isoxazol-5-yl, oxepin-2-yl, oxepin-3-yl, oxepin-4-yl, thiepin-2-yl, thiepin-3-yl, 1,3-dioxepin-2-yl, 1,3-dioxepin-4-yl or 1,3-dithiepin-2-yl.

The pyridine-2,3-dicarboxamides according to the invention can be prepared by literature methods known per se, for example analogously to the synthesis routes described in EP 799 825. EP 799 825 is expressly incorporated herein in full by way of reference.

The preferred preparation process comprises the reaction of a pyridine-2,3-dicarboxylic anhydride compound of the formula

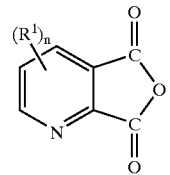

with an amine of the formula Q—$NH_2$. The reaction gives one of the compounds of the formulae

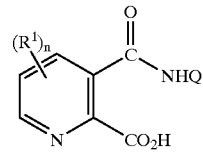 and 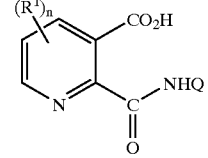

or a mixture thereof. In general, the reaction is carried out in an inert solvent, for example a chlorinated solvent, such as dichloromethane or 1,2-dichloroethane, an aromatic hydrocarbon, such as toluene or xylene, or an ether, such as diethyl ether, dioxane or tetrahydrofuran. The reaction can be carried out in a wide temperature range, for example from room temperature to the boiling point of the solvent.

The reaction product is cyclized with a dehydrating agent such as acetic anhydride or thionyl chloride with or without inert solvent to give an imide of the formula

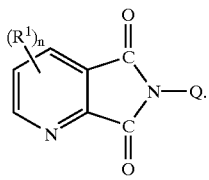

5

Suitable inert solvents are the solvents mentioned above. Alternatively, the amines of the formula Q—NH can also be reacted directly in the melt, preferably at 150–250° C., to give the imide.

The imide is then reacted with an amine of the formula $NHR^5R^6$ to give the corresponding compound of the formula I ($R^1$, Q, $R^5$, $R^6$ and n are as defined above). The reaction conditions for the above reaction steps are described in detail in EP-A-799 825. If the compound desired is a compound of the formula I where m=1, an oxidation is carried out at the imide stage using a suitable oxidizing agent, such as hydrogen peroxide or organic peracids, for example peracetic acid or m-chloroperbenzoic acid, see EP-A-799 825. The pyridine-2,3-dicarboxylic anhydrides can be prepared by known processes, for example by treating pyridine-2,3-dicarboxylic acids with phosgene in the presence of dimethylformamide, according to the process described in U.S. Pat. No. 4,439 607.

Other pyridinedicarboxylic acid starting materials are described in EP 227 932, 322 616, 461 403, 422 456, 661 282 and 663 399, or they can be prepared by the methods described therein. The amines of the formulae Q—$NH_2$ and $HNR^5R^6$ are known or can be prepared by processes known to a person skilled in the art.

Substituted anilines of the formula 1 (which correspond to $H_2N$—$Q_1$)

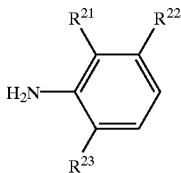

1 where the variables $R^{21}$, $R^{22}$ and $R^{23}$ are as defined below:

$R^{21}$ is $C_1$–$C_3$-alkoxymethyl, $C_1$–$C_3$-alkoximinomethyl, $C_1$–$C_3$-alkoxycarbonyl, $C_1$–$C_3$-alkylthiocarbonyl, $C(O)NH_2$, CN, Cl, Br, $C_1$–$C_3$-alkyl;

$R^{22}$ is Cl, Br, $C_1$–$C_3$-alkyl;

$R^{23}$ is hydrogen, $C_1$–$C_3$-alkoxymethyl, $C_1$–$C_3$-alkoxycarbonyl, $C_1$–$C_3$-alkylthiocarbonyl, $C(O)NH_2$, CN, Cl, Br, $C_1$–$C_3$-alkyl, $C_1$–$C_3$-alkoxy;

are starting materials for some of the compounds of the formula I where Q=$Q_1$.

The anilines of the formula I can be prepared by one of the processes below. The isatoic anhydrides to be used as starting materials and their preparation are known per se and described in the literature, for example in Chem. Abstr. 75, 98482; 117, 233811; 125, 300514. The 3-chloro-6-methylisatoic anhydride is described in more detail under the synthesis of the starting materials.

The substituted anilines of the formula 1a in which $R^{21}$ is a $C_1$–$C_3$-alkoximinomethyl radical are prepared by a process known per se by reacting, for example, a substituted o-nitrobenzaldehyde of the formula 2

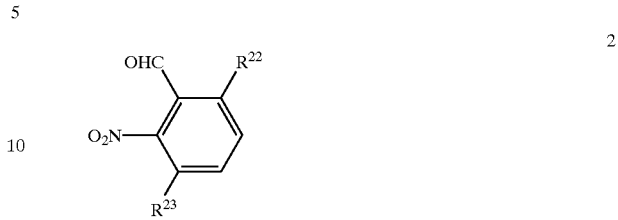

2 with hydroxylamine hydrochloride in the presence of a base and reacting the resulting oxime of the formula 4

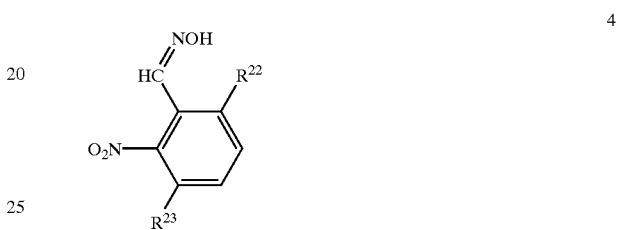

4 with an alkylating agent of the formula RG where R is a $C_1$–$C_3$-alkyl radical and G is a nucleophilic displaceable leaving group in the presence of a base and reducing the resulting oxime ether of the formula 6

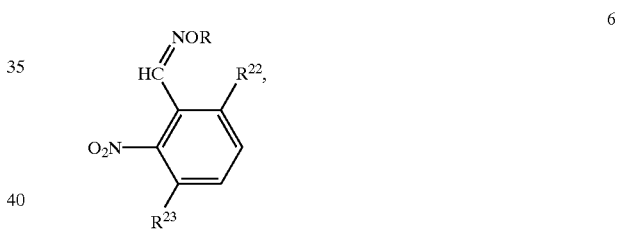

6 for example with iron in the presence of an acid or with hydrogen in the presence of a metal catalyst.

Examples of suitable nucleophilically displaceable leaving groups are halogen, preferably chlorine, bromine or iodine, $C_1$–$C_3$-alkylsulfonyloxy, such as methylsulfonyloxy, phenylsulfonyloxy, where the phenyl radical may be unsubstituted or mono- or polysubstituted by halogen or $C_1$–$C_6$-alkyl, such as phenylsulfonyloxy, p-toluenesulfonyloxy or p-$C_1$–phenylsulfonyloxy, or a $C_1$–$C_3$-dialkyl sulfate, such as dimethyl sulfate or diethyl sulfate.

However, the oxime ethers of the formula 6 can also be prepared by direct oximation of a substituted o-nitrobenzaldehyde 2 with a $C_1$–$C_3$-alkoxyamine of the formula 7

$H_2NOAlk$  7 or a salt thereof, for example the hydrochloride, in the presence of a base, followed by reduction as above to give the aniline 1.

The substituted anilines of the formula 1b in which one of the radicals $R^{21}$ or $R^{23}$ is a carboxylic acid function are likewise prepared by a process known per se by converting, for example, a substituted aniline of the formula 8a or 8b

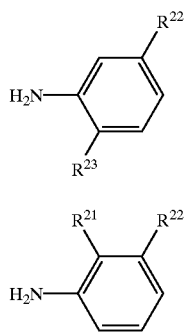

8a

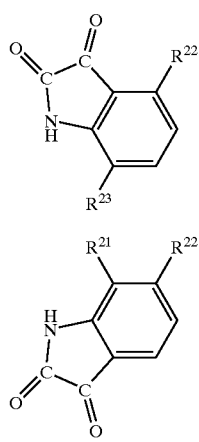

8b with chloral hydrate and hydroxylamine sulfate into the corresponding isonitrosoacetanilides of the formulae 9a and 9b, respectively, 9a 9b which are then cyclized in the presence of an acid, for example sulfuric acid, to give the corresponding isatins of the formulae 10a and 10b, respectively,

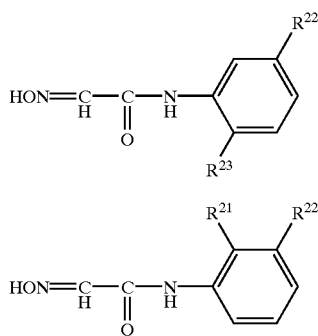

10a

10b and the latter are reacted with $C_1$–$C_3$-alkanols in the presence of alkali metal $C_1$–$C_3$-alkoxides in the presence of aqueous hydrogen peroxide to give the corresponding anthranilic esters of the formulae 13a and 13b, respectively.

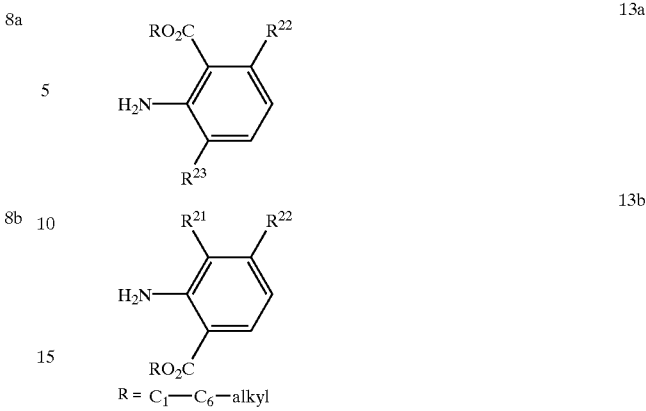

13a

13b

R = $C_1$—$C_6$—alkyl

These compounds, for their part, can be converted by transesterification with higher alcohols or thiols into the corresponding long-chain anthranilic esters or anthranilic thioesters.

If the isatins of the formulae 10a and 10b are reacted with hydroxylamine as described for the oximes 4, the isatin β-oxires of the formulae 14a and 14b, respectively,

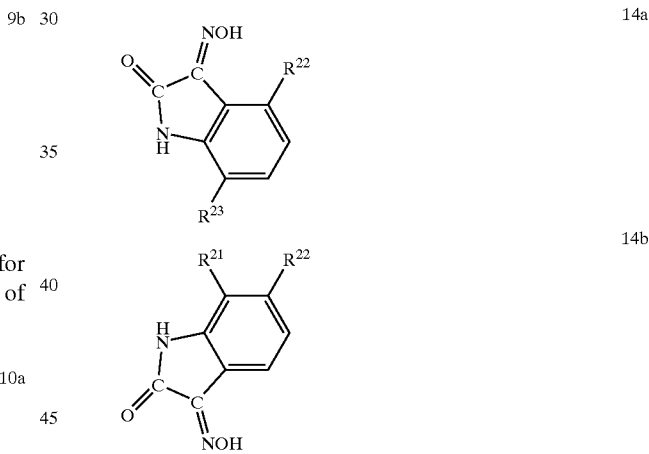

14a

14b are obtained which, by heating under reduced pressure in the presence of inert solvents whose boiling points are not below the boiling points of the cleavage products formed, for example diethyl glycol ether, diethylene glycol dimethyl ether, tetraethylurea, tetrabutylurea, dimethylethyleneurea, dimethylpropyleneurea, diethyl phthalate, diethylhexyl phthalate, octaethylene glycol or nonaethylene glycol, are reacted to give the corresponding o-aminobenzonitriles of the formulae 15a and 15b, respectively,

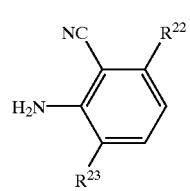

15a

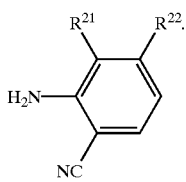

15b

According to a further process, the isatins of the formula 10a and 10b can also be reacted with aqueous hydrogen peroxide in an aliphatic carboxylic acid, such as glacial acetic acid, in the presence of conc. sulfuric acid to give the isatoic anhydrides of the formulae 16a and 16b, respectively.

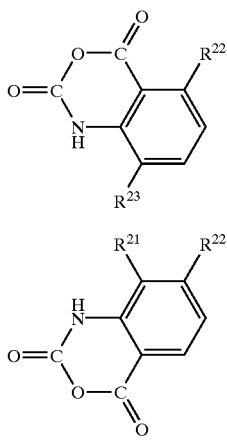

16a

16b

The latter can, similarly to the corresponding reaction of the isatins 10a and 10b, be converted in an alternative reaction using $C_{1-3}$-alkanols in the presence of a base into the anthranilic esters of the formulae 13a and 13b, respectively.

If the nucleophile used is aqueous ammonia, instead of the anthranilic esters, the carbamoyl derivatives 17a and 17b, respectively, are obtained.

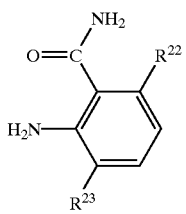

17a

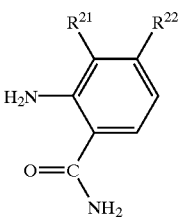

17b

These can be converted—expediently after conversion into corresponding mineral acid salts—into the corresponding nitriles of the formulae 15a and 15b, respectively,

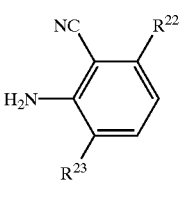

15a

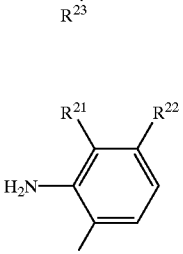

15b by using dehydrating agents, for example phosphorus oxychloride.

The preparation of the compounds 1az in which $R^{21}$ is a methoximinomethyl radical is represented in an exemplary manner by the reaction described in scheme 1 below, where, starting from a substituted o-nitrobenzaldehyde 2z, the oxime ether 6z is obtained by reaction with hydroxylaminme hydrochloride in the presence of a base and subsequent-methylation, for example with methyl iodide. The oxime ether can also be obtained by direct reaction with methylhydroxylamine hydrochloride 7 in the presence of a base and then be reduced to the aniline derivative 1az, for example by reduction with iron.

Scheme 1

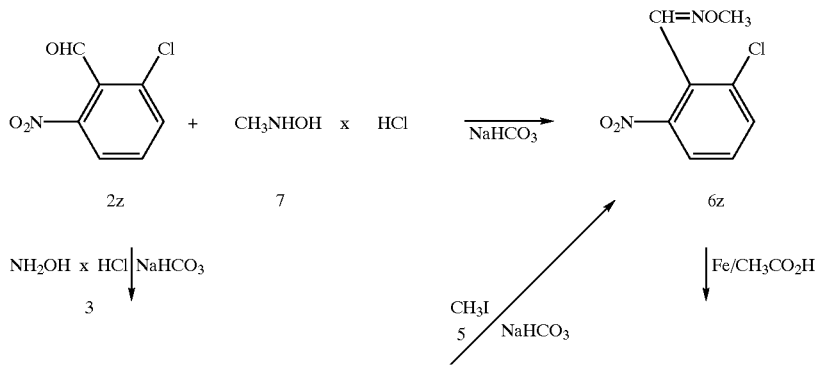

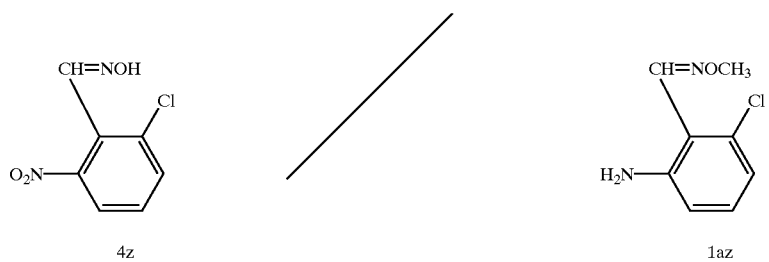

Methods for preparing oxime ethers are described in Synthesis 1984, 266, Chem. Ber. 83, (1950), 78 and 34 (1901), 1330.

For preparing the isatins required as further starting materials, for example the isatins 10az or 10bz, substituted anilines 8az or 8bz are reacted with chloral hydrate and hydroxylamine to give the corresponding isonitrosoacetanilides 9az and 9bz, respectively, and these are cyclized with sulfuric acid according to scheme 2 below. The synthesis of isatins is described, for example, in Beilstein, 21, I 402–405 and 21, IV 5451.

The isatins 10az and 10bz can be converted for example by reaction with methanol in the presence of sodium methoxide and aqueous hydrogen peroxide into anthranilic acid methyl esters 13az and 13bz, respectively, according to scheme 3. The process is described in EP 32672 A. The isatins 10az and 10bz can furthermore also be converted, according to JP-A-62234080 into their β-oximes, and these can be converted by heating under reduced pressure according to the process of DE 12 31 709 into substituted o-aminobenzonitriles 15az and 15bz, respectively, see also scheme 3.

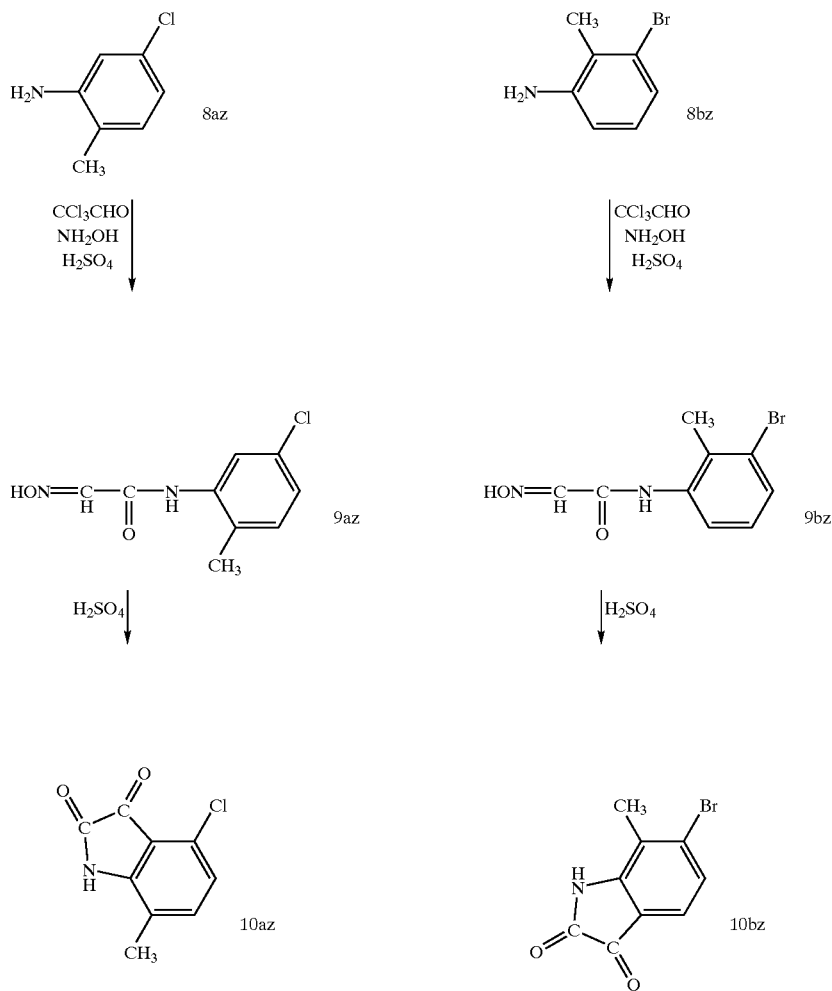

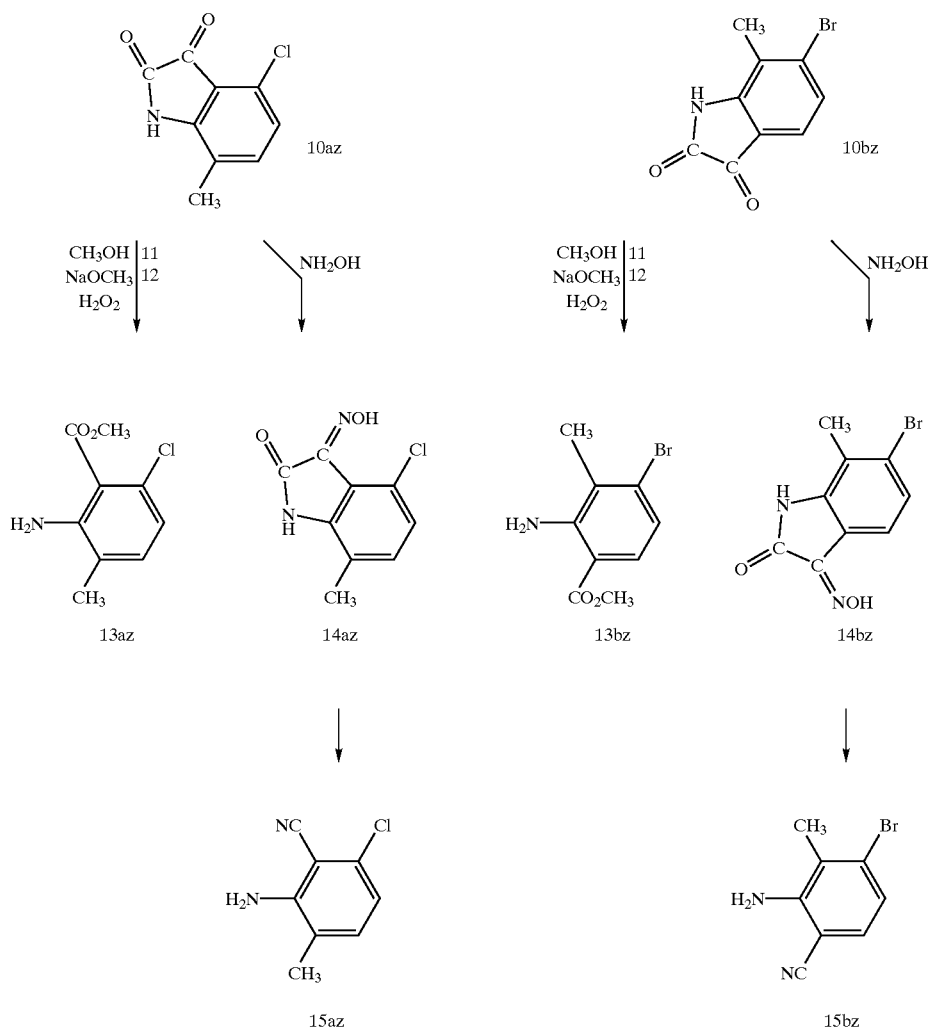

However, according to an alternative process, it is also possible, according to Angew. Chem. 92 (1980), 196, to react the isatins 10az or 10bz initially with aqueous hydrogen peroxide in an aliphatic carboxylic acid, such as glacial acetic acid, in the presence of conc. sulfuric acid to give the isatoic anhydrides 16az and 16bz, respectively, according to scheme 4. The latter give, when reacted with alcohols in the presence of a base, for example triethylamine, the anthranilic esters 13az and 13bz, respectively. Reaction with aqueous ammonia gives, according to scheme 4, the carbamoyl derivatives 17az and 17bz, respectively. These can be converted, expediently in the form of their salts—for example as hydrochlorides—into the corresponding nitrites 15az and l5bz, respectively, using dehydrating agents such as phosphorus oxychloride.

Scheme 4

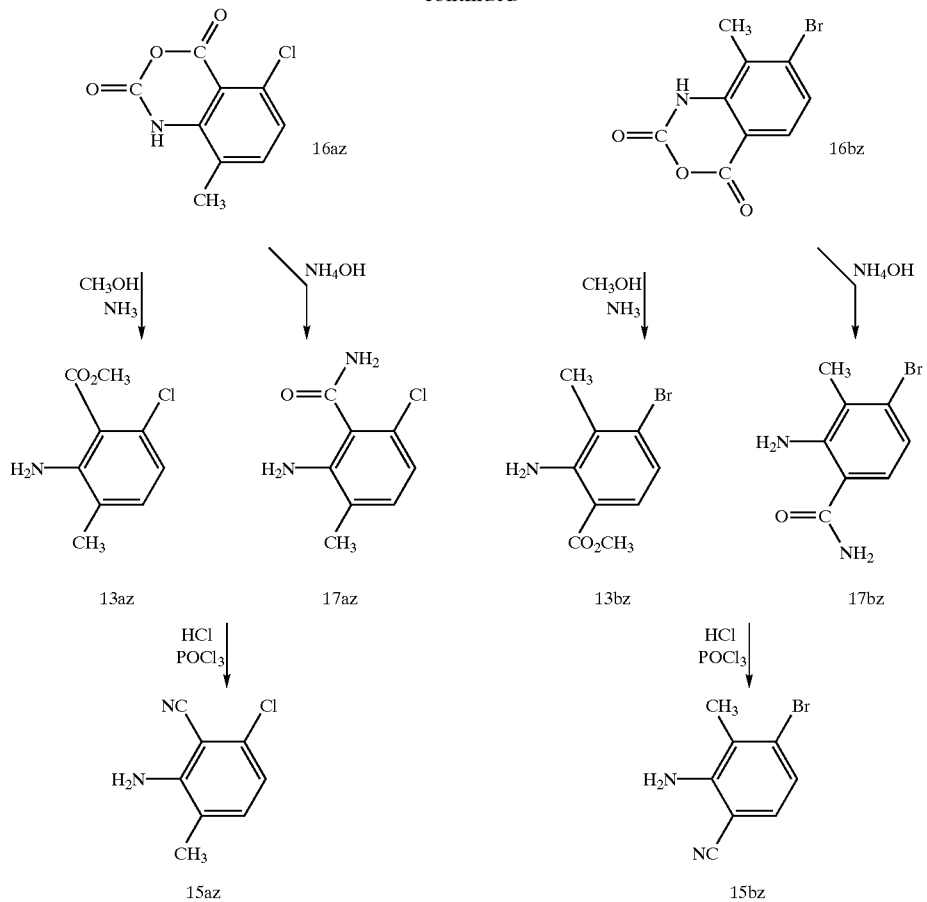

Ring-opening of isatoic anhydrides with alcohols are described in J. Med. Chem. 31 (1988), 2136 and in WO 97/08130. If the nucleophile used for opening the ring is aqueous ammonia, the procedure of DE 15 43 332 can be adopted. Dehydration of the carbamoyl derivatives to give the corresponding benzonitriles can be carried out according to the procedures of J. Chem. Soc. Chem. Commun. 1994, (15), 1767 and J. Heterocycl. Chem. 34 (1997), 1661.

3-Chloro-2-methoxymethylaniline is disclosed in EP 127 114 and DE 2345 443; according to schemes 2–4, it can be converted into corresponding 6-substituted carboxylic acid derivatives.

However, it is additionally also possible to convert anthranilic esters of the formula 13a or 13b

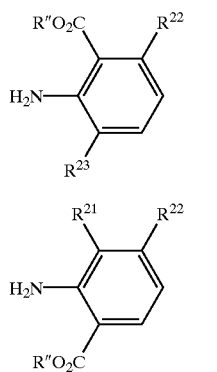

in which R" is, for example, a $C_1$–$C_3$-alkyl radical and $R^{21}$, $R^{22}$ and $R^{23}$ are Cl, Br, $C_2$–$C_3$-alkyl, $R^{21}$ and $R^{23}$ are furthermore CN or $C_1$–$C_3$-alkoxycarbonyl or $R^{23}$ is furthermore $C_1$–$C_3$-alkoxy, for example after protection of the amino group with an acylating agent 18

R'C(O)G    18 in which R' is a $C_1$–$C_4$-alkyl radical; and G is a nucleophilically displaceable leaving group (examples have already been mentioned above), into the acylanilines 19a and 19b, respectively,

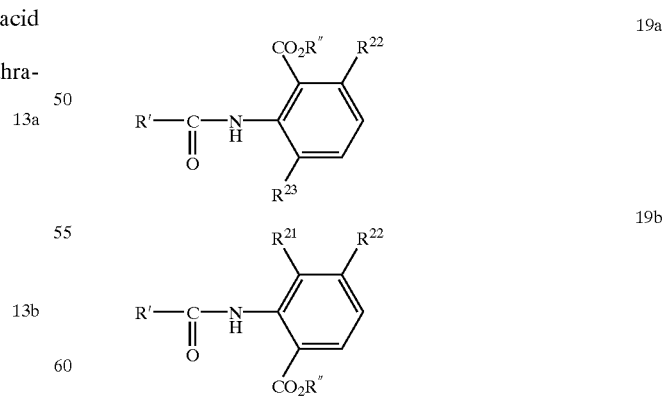

to reduce these with a complex metal hydride 20

$Me^I Me^{III} H_4$    20 in which $Me^I$ and $Me^{III}$ are each metals of the first or third main group to the benzyl alcohols 21a and 21b, respectively,

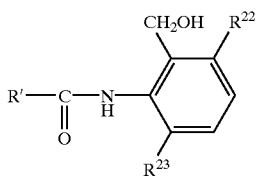
21a

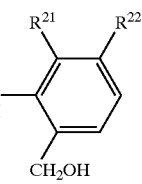
21b which are reacted with an alkylating agent RG (R=$C_1$–$C_3$-alkyl) in the presence of a base to give the alkoxymethyl derivatives 22a and 22b, respectively,

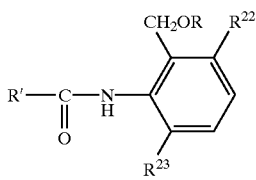
22a

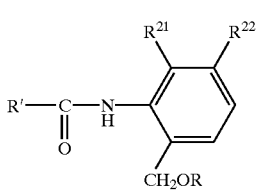
22b and converting the latter in the presence of aqueous alkali or mineral acid with removal of the protective group into the free anilines 23a and 23b, respectively.

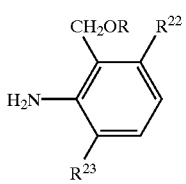
23a

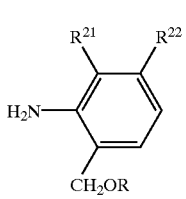
23b

Instead of the anthranilic esters 13a or 13b, it is also possible to use the corresponding anthranilic acids for the reduction.

If the anilines 13az or 13bz in which $R^{23}$ or $R^{21}$ and R" are methyl and $R^{22}$ is Cl, the preparation is carried out using, for example, methoxymethyl derivatives 23az and 23bz, respectively, according to scheme 5:

Scheme 5

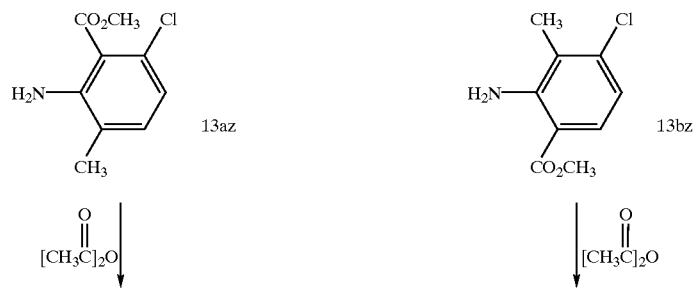

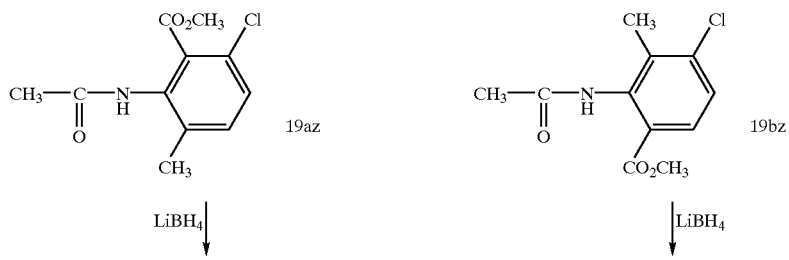

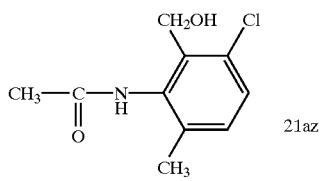
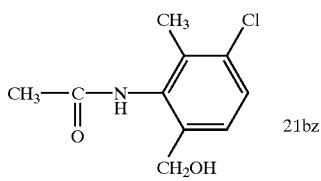

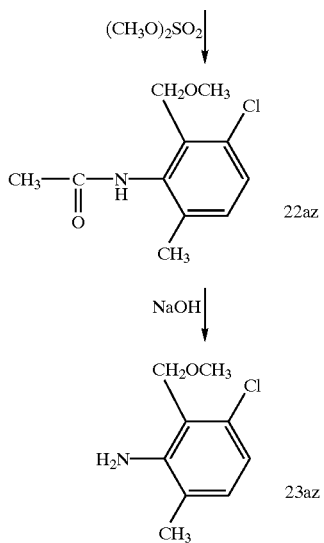
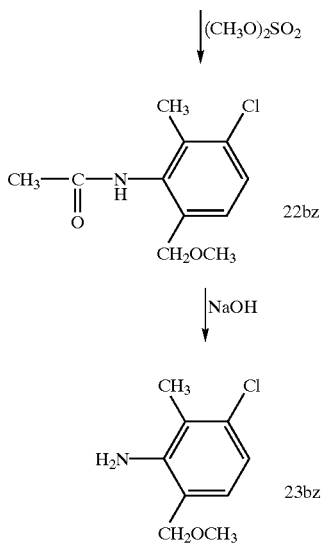

However, it is also possible to halogenate the acylanilines of the formulae 19c or 19d

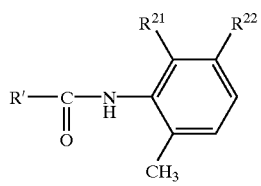

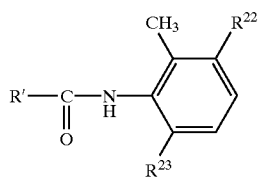

in which $R^{21}$ and $R^{23}$ are Cl, Br, CN or $C_1$–$C_3$-alkoxycarbonyl and $R^{22}$ is Cl or Br on the tolyl side chain to give the benzyl halides 24c and 24d, respectively, in which Hal is Cl or Br

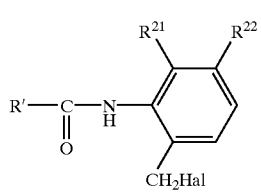

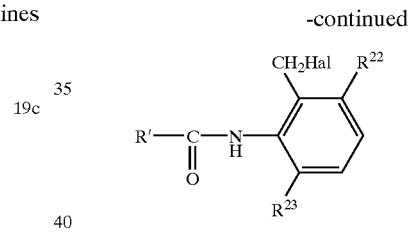

and to react these with an alcohol R'" OH or an alkoxide R'" OMe in which R'" is a $C_1$–$C_3$-alkyl radical and Me is an alkali metal or alkaline earth metal atom, if appropriate in the presence of a base, to give the benzyl ethers 22c and 22d, respectively,

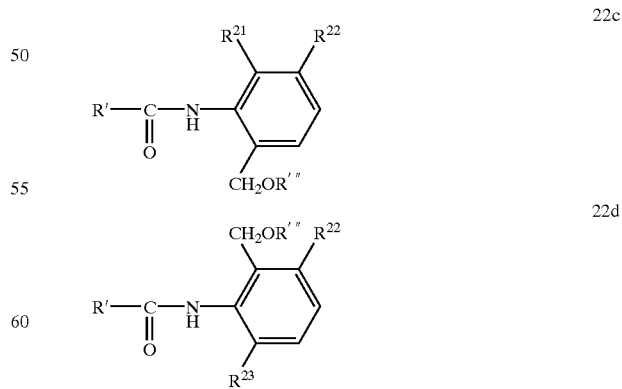

and to cleave these in the presence of aqueous alkali or dilute sulfuric, hydrochloric or phosphoric acid to give the free anilines 23c and 23d, respectively.

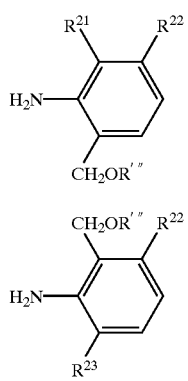

If the acylanilines 19cz or 19dz in which $R^{21}$ and $R^{23}$ are CN and $R^{22}$ is Cl are used, the methoxymethyl derivatives 23cz and 23dz, respectively, are prepared, for example, according to scheme 6:

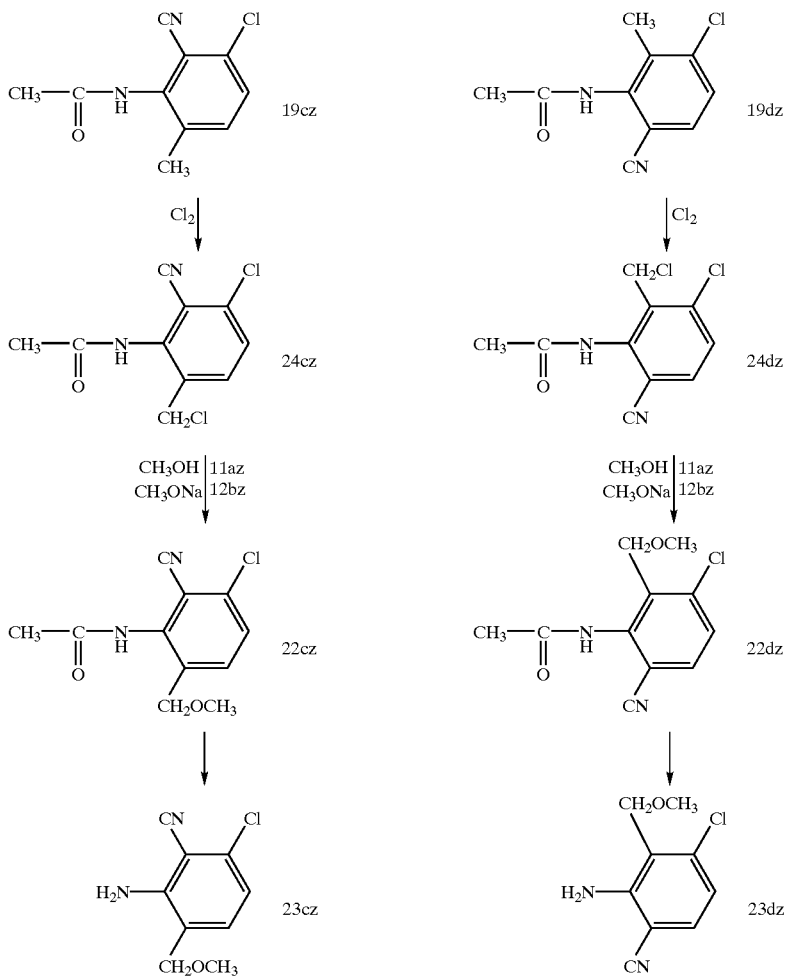

If, instead of the nitrites 19cz or 19dz, the corresponding anthranilic esters are used, these are usually likewise hydrolyzed during the removal of the acylamino group, so that subsequently, they have to be re-esterified, for example by boiling under reflux in alcoholic hydrochloric acid during which hydrogen chloride gas is passed through.

Hereinbelow, the reaction steps of scheme 1 are illustrated in more detail. The alkylhydroxylamine is freed as base by adding an alkali metal bicarbonate or alkaline earth metal bicarbonate with stirring to the aqueous solution of an O-alkylhydroxylamine hydrochloride at 10–30° C. for 5–30 min.

Suitable alkali metal or alkaline earth metal bicarbonates are sodium bicarbonate, potassium bicarbonate, magnesium bicarbonate and calcium bicarbonate.

The free hydroxylamine is added with stirring over a period of 10–30 min as an aqueous solution at 40–70° C., preferably 50–60° C., to the solution of the nitrobenzaldehyde in an inert organic solvent, and the mixture is stirred at 50° C. for 1–4, preferably 2–3 h.

The molar ratio of starting material 2 to 7 is generally from 0.9 to 1.2, preferably from 0.95 to 1.1.

Instead of the O-alkylhydroxylamine hydrochloride, it is also possible to convert hydroxylamine hydrochloride in an analogous manner into the free base and to react it as described with the aldehyde derivative 2. The resulting oxime 4 then has to be alkylated with an alkylating agent 5.

Suitable alkylating agents 5 are alkyl halides, for example alkyl chlorides, bromides or iodides, dialkyl sulfates or arylsulfonic esters. The alkylating agent is expediently allowed to act on the oxime 5 in the presence of a base at 10–60° C., preferably 20–40° C., for 0.5–5 h, in particular 1–2 h.

Suitable for use as bases are the abovementioned bicarbonates, furthermore alkali metal or alkaline earth metal carbonates, and also alkali metal and alkaline earth metal hydroxides. Alkali metal preferably denotes sodium and potassium, alkaline earth metal denotes magnesium and calcium.

The molar ratio of 4 to 5 is generally from 0.9 to 1.4, preferably from 1.1 to 1.2.

Similar alkylations are described in Houben-Weyl, Methoden der organischen Chemie [Methods of organic Chemistry], IV Edition, Volume VI/3, pp. 24–37.

The resulting oxime ethers 6 are then reduced using iron in the presence of an acid. Advantageously, the oxime ether 6 is, in a mixture of a carboxylic acid such as acetic acid and an alcohol such as methanol, brought into contact with a mixture of iron powder in the same mixture of carboxylic acid and alcohol, at 70–80° C., for 2–6 h, advantageously 3–4 h.

However, the reduction of the oxime ether 6 can also be carried out using hydrogen in the presence of a metal catalyst, at 10–40° C. It is also possible to carry out the reduction under pressure in an autoclave, for example using Raney nickel. The hydrogenation is expediently carried out at 20–80° C., advantageously 40–60° C., and a hydrogen pressure of 1–50 bar, advantageously 10–20 bar.

Suitable metal catalysts are platinum, palladium, Raney nickel, Raney cobalt or else platinum oxide. Suitable hydrogenation methods are described in Houben-Weyl, Methoden der Organischen Chemie, IV. Edition, Volume XI/1, pp. 341–359.

In the reaction steps shown in scheme 2, the aniline 8 is expediently initially charged in water, and initially hydroxylammonium sulfate, a little at a time, then, dropwise, conc. sulfuric acid and finally chloral are added successively with stirring at 20–40° C. The mixture is heated at 50° C. for 10–30 min and then adjusted to pH 1.5–2 by addition of conc. aqueous sodium hydroxide solution. After 6–16 h, advantageously 8–12 h, at room temperature the precipitate formed is isolated, taken up in a base and washed with a water-immiscible organic solvent, and the isonitrosoacetanilide 9 is precipitated by addition of an acid, for example sulfuric acid.

In general, from about 0.9 to 1.2, preferably from 0.95 to 1.05, mol of chloral and from 2 to 4 mol, preferably from 2 to 3 mol, of hydroxylammonium sulfate are employed per mole of 7.

For cyclizing the isonitrosoacetanilides 9 to the corresponding isatins 10, the starting materials 9 are treated at 60–90° C., advantageously 70–80° C., with a strong acid, for example 90% strength sulfuric acid, for 2 to 5 h.

Starting materials 9 and 10 are synthesized according to the preparation methods described in Beilstein, Volume 21, 402–405.

In the reaction steps shown in scheme 3, the isatins 10 are oxidized with hydrogen peroxide in the presence of alcohols 11 and alkali metal alkoxides 12 to give the anthranilic esters 13. To this end, aqueous hydrogen peroxide is added with cooling to the starting material 10 in a mixture of an alcohol 9 and its alkali metal alkoxide, and the compound is treated at room temperature for 20–60 min, expediently 30–40 min.

The molar amounts in which the starting materials are reacted are from 40 to 100, in particular from 60 to 80, mol of alcohol, from 1 to 5 mol, in particular from 1 to 3 mol, of alkali metal alkoxide and from 1 to 3, in particular from 1 to 1.5, mol of hydrogen peroxide per mole of isatin 10.

Here, the anthranilic esters 13 are prepared according to the process described in EP 32 672.

The isatins 10 can furthermore also be converted into their β-oximes by the route described in scheme 1, and additionally also according to J. Heterocycl. Chem. 17 (1980), 65.

If these are heated in the presence of inert solvents or diluents having boiling points which are not lower than that of the boiling point of the o-aminobenzonitriles 15 formed, to 200–400° C., preferably 200–300° C., at 0.1–200 mbar, preferably 10–120 mbar, the compounds 15 distill over in high purity. Suitable inert solvents and diluents have already been mentioned above. The preparation is carried out according to the procedure described in DE 12 31 709.

In the reaction steps shown in scheme 4, the isatins 10 are oxidized with hydrogen peroxide in a carboxylic acid such as acetic acid as reaction medium in the presence of catalytic amounts of sulfuric acid, initially to the isatoic anhydrides 16. To this end, the isatins 10 are treated in acetic acid with (per mole of isatin 10) 4–8 ml, preferably 5–6 ml, of conc. sulfuric acid and hydrogen peroxide, and the reaction temperature is kept at 50–80° C., preferably 60–70° C. The molar amounts of hydrogen peroxide per mole of isatin 10 are from 0.95 to 1.3, preferably from 1.0 to 1.15, mol.

The preparation is carried out according to the procedure described in Angew. Chem. 92 (1980), 196.

For converting the isatoic anhydrides 16 into the anthranilic esters 13, the starting materials 16 are suspended in excess alcohol as reaction medium, from 0.6 to 1 mol, preferably from 0.7 to 0.9 mol, of an organic acid such as triethylamine, tri-n-propylamine, cyclohexyldimethylamine or N-methylmorpholine are added per mole of starting material 16 and the mixture is reacted at 50–80° C., preferably 60–70° C., for 1 to 5 h, preferably 2 to 3 h. The anthranilic esters 13 are obtained in a customary manner. Instead of the abovementioned organic bases, it is also possible to use 1–10, preferably 2–5, mol % of a highly nucleophilic organic base such as 4-dimethylaminopyridine as catalyst.

The process is carried out according to the procedure described in WO 97/08130 and J. Med. Chem. 31 (1988), 2136.

Instead of using alcohols, it is also possible to open the ring of the isatoic anhydride 16 with ammonia to give the anthranilamides 17. To this end, aqueous ammonia and compound 16 are brought into contact in a polar aqueous solvent such as dimethylformamide, dimethylacetamide or N-methylpyrrolidone, at 70–95° C., advantageously 80–90° C. The amount of ammonia, based on the starting material 16, is from 0.95 to 1.3, preferably from 1.1 to 1.2 mol.

The process is carried out according to the procedure described in D-A-1543 332.

To convert the anthranilamides 17 into the corresponding benzonitriles 15, the starting materials 17, expediently in the form of the hydrochloride, are treated with dehydrating agents such as phosphorus oxychloride at 110–150° C., preferably 120–130° C., for 1 to 8 h, advantageously 3 to 4 h. The process follows the procedures described in J. Chem. Soc. Chem. Comm. 1994 (15), 1767 and J. Heterocycl. Chem. 34 (1997), 1661.

In the reaction steps shown in scheme 5, the anthranilic ester 13 is protected with an acyl radical. Suitable acylating agents are chlorides or bromides of acetic acid, propionic acid, butyric acid, isobutyric acid or valeric acid and furthermore the anhydrides of these acids. It is also possible to use mixed anhydrides, for example formyl acetate. If an anhydride is used, the acylating agent is expediently allowed to act on the anthranilic ester in an inert solvent at 20–140°

C., advantageously 80–120° C., for 4–20 h, advantageously 6–12 h. If the acylating agent used is an acid chloride, the acid chloride is brought into contact with a mixture of the anthranilic ester 13 and a base in an inert solvent at 10–60° C., advantageously 20–30° C., for 2 to 20 h, advantageously 6 to 12 h. Suitable for use as bases are the abovementioned organic and inorganic bases and furthermore pyridine, α-, β-, γ-picoline, lutidine, quinoline and acridine. If acid chlorides or bromides are used, it is also possible to carry out the reaction in a two-phase system that is formed when water is used. If the acylating agent used is an anhydride, the acylation can also be accelerated catalytically by highly nucleophilic bases, such as p-dimethylaminopyridine or p-pyrrolidonopyridine. The molar ratios in which the starting materials are reacted with one another are from 0.95 to 1.3, advantageously from 1.0 to 1.1, mol of acylating agent and base per mole of anthranilic ester 13. The catalyst is advantageously employed in an amount of from 0.5 to 1.0, advantageously 1 to 3, mol % per mole of anthranilic ester 13.

To reduce the acylated anthranilic ester 19, the ester is, in an inert solvent, brought into contact with a complex metal hydride, such as sodium borohydride, in one of the solvents mentioned above at 10–65° C., advantageously 20–50° C., for 2 to 10 h, advantageously 3 to 6 h. Suitable inert solvents are acetonitrile or aqueous alcohols (if sodium borohydride is used) or diisopropyl ether or tetrahydrofuran (if lithium aluminum hydride or lithium borohydride is used).

The molar ratios in which the starting materials are reacted with each other are from 0.5 to 3, preferably from 0.75 to 2.5, mol of lithium borohydride per mole of starting material 20.

It is also possible to hydrolyze the ester group of the starting materials 19 by treatment with from 0.95 to 1.1 mol, advantageously from 1.0 to 1.03 mol, of aqueous alkali at 10–80° C., advantageously 20–60° C., for 1 to 10 h, advantageously 2 to 6 h, followed by reduction with a complex metal hydride as above. The process follows the procedure described in organikum, VEB Deutscher Verlag der Wissenschaften, Berlin 1976, 15th Edition, pp. 612–616.

The benzyl alcohols 21 are then alkylated by treatment with an alkylating agent 5. The reaction is carried out under the same reaction conditions as for the alkylation of the oxime 4 according to scheme 1.

To release the o-alkoxymethylaniline 23, compound 22 is hydrolyzed with aqueous alkali, expediently from 0.95 to 1.2 mol, advantageously from 1.0 to 1.1 mol, at 20–120° C. for 1 to 12 h, advantageously at 60–100° C. for 2 to 8 h.

In the reaction steps shown in scheme 6, the protected anilines 19 are subjected to a chlorination in their tolyl side-chain. For this purpose, it is possible to use elemental chlorine and an apparatus for continuous chlorination, as described in Houben-weyl, Methoden der organischen Chemie, 4th Edition, Volume 5/3, p. 520 for the chlorination of toluene to benzyl chloride. However, it is also possible to use N-chloro- or N-bromo compounds having positively induced halogen, described ibid. p. 800. On pp.800–801, for example, the chlorination of toluene with N-chlorosuccinimide under irradiation with light or with addition of peroxides for side-chain chlorination is described in more detail.

Ibid. p. 807 illustrates the chlorination of the tolyl side-chain using 1,3-dichloro-5,5-dimethylhydantoin. Instead of elemental halogen, itwis also possible to use sulfuryl chloride, which acts more gently, and to catalyze the reaction by adding a free-radical initiator, such as azoisobutyronitrile or benzoyl peroxide. The reaction follows the procedure described in Houben-Weyl, volume v/3, p. 892.

Suitable solvents are relatively highly chlorinated hydrocarbons, such as dichloro- and trichlorobenzene, chloroform and in particular carbon tetrachloride, and furthermore acetonitrile or acetic acid. However, it is also possible to carry out the reaction in the absence of a solvent and to introduce chlorine or sulfuryl chloride directly into a melt of the starting material 20.

The amount of chlorinating agent used is from 0.7 to 1.5, expediently from 0.95 to 1.1, mol of chlorinating agent per mole of starting material 20. Depending on the chlorinating agent, the reaction is carried out at 10–200° C., advantageously 20–150° C., for 10 min to 10 h, advantageously for 0.5 to 6 h.

To convert the benzyl chlorides 24 into their alkoxymethyl ethers, an alcanol 11 and expediently its alkoxide 12 are brought into contact with 14 at 10–100° C., advantageously 20–80° C., for from 0.5 to 8 h, advantageously for 1 to 4 h. Instead of the alkoxide 12, it is also possible to use one of the bases mentioned above or an alkali metal hydroxide in the alcohol in question.

The molar amounts in which the alkoxide 12 or the base are employed are from 0.95 to 1.2, advantageously from 1.0 to 1.1, mol per mole of benzyl chloride 24.

The process is described in Houben-Weyl, 4th Edition, Volume 6/3, pp. 24–32.

To release the compounds 23, the starting materials 22 are treated with aqueous alkali (expediently from 0.95 to 1.2 mol, advantageously from 1.0 to 1.1 mol), at 20–120° C., advantageously 70–100° C., for 1 to 20 h, advantageously for 2 to 10 h.

All of the reaction steps described above can be carried out under atmospheric pressure or superatrhospheric pressure, continuously or batchwise.

The concentration of the starting materials in the solvent is from 0.1 to 5 mol/l, preferably from 0.2 to 2 mol/l.

Work-up of the reaction mixtures is generally carried out by methods known per se, for example by diluting the reaction solution with water, followed by isolation of the product by filtration, crystallization or solvent extraction, or by removal of the solvent and distillation, or partitioning of the residue in a mixture of water and a suitable organic solvent and work-up of the organic phase to afford the product.

Unless indicated otherwise, the solvents used for the above reactions are—depending on the temperature range—hydrocarbons, such as pentane, hexane, cyclopentane, cyclohexane, toluene, xylene, chlorinated hydrocarbons, such as methylene chloride, chloroform, 1,2-dichloroethane, 1,1,2,2-tetrachloroethane, chlorobenzene, 1,2-, 1,3- or 1,4-dichloro-benzene, ethers such as 1,4-dioxane, tetrahydrofuran, anisole, glycol ethers, such as dimethyl glycol ether, diethyl glycol ether, diethylene glycol dimethyl ether, esters, such as ethyl acetate, propyl acetate, methyl isobutyrate, isobutyl acetate, carboxamides, such as dimethylformamide, N-methylpyrrolidone, nitrohydrocarbons, such as nitrobenzene, ureas, such as tetraethylurea, tetrabutylurea, dimethylethyleneurea, dimethylpropyleneurea, sulfoxides, such as dimethyl sulfoxide, sulfones, such as dimethyl sulfone, diethyl sulfone, tetramethylene sulfone, nitrites, such as acetonitrile, propionitrile, butyronitrile or isobutyronitrile; water or else mixtures of individual solvents.

The aniline compounds can be obtained in good yields. They can also be prepared on a relatively large scale. Accordingly, they are particularly suitable for use as starting materials for preparing compounds of the formula I in which Q is appropriately substituted $Q_1$. The amine of the formula

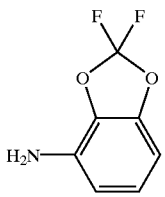

and its preparation are described in WO 93/24483 and EP 537 519 A.

Among the pyridine-2,3-dicarboxamides according to the invention, preference is given to those compounds in which the variables have the following meanings, in each case on their own or in combination:

Pyridine-2,3-dicarboxamides of the formula I as claimed in claim 1 where:

$R^1$ is halogen, CN, $NO_2$, $C_1$–$C_3$-alkyl, trifluoromethyl, $C_1$–$C_3$-alkoxy, $C_1$–$C_3$-haloalkoxy, $C_1$–$C_3$-alkylthio, trifluoromethylthio, difluoromethylthio, $C_1$–$C_3$-alkylsulfinyl, trifluoromethylsulfinyl, difluoromethylsulfinyl, $C_1$–$C_3$-alkylsulfonyl, trifluoromethylsulfonyl, difluoromethylsulfonyl, cyclopropyl, amino or methylamino; and Q, $R^2$ are as defined in claim 1;

$R^3$ is halogen, cyano, methyl, methoxy, difluoromethyl, trifluoromethyl, difluoromethoxy or trifluoromethoxy;

$R^4$ is hydrogen, $C_1$–$C_3$-alkyl, $C_1$–$C_3$-haloalkyl, $C_1$–$C_3$-alkoxy, saturated $C_3$–$C_7$-cycloalkyl, 3- to 6-membered saturated or unsaturated hetertocyclyl having 1 or 2 heteroatoms which are selected independently of one another from the group consisting of N, O and S;

$R^5$ is hydrogen;

$R^6$ is $C_1$–$C_6$-alkyl, $C_1$–$C_6$-haloalkyl, $C_1$–$C_6$-cyanoalkyl, $C_3$–$C_6$-cyclalkyl, $C_3$–$C_6$-cycloalkyl-$C_1$–$C_3$-alkyl, methyl-substituted $C_3$–$C_6$-cycloalkyl, $C_1$–$C_4$-alkoxy-$C_1$–$C_4$-alkyl, methylthio-$C_1$–$C_6$-alkyl, $C_3$–$C_6$-alkenyl, $C_3$–$C_6$-alkynyl or together with $R^5$ is a 5- or 6-membered heterocycle having 1 or 2 heteroatoms which are selected independently of one another from the group consisting of N and O, and which is unsubstituted or has 1 or 2 substituents selected independently of one another from the group consisting of halogen, $C_1$–$C_3$-alkyl or methoxy;

X is O;

m is 0;

n is 0, 1, 2 or 3;

o is 0, 1, 2, 3 or 4;

p is 0, 1, 2 or 3;

q is 0, 1, 2 or 3, where n=2 or 3, if Q=$Q_1$, and salts thereof.

Further preferred compounds are those of the formula I where:

A)

$R^1$ is $C_1$–$C_3$-alkyl, halogen, $NO_2$, amino, mono-$C_1$–$C_3$-alkylamino, $C_1$–$C_3$-alkoxy or CN;

Q is one of the radicals $Q_1$ to $Q_7$;

$R^2$ is $C_1$–$C_3$-alkyl, halogen, CN, carbamoyl, $NO_2$, formyl, $C_1$–$C_4$-alkylcarbonyl, $C_1$–$C_3$-alkoximinomethyl, $C_1$–$C_3$-haloalkoxy, $C_1$–$C_3$-alkoxy, $C_1$–$c_3$-haloalkyl, $C_1$–$C_3$-alkoxymethyl, $C_1$–$C_3$-alkoxycarbonyl, $C_1$–$C_3$-alkylthiocarbonyl, $C_3$–$C_4$-alkynyloxy, $C_1$–$C_3$-alkylthio, $C_1$–$C_3$-alkoxycarbonyl-$C_1$–$C_3$-alkoxy or $C_1$–$C_3$-alkylsulfonyl, $C_1$–$C_3$-haloalkylsulfonyl;

$R^3$ is $C_1$–$C_3$-alkyl or halogen;

$R^4$ is hydrogen, $C_1$–$C_3$-alkyl, $C_1$–$C_3$-haloalkyl, $C_3$–$C_6$-cycloalkyl or 5- or 6-membered saturated or unsaturated heterocyclyl having one oxygen heteroatom;

$R^5$ is hydrogen;

$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;

X is O or S;

m is 0;

n is 1 or 2;

o is 2 or 3;

p is 0, 1 or 2;

q is 0 or 1;

and salts thereof.

B)

Q is $Q_1$;

$R^2$ is halogen, CN, carbamoyl, $NO_2$, formyl, $C_1$–$C_3$-alkylcarbonyl, $C_1$–$C_3$-alkoximinomethyl, $C_1$–$C_3$-alkyl, $C_1$–$C_3$-haloalkyl, $C_1$–$C_3$-alkoxy, $C_1$–$C_3$-haloalkoxy, $C_1$–$C_3$-alkoxymethyl, $C_1$–$C_3$-alkoxycarbonyl, $C_1$–$C_3$-alkylthiocarbonyl or $C_1$–$C_3$-alkoxycarbonyl-$C_1$–$C_3$-alkoxy, and n is 2.

C)

$R^1$ is $C_1$–$C_3$-alkyl, halogen, $C_1$–$C_3$-alkoxy;

Q is $Q_1$;

$R^2$ is $C_1$–$C_3$-alkyl, halogen, CN, carbamoyl, $NO_2$, formyl, $C_1$–$C_3$-alkylcarbonyl, $C_1$–$C_3$-alkoximinomethyl, $C_1$–$C_3$-haloalkoxy, $C_1$–$C_3$-alkoxy, $C_1$–$C_3$-haloalkyl, $C_1$–$C_3$-alkoxymethyl, $C_1$–$C_3$-alkoxycarbonyl, $C_1$–$C_3$-alkylthiocarbonyl, $C_3$–$C_4$-alkynyloxy, $C_1$–$C_3$-alkylthio, $C_1$–$C_3$-alkoxycarbonyl-$C_1$–$C_3$-alkoxy or $C_1$–$C_3$-alkylsulfonyl, $C_1$–$C_3$-haloalkylsulfonyl;

$R^5$ is hydrogen;

$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;

m is 0;

n is 2;

o is 2 or 3;

and salts thereof.

D)

$R^1$ is $C_1$–$C_3$-alkyl;

Q is $Q_2$;

$R^3$ is $C_1$–$C_3$-alkyl or halogen;

$R^5$ is hydrogen;

$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;

m is 0;

n is 2;

p is 0, 1, or 2;

and salts thereof.

E)

$R^1$ is $C_1$–$C_3$-alkyl;

Q is Q3 or $Q_4$;

$R^3$ is $C_1$–$C_3$-alkyl or halogen;

$R^5$ is hydrogen;

$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;

m is 0;

n is 2;

p is 0 or 1;

and salts thereof.

F)

$R^1$ is $C_1$–$C_3$-alkyl;

Q is $Q_5$;

$R^4$ is hydrogen, $C_1$–$C_3$-alkyl, $C_1$–$C_3$-haloalkyl, $C_3$–$C_6$-cycloalkyl or 5- or 6-membered saturated or unsaturated heterocyclyl having one oxygen heteroatom;

$R^5$ is hydrogen;

$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;

X is O or S;

m is 0;

n is 1 or 2;

q is 0;

and salts thereof.

G)

$R^1$ is $C_1$–$C_3$-alkyl, halogen or $C_1$–$C_3$-alkoxy;

Q is $Q_1$, $Q_2$, $Q_3$, $Q_4$, $Q_5$, $Q_6$ or $Q_7$;

$R^2$ is $C_1$–$C_3$-alkyl, $C_1$–$C_3$-haloalkyl, $C_1$–$C_3$-alkoxy, $C_1$–$C_3$-alkoxycarbonyl, $C_1$–$C_3$-alkylthiocarbonyl, $C_1$–$C_3$-alkoxymethyl, $C_1$–$C_3$-alkylthio, $C_1$–$C_3$-alkylsulfonyl, halogen or CN, formyl or $C_1$–$C_3$-alkoximinomethyl;

$R^5$ is hydrogen;

$R^6$ is $C_1$–$C_6$-alkyl or $C_3$–$C_6$-cycloalkyl;

m is 0;

n is 1 or 2;

o is 0, 1 or 2;

and salts thereof.

H)

$R^1$ is halogen, CN, $NO_2$, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl, $C_1$–$C_3$-haloalkylsulfinyl, $C_3$–$C_6$-cycloalkyl, $C_3$–$C_6$-cycloalkyl-$C_1$–$C_3$-alkyl, $C_2$–$C_4$-alkenyl, $C_2$–$C_4$-haloalkenyl, $C_2$–$C_4$-alkynyl, $C_3$–$C_4$-haloalkynyl, amino, $C_1$–$C_3$-monoalkylamino or $C_1$–$C_3$-alkylcarbonyl;

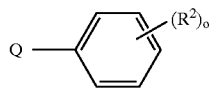

o is 1, 2, 3, 4 or 5;

$R^2$ is $C_1$–$C_3$-alkyl, halogen, $C_1$–$C_3$-haloalkyl, $C_1$–$C_3$-alkoxy, $C_1$–$C_3$-haloalkoxy, CN, $NO_2$, $C_1$–$C_3$-alkoxycarbonyl, $C_1$–$C_3$-alkoxycarbonyl-$C_1$–$C_3$-alkoxy, formyl, carbamoyl, $C_1$–$C_4$-alkylcarbonyl, $C_1$–$C_3$-alkylthiocarbonyl, $C_1$–$C_3$-alkylcarbamoyl, $C_1$–$C_3$-alkoxymethyl, $C_1$–$C_3$-alkoxy-$C_1$–$C_3$-alkyl, $C_1$–$C_4$-alkoximinomethyl, $C_3$–$C_4$-alkenyloxy, $C_3$–$C_4$-haloalkenyloxy, $C_3$–$C_4$-alkynyloxy, $C_3$–$C_4$-haloalkynyloxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl or $C_1$–$C_3$-haloalkylsulfonyl, where at least one radical $R^2$ is formyl, carbamoyl, $C_1$–$C_4$-alkylcarbonyl, $C_1$–$C_3$-alkylthiocarbonyl, $C_1$–$C_3$-alkylcarbamoyl, $C_1$–$C_3$-alkoxymethyl, $C_1$–$C_3$-alkoxy-$C_1$–$C_3$-alkyl, $C_1$–$C_4$-alkoximinomethyl, $C_3$–$C_4$-alkenyloxy, $C_3$–$C_4$-haloalkenyloxy, $C_3$–$C_4$-alkynyloxy, $C_3$–$C_4$-haloalkynyloxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl or $C_1$–$C_3$-haloalkylsulfonyl, or if o=2, the substituent combinations 2-cyano-3-halogen, 2,3-di-$C_1$–$C_3$-alkyl, 2-halo-3-trifluoromethyl, 2-nitro-3-trifluoromethyl, 2-cyano-3-$C_1$–$C_3$-alkyl, 2-cyano-3-$C_1$–$C_3$-alkoxy, 2-cyano-3-difluoromethoxy, 2-cyano-3-trifluoromethyl, 2-halo-3-$C_1$–$C_3$-alkyl, 2-$C_1$–$C_3$-alkyl-3-$C_1$–$C_3$-alkoxy, 2-$C_1$–$C_3$-alkoxy-3-halo, 2-[$C_1$–$C_3$-alkoxycarbonyl]-3-halo, 2-[$C_1$–$C_3$-alkoxycarbonyl]-3-$C_1$–$C_3$-alkyl, 2-trifluoromethyl-3-$C_1$–$C_3$-alkyl, 2-trifluoromethyl-3-chloro or 2-trifluoromethyl-3-bromo; or if o=3, the substituent combinations 2-($C_1$–$C_3$-alkyl)-3-halo-6-($C_1$–$C_3$-alkylcarbamoyl), 2-($C_1$–$C_3$-alkoxycarbonyl)-3,6-di-($C_1$–$C_3$-alkyl), 2-cyano-3-halo-6-($C_1$–$C_3$-alkyl), 2-carbamoyl-3-chloro-6-($C_1$–$C_3$-alkyl), 2-($C_1$–$C_3$-alkoxycarbonyl)-3-halo-6-($C_1$–$C_3$-alkyl), 2-($C_1$–$C_3$-alkoxycarbonyl)-3,6-dihalo, 2-cyano-3-($C_1$–$C_3$-alkyl)-6-halo, 2-($C_1$–$C_3$-alkoxycarbonyl)-3-($C_1$–$C_3$-alkyl)-6-halo, 2-($C_1$–$C_3$-alkyl)-3-halo-6-($C_1$–$C_3$-alkoxycarbonyl), 2-cyano-3,6-dihalo, 2-cyano-3,6-di-($C_1$–$C_3$-alkyl), 2-methyl-3-chloro-6-cyano, 2-chloro-3-methyl-6-cyano, 2-chloro-3-methyl-6-($C_1$–$C_3$-alkoxycarbonyl), 2-($C_1$–$C_3$-alkoxycarbonyl)-3-chloro-6-cyano, 2-cyano-3-chloro-6-($C_1$–$C_3$-alkoxycarbonyl), 2-ethyl-3-chloro-6-cyano, 2-($C_1$–$C_3$-alkoxymethyl)-3-halo-6-($C_1$–$C_3$-alkyl), 2-($C_1$–$C_3$-alkyl)-3-halo-6-($C_1$–$C_3$-alkoxymethyl);

$R^5$ is hydrogen, $C_1$–$C_3$-alkyl, OH or $C_1$–$C_4$-alkoxy;

$R^6$ is hydrogen, $C_1$–$C_6$-alkyl, $C_1$–$C_6$-haloalkyl, $C_1$–$C_6$-cyanoalkyl, $C_3$–$C_6$-cycloalkyl, $C_3$–$C_6$-cycloalkenyl, $C_3$–$C_6$-cycloalkyl-$C_1$–$C_3$-alkyl, $C_3$–$C_6$-cycloalkyl having 1 or 2 substituents which are selected independently of one another from the group consisting of halogen and $C_1$–$C_3$-alkyl, is $C_3$–$C_6$-cycloalkoxy-$C_1$–$C_3$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkoxycarbonyl-$C_1$–$C_6$-alkyl, $C_3$–$C_6$-alkenyl, $C_3$–$C_6$-alkynyl, amino, $C_1$–$C_4$-monoalkylamino, di-$C_1$–$C_4$-alkylamino or $R^6$ together with $R^5$ is a 5- or 6-membered heterocycle having 1, 2 or 3 heteroatoms which are selected independently of one another from the group consisting of N, O and S, and which is unsubstituted or has 1 or 2 substituents selected independently of one another from the group consisting of halogen, $C_1$–$C_3$-alkyl, $C_1$–$C_3$-alkoxy and $C_1$–$C_3$-haloalkyl;

m is 0 or 1;

n is 0, 1, 2 or 3;

o is 0, 1, 2, 3, 4 or 5;

and salts thereof.

$R^1$ is particularly preferably halogen, in particular chlorine, $C_1$–$C_3$-alkyl, in particular methyl, and/or $C_1$–$C_3$-alkoxy, in particular methoxy.

n is particularly preferably 2. In this case, the radical $R^1$ is located in particular in the 5 and 6 position. In the case of the substituent combinations mentioned under H), n is preferably 1.

$R^2$ is particularly preferably CN, $C_1$–$C_3$-alkylcarbonyl, $C_1$–$C_3$-alkoxycarbonyl, $C(O)NH_2$, $CH_3$, $CF_3$ and/or halogen, in particular Cl. o is preferably 2, in which case $R^2$ is located in particular in the 2- and/or 3-position.

If o=2, one of the radicals $R^2$ is preferably CN, carbamoyl, $C_1$–$C_3$-alkylcarbonyl, $C_1$–$C_3$-alkoxycarbonyl, $C_1$–$C_3$-alkoximino-methyl, $C_1$–$C_3$-alkoxymethyl or formyl in the 2-position and the other radical is halogen, $C_1$–$C_3$-alkyl or difluoromethoxy in the 3-position.

$R^2$ is furthermore preferably $C_3$–$C_4$-alkenyloxy, $C_3$–$C_4$-haloalkenyloxy, $C_3$–$C_4$-alkynyloxy, $C_3$–$C_4$-haloalkynyloxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl or $C_1$–$C_3$-haloalkylsulfonyl and n is 2 or $R^2$ is 2-CN-3-halo (in particular Cl), 2-halo (in particular Cl)-3-$CF_3$ or 2-$NO_2$-3-$CF_3$ (i.e. o=2) and n=1.

If o=2, the two radicals $R^2$ are particularly preferably 2-CN-3-Cl; 2,3-dimethyl; 2-Cl-3-$CF_3$; 2-$NO_2$-3-$CF_3$; 2-CN-3-$CH_3$; 2-CN-3-$OCH_3$; 2-CN-3-$OCHF_2$; 2-CN-3-$CF_3$; 2-Cl-3-$CH_3$; 2-$CH_3$-3-$OCH_3$; 2-$OCH_3$-3Cl; 2-$CH_3CO$-3-Cl; 2-$CH_3O$—(CO)-3-Cl; 2-$CH_3O$—(CO)-3-$CH_3$; 2-$CF_3$-3$CH_3$; 2-$CF_3$-3-Cl; 2-$CF_3$-3Br; 2-$CH_3O$—N=CH-3-Cl; 2-$CH_3O$—(CO)-3-Br; 3-chloro-2-methoxymethoxy; 3-Br-2-methoxymethyl.

In another group of preferred compounds, n is 2, particularly preferably 1, and o is 3. Preferably, one of the radicals $R^2$ is $C_1$–$C_3$-alkoxycarbonyl, $C_1$–$C_3$-alkoxymethyl, carbamoyl or cyano, preferably in the 2-position. The other radicals $R^2$ are preferably halogen and/or $C_1$–$C_3$-alkyl, in particular in the 3- and/or 6-position. However, it is also possible for $C_1$–$C_3$-alkoxymethyl, cyano, carbamoyl or $C_1$–$C_3$-alkoxycarbonyl to be one of the radicals $R^2$ in the 6-position, the other two radicals $R^2$ being $C_1$–$C_3$-alkyl and/or halogen in the 2- and/or 3-position.

Particular preference is given to the following combinations of substituents: 2-$CH_3$-3-Cl-6-$CH_3O$—CO; 2-$CH_3O$—CO-3,6-$(CH_3)_2$; 2-CN-3-Cl-6-$CH_3$; 2-CO—$NH_2$-3-Cl-6-$CH_3$; 2-$CH_3O$—CO-3-Cl-6-$CH_3$; 2-$CH_3O$—CO-3,6-$Cl_2$; 2-CN-3-$CH_3$-6-Cl; 2-$CH_3O$—CO-3-$CH_3$-6-Cl; 2-$CH_3$-3-Cl-6-$CH_3O$—CO; 2-CN-3,6-$Cl_2$; 2-Cl-3-$CH_3$-6-CN; 2-Cl-3-$CH_3$-6-$CH_3O$—CO; 2-$CH_3$-3-Cl-6-CN; 2-$CH_3O$(CO)-3-Cl-6-CN; 2-CN-3-Cl-6-$CH_3O$(CO); 2,3,6-$(CH_3)_3$; 2-$CH_3O$—(CO)-3-Cl-6-ethyl; 2-CN-3,6-$(CH_3)_2$; 2-C(O)$NH_2$-3-Cl-6-ethyl; 2-$CH_3O$(CO)-3-Br-6-$CH_3$; 2-$CH_3O$(CO)-3-Br-6-ethyl; 2-ethyl-3-Cl-6-$CH_3O$—(CO); 2-Cl-3-$CH_3$-6-$CH_3O$—(CO); 2-Br-3-Cl-6-$CH_3O$—(CO); 2-$CH_3$-3-Cl-6-CN; 2-ethyl-3-Cl-6-CN; 2-Cl-3-$CH_3$-6-CN; 2,3-$(Cl_2)$-6-CN; 2,3-$(CH_3)_2$-6-CN; 2,6-[$CH_3O$—(CO)]$_2$-3-Cl; 2-$CH_3O$(CO)-3-Cl-6-$CH_3O$; 2-CN-3-Cl-6-$CH_3O$; 2-$CH_3OCH_2$-3-Cl-6-$CH_3$; 2-$CH_3O$—$CH_2$-3-Cl-6-ethyl; 2-$CH_3OCH_2$-3-Br-6-$CH_3$, 2-$CH_3$-3-Cl-6-$CH_3OCH_2$, 2-ethyl-3-Cl-6-$CH_3OCH_2$.

Particular preference is given to the compounds listed in Tables 1 and 2 below:

TABLE 1

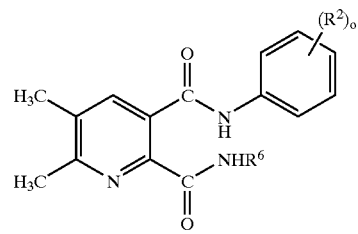

Ia

| | $(R^2)_o$ | $R^6$ |
|---|---|---|
| Ia.1 | 2-$CH_3$-3-Cl | n-$C_3H_7$ |
| Ia.2 | 2-$CH_3$-3-Cl | iso-$C_3H_7$ |
| Ia.3 | 2-$CH_3$-3-Cl | n-$C_4H_9$ |
| Ia.4 | 2-$CH_3$-3-Cl | iso-$C_4H_9$ |
| Ia.5 | 2-$CH_3$-3-Cl | sec-$C_4H_9$ |
| Ia.6 | 2-$CH_3$-3-Cl | 3-methylbutyl |
| Ia.7 | 2-$CH_3$-3-Cl | n-$C_5H_{11}$ |
| Ia.8 | 2-$CH_3$-3-Cl | $CH_2$—$C(CH_3)$=$CH_2$ |
| Ia.9 | 2-$CH_3$-3-Cl | $CH_2$-c-$C_3H_5$ |
| Ia.10 | 2-$CH_3$-3-Cl | 1-ethylcyclopropyl |
| Ia.11 | 2-$CH_3$-3-Cl | c-$C_6H_{11}$ |
| Ia.12 | 2-$CH_3$-3-Br | n-$C_3H_7$ |
| Ia.13 | 2-$CH_3$-3-Br | iso-$C_3H_7$ |
| Ia.14 | 2-$CH_3$-3-Br | n-$C_4H_9$ |
| Ia.15 | 2-$CH_3$-3-Br | iso-$C_4H_9$ |
| Ia.16 | 2-$CH_3$-3-Br | sec-$C_4H_9$ |
| Ia.17 | 2-$CH_3$-3-Br | 3-methylbutyl |
| Ia.18 | 2-$CH_3$-3-Br | n-$C_5H_{11}$ |
| Ia.19 | 2-$CH_3$-3-Br | $CH_2$—$C(CH_3)$=$CH_2$ |
| Ia.20 | 2-$CH_3$-3-Br | $CH_2$-c-$C_3H_5$ |
| Ia.21 | 2-$CH_3$-3-Br | 1-ethylcyclopropyl |
| Ia.22 | 2-$CH_3$-3-Br | c-$C_6H_{11}$ |
| Ia.23 | 2-CN-3-$OCHF_2$ | n-$C_3H_7$ |
| Ia.24 | 2-CN-3-$OCHF_2$ | iso-$C_3H_7$ |
| Ia.25 | 2-CN-3-$OCHF_2$ | n-$C_4H_9$ |
| Ia.26 | 2-CN-3-$OCHF_2$ | iso-$C_4H_9$ |
| Ia.27 | 2-CN-3-$OCHF_2$ | sec-$C_4H_9$ |
| Ia.28 | 2-CN-3-$OCHF_2$ | 3-methylbutyl |
| Ia.29 | 2-CN-3-$OCHF_2$ | n-$C_5H_{11}$ |
| Ia.30 | 2-CN-3-$OCHF_2$ | $CH_2$—$C(CH_3)$=$CH_2$ |
| Ia.31 | 2-CN-3-$OCHF_2$ | $CH_2$-c-$C_3H_5$ |
| Ia.32 | 2-CN-3-$OCHF_2$ | 1-ethylcyclopropyl |
| Ia.33 | 2-CN-3-$OCHF_2$ | c-$C_6H_{11}$ |
| Ia.34 | 2-$CH_3$-5-Cl | n-$C_3H_7$ |
| Ia.35 | 2-$CH_3$-5-Cl | iso-$C_3H_7$ |
| Ia.36 | 2-$CH_3$-5-Cl | n-$C_4H_9$ |
| Ia.37 | 2-$CH_3$-5-Cl | iso-$C_4H_9$ |
| Ia.38 | 2-$CH_3$-5-Cl | sec-$C_4H_9$ |
| Ia.39 | 2-$CH_3$-5-Cl | 3-methylbutyl |
| Ia.40 | 2-$CH_3$-5-Cl | n-$C_5H_{11}$ |
| Ia.41 | 2-$CH_3$-5-Cl | $CH_2$—$C(CH_3)$=$CH_2$ |
| Ia.42 | 2-$CH_3$-5-Cl | $CH_2$-c-$C_3H_5$ |
| Ia.43 | 2-$CH_3$-5-Cl | 1-ethylcyclopropyl |
| Ia.44 | 2-$CH_3$-5-Cl | c-$C_6H_{11}$ |
| Ia.45 | 2,3-$Cl_2$ | n-$C_3H_7$ |
| Ia.46 | 2,3-$Cl_2$ | iso-$C_3H_7$ |
| Ia.47 | 2,3-$Cl_2$ | n-$C_4H_9$ |
| Ia.48 | 2,3-$Cl_2$ | iso-$C_4H_9$ |
| Ia.49 | 2,3-$Cl_2$ | sec-$C_4H_9$ |
| Ia.50 | 2,3-$Cl_2$ | 3-methylbutyl |
| Ia.51 | 2,3-$Cl_2$ | n-$C_5H_{11}$ |
| Ia.52 | 2,3-$Cl_2$ | $CH_2$—$C(CH_3)$=$CH_2$ |
| Ia.53 | 2,3-$Cl_2$ | $CH_2$-c-$C_3H_5$ |
| Ia.54 | 2,3-$Cl_2$ | 1-ethylcyclopropyl |
| Ia.55 | 2,3-$Cl_2$ | c-$C_6H_{11}$ |
| Ia.56 | 2,6-$(CH_3)_2$ | n-$C_3H_7$ |
| Ia.57 | 2,6-$(CH_3)_2$ | iso-$C_3H_7$ |
| Ia.58 | 2,6-$(CH_3)_2$ | n-$C_4H_9$ |
| Ia.59 | 2,6-$(CH_3)_2$ | iso-$C_4H_9$ |
| Ia.60 | 2,6-$(CH_3)_2$ | sec-$C_4H_9$ |
| Ia.61 | 2,6-$(CH_3)_2$ | 3-methylbutyl |

TABLE 1-continued

Ia

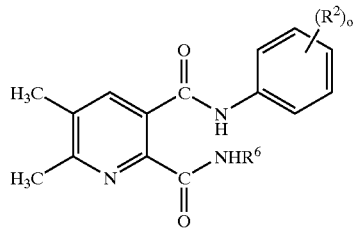

| | (R²)ₒ | R⁶ |
|---|---|---|
| Ia.62 | 2,6-(CH₃)₂ | n-C₅H₁₁ |
| Ia.63 | 2,6-(CH₃)₂ | CH₂—C(CH₃)=CH₂ |
| Ia.64 | 2,6-(CH₃)₂ | CH₂-c-C₃H₅ |
| Ia.65 | 2,6-(CH₃)₂ | 1-ethylcyclopropyl |
| Ia.66 | 2,6-(CH₃)₂ | c-C₆H₁₁ |
| Ia.67 | 2,3-(CH₃)₂ | n-C₃H₇ |
| Ia.68 | 2,3-(CH₃)₂ | iso-C₃H₇ |
| Ia.69 | 2,3-(CH₃)₂ | n-C₄H₉ |
| Ia.70 | 2,3-(CH₃)₂ | iso-C₄H₉ |
| Ia.71 | 2,3-(CH₃)₂ | sec-C₄H₉ |
| Ia.72 | 2,3-(CH₃)₂ | 3-methylbutyl |
| Ia.73 | 2,3-(CH₃)₂ | n-C₅H₁₁ |
| Ia.74 | 2,3-(CH₃)₂ | CH₂—C(CH₃)=CH₂ |
| Ia.75 | 2,3-(CH₃)₂ | CH₂-c-C₃H₅ |
| Ia.76 | 2,3-(CH₃)₂ | 1-ethylcyclopropyl |
| Ia.77 | 2,3-(CH₃)₂ | c-C₆H₁₁ |
| Ia.78 | 2,6-(C₂H₅)₂ | n-C₃H₇ |
| Ia.79 | 2,6-(C₂H₅)₂ | iso-C₃H₇ |
| Ia.80 | 2,6-(C₂H₅)₂ | n-C₄H₉ |
| Ia.81 | 2,6-(C₂H₅)₂ | iso-C₄H₉ |
| Ia.82 | 2,6-(C₂H₅)₂ | sec-C₄H₉ |
| Ia.83 | 2,6-(C₂H₅)₂ | 3-methylbutyl |
| Ia.84 | 2,6-(C₂H₅)₂ | n-C₅H₁₁ |
| Ia.85 | 2,6-(C₂H₅)₂ | CH₂—C(CH₃)=CH₂ |
| Ia.86 | 2,6-(C₂H₅)₂ | CH₂-c-C₃H₅ |
| Ia.87 | 2,6-(C₂H₅)₂ | 1-ethylcyclopropyl |
| Ia.88 | 2,6-(C₂H₅)₂ | c-C₆H₁₁ |
| Ia.89 | 2-CH₃O-5-CH₃ | n-C₃H₇ |
| Ia.90 | 2-CH₃O-5-CH₃ | iso-C₃H₇ |
| Ia.91 | 2-CH₃O-5-CH₃ | n-C₄H₉ |
| Ia.92 | 2-CH₃O-5-CH₃ | iso-C₄H₉ |
| Ia.93 | 2-CH₃O-5-CH₃ | sec-C₄H₉ |
| Ia.94 | 2-CH₃O-5-CH₃ | 3-methylbutyl |
| Ia.95 | 2-CH₃O-5-CH₃ | n-C₅H₁₁ |
| Ia.96 | 2-CH₃O-5-CH₃ | CH₂—C(CH₃)=CH₂ |
| Ia.97 | 2-CH₃O-5-CH₃ | CH₂-c-C₃H₅ |
| Ia.98 | 2-CH₃O-5-CH₃ | 1-ethylcyclopropyl |
| Ia.99 | 2-CH₃O-5-CH₃ | c-C₆H₁₁ |
| Ia.100 | 2-CH₃-3-CN | n-C₃H₇ |
| Ia.101 | 2-CH₃-3-CN | iso-C₃H₇ |
| Ia.102 | 2-CH₃-3-CN | n-C₄H₉ |
| Ia.103 | 2-CH₃-3-CN | iso-C₄H₉ |
| Ia.104 | 2-CH₃-3-CN | sec-C₄H₉ |
| Ia.105 | 2-CH₃-3-CN | 3-methylbutyl |
| Ia.106 | 2-CH₃-3-CN | n-C₅H₁₁ |
| Ia.107 | 2-CH₃-3-CN | CH₂—C(CH₃)=CH₂ |
| Ia.108 | 2-CH₃-3-CN | CH₂-c-C₃H₅ |
| Ia.109 | 2-CH₃-3-CN | 1-ethylcyclopropyl |
| Ia.110 | 2-CH₃-3-CN | c-C₆H₁₁ |
| Ia.111 | 2-CH₃-3-OCHF₂ | n-C₃H₇ |
| Ia.112 | 2-CH₃-3-OCHF₂ | iso-C₃H₇ |
| Ia.113 | 2-CH₃-3-OCHF₂ | n-C₄H₉ |
| Ia.114 | 2-CH₃-3-OCHF₂ | iso-C₄H₉ |
| Ia.115 | 2-CH₃-3-OCHF₂ | sec-C₄H₉ |
| Ia.116 | 2-CH₃-3-OCHF₂ | 3-methylbutyl |
| Ia.117 | 2-CH₃-3-OCHF₂ | n-C₅H₁₁ |
| Ia.118 | 2-CH₃-3-OCHF₂ | CH₂—C(CH₃)=CH₂ |
| Ia.119 | 2-CH₃-3-OCHF₂ | CH₂-c-C₃H₅ |
| Ia.120 | 2-CH₃-3-OCHF₂ | 1-ethylcyclopropyl |
| Ia.121 | 2-CH₃-3-OCHF₂ | c-C₆H₁₁ |
| Ia.122 | 2,5-(CH₃)₂ | n-C₃H₇ |
| Ia.123 | 2,5-(CH₃)₂ | iso-C₃H₇ |
| Ia.124 | 2,5-(CH₃)₂ | n-C₄H₉ |
| Ia.125 | 2,5-(CH₃)₂ | iso-C₄H₉ |

TABLE 1-continued

Ia

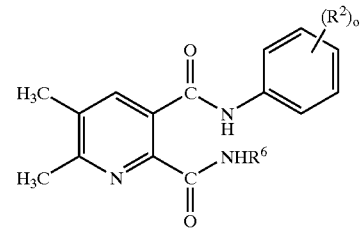

| | (R²)ₒ | R⁶ |
|---|---|---|
| Ia.126 | 2,5-(CH₃)₂ | sec-C₄H₉ |
| Ia.127 | 2,5-(CH₃)₂ | 3-methylbutyl |
| Ia.128 | 2,5-(CH₃)₂ | n-C₅H₁₁ |
| Ia.129 | 2,5-(CH₃)₂ | CH₂—C(CH₃)=CH₂ |
| Ia.130 | 2,5-(CH₃)₂ | CH₂-c-C₃H₅ |
| Ia.131 | 2,5-(CH₃)₂ | 1-ethylcyclopropyl |
| Ia.132 | 2,5-(CH₃)₂ | c-C₆H₁₁ |
| Ia.133 | 2-CH₃-3-CF₃ | n-C₃H₇ |
| Ia.134 | 2-CH₃-3-CF₃ | iso-C₃H₇ |
| Ia.135 | 2-CH₃-3-CF₃ | n-C₄H₉ |
| Ia.136 | 2-CH₃-3-CF₃ | iso-C₄H₉ |
| Ia.137 | 2-CH₃-3-CF₃ | sec-C₄H₉ |
| Ia.138 | 2-CH₃-3-CF₃ | 3-methylbutyl |
| Ia.139 | 2-CH₃-3-CF₃ | n-C₅H₁₁ |
| Ia.140 | 2-CH₃-3-CF₃ | CH₂—C(CH₃)=CH₂ |
| Ia.141 | 2-CH₃-3-CF₃ | CH₂-c-C₃H₅ |
| Ia.142 | 2-CH₃-3-CF₃ | 1-ethylcyclopropyl |
| Ia.143 | 2-CH₃-3-CF₃ | c-C₆H₁₁ |
| Ia.144 | 2,6-(C₂H₅)₂-3-Cl | n-C₃H₇ |
| Ia.145 | 2,6-(C₂H₅)₂-3-Cl | iso-C₃H₇ |
| Ia.146 | 2,6-(C₂H₅)₂-3-Cl | n-C₄H₉ |
| Ia.147 | 2,6-(C₂H₅)₂-3-Cl | iso-C₄H₉ |
| Ia.148 | 2,6-(C₂H₅)₂-3-Cl | sec-C₄H₉ |
| Ia.149 | 2,6-(C₂H₅)₂-3-Cl | 3-methylbutyl |
| Ia.150 | 2,6-(C₂H₅)₂-3-Cl | n-C₅H₁₁ |
| Ia.151 | 2,6-(C₂H₅)₂-3-Cl | CH₂—C(CH₃)=CH₂ |
| Ia.152 | 2,6-(C₂H₅)₂-3-Cl | CH₂-c-C₃H₅ |
| Ia.153 | 2,6-(C₂H₅)₂-3-Cl | 1-ethylcyclopropyl |
| Ia.154 | 2,6-(C₂H₅)₂-3-Cl | c-C₆H₁₁ |
| Ia.155 | 2-CH₃-3-CO₂CH₃ | n-C₃H₇ |
| Ia.156 | 2-CH₃-3-CO₂CH₃ | iso-C₃H₇ |
| Ia.157 | 2-CH₃-3-CO₂CH₃ | n-C₄H₉ |
| Ia.158 | 2-CH₃-3-CO₂CH₃ | iso-C₄H₉ |
| Ia.159 | 2-CH₃-3-CO₂CH₃ | sec-C₄H₉ |
| Ia.160 | 2-CH₃-3-CO₂CH₃ | 3-methylbutyl |
| Ia.161 | 2-CH₃-3-CO₂CH₃ | n-C₅H₁₁ |
| Ia.162 | 2-CH₃-3-CO₂CH₃ | CH₂—C(CH₃)=CH₂ |
| Ia.163 | 2-CH₃-3-CO₂CH₃ | CH₂-c-C₃H₅ |
| Ia.164 | 2-CH₃-3-CO₂CH₃ | 1-ethylcyclopropyl |
| Ia.165 | 2-CH₃-3-CO₂CH₃ | c-C₆H₁₁ |
| Ia.166 | 2-CH₃-3-NO₂ | n-C₃H₇ |
| Ia.167 | 2-CH₃-3-NO₂ | iso-C₃H₇ |
| Ia.168 | 2-CH₃-3-NO₂ | n-C₄H₉ |
| Ia.169 | 2-CH₃-3-NO₂ | iso-C₄H₉ |
| Ia.170 | 2-CH₃-3-NO₂ | sec-C₄H₉ |
| Ia.171 | 2-CH₃-3-NO₂ | 3-methylbutyl |
| Ia.172 | 2-CH₃-3-NO₂ | n-C₅H₁₁ |
| Ia.173 | 2-CH₃-3-NO₂ | CH₂—C(CH₃)=CH₂ |
| Ia.174 | 2-CH₃-3-NO₂ | CH₂-c-C₃H₅ |
| Ia.175 | 2-CH₃-3-NO₂ | 1-ethylcyclopropyl |
| Ia.176 | 2-CH₃-3-NO₂ | c-C₆H₁₁ |
| Ia.177 | 2,4-Cl₂-5-OCH₂C≡CH | n-C₃H₇ |
| Ia.178 | 2,4-Cl₂-5-OCH₂C≡CH | iso-C₃H₇ |
| Ia.179 | 2,4-Cl₂-5-OCH₂C≡CH | n-C₄H₉ |
| Ia.180 | 2,4-Cl₂-5-OCH₂C≡CH | iso-C₄H₉ |
| Ia.181 | 2,4-Cl₂-5-OCH₂C≡CH | sec-C₄H₉ |
| Ia.182 | 2,4-Cl₂-5-OCH₂C≡CH | 3-methylbutyl |
| Ia.183 | 2,4-Cl₂-5-OCH₂C≡CH | n-C₅H₁₁ |
| Ia.184 | 2,4-Cl₂-5-OCH₂C≡CH | CH₂—C(CH₃)=CH₂ |
| Ia.185 | 2,4-Cl₂-5-OCH₂C≡CH | CH₂-c-C₃H₅ |
| Ia.186 | 2,4-Cl₂-5-OCH₂C≡CH | 1-ethylcyclopropyl |
| Ia.187 | 2,4-Cl₂-5-OCH₂C≡CH | c-C₆H₁₁ |
| Ia.188 | 2-F-4-Cl-5-OCH₂≡CH | n-C₃H₇ |
| Ia.189 | 2-F-4-Cl-5-OCH₂≡CH | iso-C₃H₇ |

TABLE 1-continued

|  | (R²)ₒ | R⁶ |
|---|---|---|
| Ia.190 | 2-F-4-Cl-5-OCH₂=CH | n-C₄H₉ |
| Ia.191 | 2-F-4-Cl-5-OCH₂=CH | iso-C₄H₉ |
| Ia.192 | 2-F-4-Cl-5-OCH₂=CH | sec-C₄H₉ |
| Ia.193 | 2-F-4-Cl-5-OCH₂=CH | 3-methylbutyl |
| Ia.194 | 2-F-4-Cl-5-OCH₂=CH | n-C₅H₁₁ |
| Ia.195 | 2-F-4-Cl-5-OCH₂=CH | CH₂—C(CH₃)=CH₂ |
| Ia.196 | 2-F-4-Cl-5-OCH₂=CH | CH₂-c-C₃H₅ |
| Ia.197 | 2-F-4-Cl-5-OCH₂=CH | 1-ethylcyclopropyl |
| Ia.198 | 2-F-4-Cl-5-OCH₂=CH | c-C₆H₁₁ |
| Ia.199 | 2-F-3-CF₃ | n-C₃H₇ |
| Ia.200 | 2-F-3-CF₃ | iso-C₃H₇ |
| Ia.201 | 2-F-3-CF₃ | n-C₄H₉ |
| Ia.202 | 2-F-3-CF₃ | iso-C₄H₉ |
| Ia.203 | 2-F-3-CF₃ | sec-C₄H₉ |
| Ia.204 | 2-F-3-CF₃ | 3-methylbutyl |
| Ia.205 | 2-F-3-CF₃ | n-C₅H₁₁ |
| Ia.206 | 2-F-3-CF₃ | CH₂—C(CH₃)=CH₂ |
| Ia.207 | 2-F-3-CF₃ | CH₂-c-C₃H₅ |
| Ia.208 | 2-F-3-CF₃ | 1-ethylcyclopropyl |
| Ia.209 | 2-F-3-CF₃ | c-C₆H₁₁ |
| Ia.210 | 2-CH₃-3-F-4-OCH₃ | n-C₃H₇ |
| Ia.211 | 2-CH₃-3-F-4-OCH₃ | iso-C₃H₇ |
| Ia.212 | 2-CH₃-3-F-4-OCH₃ | n-C₄H₉ |
| Ia.213 | 2-CH₃-3-F-4-OCH₃ | iso-C₄H₉ |
| Ia.214 | 2-CH₃-3-F-4-OCH₃ | sec-C₄H₉ |
| Ia.215 | 2-CH₃-3-F-4-OCH₃ | 3-methylbutyl |
| Ia.216 | 2-CH₃-3-F-4-OCH₃ | n-C₅H₁₁ |
| Ia.217 | 2-CH₃-3-F-4-OCH₃ | CH₂—C(CH₃)=CH₂ |
| Ia.218 | 2-CH₃-3-F-4-OCH₃ | CH₂-c-C₃H₅ |
| Ia.219 | 2-CH₃-3-F-4-OCH₃ | 1-ethylcyclopropyl |
| Ia.220 | 2-CH₃-3-F-4-OCH₃ | c-C₆H₁₁ |
| Ia.221 | 2-CN-3-Cl | n-C₃H₇ |
| Ia.222 | 2-CN-3-Cl | iso-C₃H₇ |
| Ia.223 | 2-CN-3-Cl | n-C₄H₉ |
| Ia.224 | 2-CN-3-Cl | iso-C₄H₉ |
| Ia.225 | 2-CN-3-Cl | sec-C₄H₉ |
| Ia.226 | 2-CN-3-Cl | 3-methylbutyl |
| Ia.227 | 2-CN-3-Cl | n-C₅H₁₁ |
| Ia.228 | 2-CN-3-Cl | CH₂—C(CH₃)=CH₂ |
| Ia.229 | 2-CN-3-Cl | CH₂-c-C₃H₅ |
| Ia.230 | 2-CN-3-Cl | 1-ethylcyclopropyl |
| Ia.231 | 2-CN-3-Cl | c-C₆H₁₁ |
| Ia.232 | 2-CN-3-Br | n-C₃H₇ |
| Ia.233 | 2-CN-3-Br | iso-C₃H₇ |
| Ia.234 | 2-CN-3-Br | n-C₄H₉ |
| Ia.235 | 2-CN-3-Br | iso-C₄H₉ |
| Ia.236 | 2-CN-3-Br | sec-C₄H₉ |
| Ia.237 | 2-CN-3-Br | 3-methylbutyl |
| Ia.238 | 2-CN-3-Br | n-C₅H₁₁ |
| Ia.239 | 2-CN-3-Br | CH₂—C(CH₃)=CH₂ |
| Ia.240 | 2-CN-3-Br | CH₂-c-C₃H₅ |
| Ia.241 | 2-CN-3-Br | 1-ethylcyclopropyl |
| Ia.242 | 2-CN-3-Br | c-C₆H₁₁ |
| Ia.243 | 2-CN-3-F | n-C₃H₇ |
| Ia.244 | 2-CN-3-F | iso-C₃H₇ |
| Ia.245 | 2-CN-3-F | n-C₄H₉ |
| Ia.246 | 2-CN-3-F | iso-C₄H₉ |
| Ia.247 | 2-CN-3-F | sec-C₄H₉ |
| Ia.248 | 2-CN-3-F | 3-methylbutyl |
| Ia.249 | 2-CN-3-F | n-C₅H₁₁ |
| Ia.250 | 2-CN-3-F | CH₂—C(CH₃)=CH₂ |
| Ia.251 | 2-CN-3-F | CH₂-c-C₃H₅ |
| Ia.252 | 2-CN-3-F | 1-ethylcyclopropyl |
| Ia.253 | 2-CN-3-F | c-C₆H₁₁ |
| Ia.254 | 2-NO₂-3-CF₃ | n-C₃H₇ |
| Ia.255 | 2-NO₂-3-CF₃ | iso-C₃H₇ |
| Ia.256 | 2-NO₂-3-CF₃ | n-C₄H₉ |
| Ia.257 | 2-NO₂-3-CF₃ | iso-C₄H₉ |
| Ia.258 | 2-NO₂-3-CF₃ | sec-C₄H₉ |
| Ia.259 | 2-NO₂-3-CF₃ | 3-methylbutyl |
| Ia.260 | 2-NO₂-3-CF₃ | n-C₅H₁₁ |
| Ia.261 | 2-NO₂-3-CF₃ | CH₂—C(CH₃)=CH₂ |
| Ia.262 | 2-NO₂-3-CF₃ | CH₂-c-C₃H₅ |
| Ia.263 | 2-NO₂-3-CF₃ | 1-ethylcyclopropyl |
| Ia.264 | 2-NO₂-3-CF₃ | c-C₆H₁₁ |
| Ia.265 | 2-CH₃-3-SCH₃ | n-C₃H₇ |
| Ia.266 | 2-CH₃-3-SCH₃ | iso-C₃H₇ |
| Ia.267 | 2-CH₃-3-SCH₃ | n-C₄H₉ |
| Ia.268 | 2-CH₃-3-SCH₃ | iso-C₄H₉ |
| Ia.269 | 2-CH₃-3-SCH₃ | sec-C₄H₉ |
| Ia.270 | 2-CH₃-3-SCH₃ | 3-methylbutyl |
| Ia.271 | 2-CH₃-3-SCH₃ | n-C₅H₁₁ |
| Ia.272 | 2-CH₃-3-SCH₃ | CH₂—C(CH₃)=CH₂ |
| Ia.273 | 2-CH₃-3-SCH₃ | CH₂-c-C₃H₅ |
| Ia.274 | 2-CH₃-3-SCH₃ | 1-ethylcyclopropyl |
| Ia.275 | 2-CH₃-3-SCH₃ | c-C₆H₁₁ |
| Ia.276 | 2-CH₃-3-SO₂CH₃ | n-C₃H₇ |
| Ia.277 | 2-CH₃-3-SO₂CH₃ | iso-C₃H₇ |
| Ia.278 | 2-CH₃-3-SO₂CH₃ | n-C₄H₉ |
| Ia.279 | 2-CH₃-3-SO₂CH₃ | iso-C₄H₉ |
| Ia.280 | 2-CH₃-3-SO₂CH₃ | sec-C₄H₉ |
| Ia.281 | 2-CH₃-3-SO₂CH₃ | 3-methylbutyl |
| Ia.282 | 2-CH₃-3-SO₂CH₃ | n-C₅H₁₁ |
| Ia.283 | 2-CH₃-3-SO₂CH₃ | CH₂—C(CH₃)=CH₂ |
| Ia.284 | 2-CH₃-3-SO₂CH₃ | CH₂-c-C₃H₅ |
| Ia.285 | 2-CH₃-3-SO₂CH₃ | 1-ethylcyclopropyl |
| Ia.286 | 2-CH₃-3-SO₂CH₃ | c-C₆H₁₁ |
| Ia.287 | 2-CH₃-3-OCH₃ | n-C₃H₇ |
| Ia.288 | 2-CH₃-3-OCH₃ | iso-C₃H₇ |
| Ia.289 | 2-CH₃-3-OCH₃ | n-C₄H₉ |
| Ia.290 | 2-CH₃-3-OCH₃ | iso-C₄H₉ |
| Ia.291 | 2-CH₃-3-OCH₃ | sec-C₄H₉ |
| Ia.292 | 2-CH₃-3-OCH₃ | 3-methylbutyl |
| Ia.293 | 2-CH₃-3-OCH₃ | n-C₅H₁₁ |
| Ia.294 | 2-CH₃-3-OCH₃ | CH₂—C(CH₃)=CH₂ |
| Ia.295 | 2-CH₃-3-OCH₃ | CH₂-c-C₃H₅ |
| Ia.296 | 2-CH₃-3-OCH₃ | 1-ethylcyclopropyl |
| Ia.297 | 2-CH₃-3-OCH₃ | c-C₆H₁₁ |
| Ia.298 | 2-CN-3-OCH₃ | n-C₃H₇ |
| Ia.299 | 2-CN-3-OCH₃ | iso-C₃H₇ |
| Ia.300 | 2-CN-3-OCH₃ | n-C₄H₉ |
| Ia.301 | 2-CN-3-OCH₃ | iso-C₄H₉ |
| Ia.302 | 2-CN-3-OCH₃ | sec-C₄H₉ |
| Ia.303 | 2-CN-3-OCH₃ | 3-methylbutyl |
| Ia.304 | 2-CN-3-OCH₃ | n-C₅H₁₁ |
| Ia.305 | 2-CN-3-OCH₃ | CH₂—C(CH₃)=CH₂ |
| Ia.306 | 2-CN-3-OCH₃ | CH₂-c-C₃H₅ |
| Ia.307 | 2-CN-3-OCH₃ | 1-ethylcyclopropyl |
| Ia.308 | 2-CN-3-OCH₃ | c-C₆H₁₁ |
| Ia.309 | 2-CO₂CH₃-3-Cl | n-C₃H₇ |
| Ia.310 | 2-CO₂CH₃-3-Cl | iso-C₃H₇ |
| Ia.311 | 2-CO₂CH₃-3-Cl | n-C₄H₉ |
| Ia.312 | 2-CO₂CH₃-3-Cl | iso-C₄H₉ |
| Ia.313 | 2-CO₂CH₃-3-Cl | sec-C₄H₉ |
| Ia.314 | 2-CO₂CH₃-3-Cl | 3-methylbutyl |
| Ia.315 | 2-CO₂CH₃-3-Cl | n-C₅H₁₁ |
| Ia.316 | 2-CO₂CH₃-3-Cl | CH₂—C(CH₃)=CH₂ |
| Ia.317 | 2-CO₂CH₃-3-Cl | CH₂-c-C₃H₅ |

TABLE 1-continued

Ia

| (R²)ₒ | R⁶ |
|---|---|
| Ia.318 2-CO₂CH₃-3-Cl | 1-ethylcyclopropyl |
| Ia.319 2-CO₂CH₃-3-Cl | c-C₆H₁₁ |
| Ia.320 2,3-(CH₃)₂-4-OCH₃ | n-C₃H₇ |
| Ia.321 2,3-(CH₃)₂-4-OCH₃ | iso-C₃H₇ |
| Ia.322 2,3-(CH₃)₂-4-OCH₃ | n-C₄H₉ |
| Ia.323 2,3-(CH₃)₂-4-OCH₃ | iso-C₄H₉ |
| Ia.324 2,3-(CH₃)₂-4-OCH₃ | sec-C₄H₉ |
| Ia.325 2,3-(CH₃)₂-4-OCH₃ | 3-methylbutyl |
| Ia.326 2,3-(CH₃)₂-4-OCH₃ | n-C₅H₁₁ |
| Ia.327 2,3-(CH₃)₂-4-OCH₃ | CH₂—C(CH₃)=CH₂ |
| Ia.328 2,3-(CH₃)₂-4-OCH₃ | CH₂-c-C₃H₅ |
| Ia.329 2,3-(CH₃)₂-4-OCH₃ | 1-ethylcyclopropyl |
| Ia.330 2,3-(CH₃)₂-4-OCH₃ | c-C₆H₁₁ |
| Ia.331 2-CO₂CH₃-3-Br | n-C₃H₇ |
| Ia.332 2-CO₂CH₃-3-Br | iso-C₃H₇ |
| Ia.333 2-CO₂CH₃-3-Br | n-C₄H₉ |
| Ia.334 2-CO₂CH₃-3-Br | iso-C₄H₉ |
| Ia.335 2-CO₂CH₃-3-Br | sec-C₄H₉ |
| Ia.336 2-CO₂CH₃-3-Br | 3-methylbutyl |
| Ia.337 2-CO₂CH₃-3-Br | n-C₅H₁₁ |
| Ia.338 2-CO₂CH₃-3-Br | CH₂—C(CH₃)=CH₂ |
| Ia.339 2-CO₂CH₃-3-Br | CH₂-c-C₃H₅ |
| Ia.340 2-CO₂CH₃-3-Br | 1-ethylcyclopropyl |
| Ia.341 2-CO₂CH₃-3-Br | c-C₆H₁₁ |
| Ia.342 2-CN-3-CH₃ | n-C₃H₇ |
| Ia.343 2-CN-3-CH₃ | iso-C₃H₇ |
| Ia.344 2-CN-3-CH₃ | n-C₄H₉ |
| Ia.345 2-CN-3-CH₃ | iso-C₄H₉ |
| Ia.346 2-CN-3-CH₃ | sec-C₄H₉ |
| Ia.347 2-CN-3-CH₃ | 3-methylbutyl |
| Ia.348 2-CN-3-CH₃ | n-C₅H₁₁ |
| Ia.349 2-CN-3-CH₃ | CH₂—C(CH₃)=CH₂ |
| Ia.350 2-CN-3-CH₃ | CH₂-c-C₃H₅ |
| Ia.351 2-CN-3-CH₃ | 1-ethylcyclopropyl |
| Ia.352 2-CN-3-CH₃ | c-C₆H₁₁ |
| Ia.353 2-CN-3-Cl-6-CH₃ | n-C₃H₇ |
| Ia.354 2-CN-3-Cl-6-CH₃ | iso-C₃H₇ |
| Ia.355 2-CN-3-Cl-6-CH₃ | n-C₄H₉ |
| Ia.356 2-CN-3-Cl-6-CH₃ | iso-C₄H₉ |
| Ia.357 2-CN-3-Cl-6-CH₃ | sec-C₄H₉ |
| Ia.358 2-CN-3-Cl-6-CH₃ | 3-methylbutyl |
| Ia.359 2-CN-3-Cl-6-CH₃ | n-C₅H₁₁ |
| Ia.360 2-CN-3-Cl-6-CH₃ | CH₂—C(CH₃)=CH₂ |
| Ia.361 2-CN-3-Cl-6-CH₃ | CH₂-c-C₃H₅ |
| Ia.362 2-CN-3-Cl-6-CH₃ | 1-ethylcyclopropyl |
| Ia.363 2-CN-3-Cl-6-CH₃ | c-C₆H₁₁ |
| Ia.364 2-CO₂CH₃-3-Cl-6-CH₃ | n-C₃H₇ |
| Ia.365 2-CO₂CH₃-3-Cl-6-CH₃ | iso-C₃H₇ |
| Ia.366 2-CO₂CH₃-3-Cl-6-CH₃ | n-C₄H₉ |
| Ia.367 2-CO₂CH₃-3-Cl-6-CH₃ | iso-C₄H₉ |
| Ia.368 2-CO₂CH₃-3-Cl-6-CH₃ | sec-C₄H₉ |
| Ia.369 2-CO₂CH₃-3-Cl-6-CH₃ | 3-methylbutyl |
| Ia.370 2-CO₂CH₃-3-Cl-6-CH₃ | n-C₅H₁₁ |
| Ia.371 2-CO₂CH₃-3-Cl-6-CH₃ | CH₂—C(CH₃)=CH₂ |
| Ia.372 2-CO₂CH₃-3-Cl-6-CH₃ | CH₂-c-C₃H₅ |
| Ia.373 2-CO₂CH₃-3-Cl-6-CH₃ | 1-ethylcyclopropyl |
| Ia.374 2-CO₂CH₃-3-Cl-6-CH₃ | c-C₆H₁₁ |
| Ia.375 2-Cl-3-CF₃ | n-C₃H₇ |
| Ia.376 2-Cl-3-CF₃ | i-C₃H₇ |
| Ia.377 2-Cl-3-CF₃ | n-C₄H₉ |
| Ia.378 2-Cl-3-CF₃ | i-C₄H₉ |
| Ia.379 2-Cl-3-CF₃ | sec-C₄H₉ |
| Ia.380 2-Cl-3-CF₃ | 3-methylbutyl |
| Ia.381 2-Cl-3-CF₃ | n-C₅H₁₁ |
| Ia.382 2-Cl-3-CF₃ | CH₂—C(CH₃)=CH₂ |
| Ia.383 2-Cl-3-CF₃ | CH₂-c-C₃H₅ |
| Ia.384 2-Cl-3-CF₃ | 1-ethylcyclopropyl |
| Ia.385 2-CN-3-CF₃ | n-C₃H₇ |
| Ia.386 2-CN-3-CF₃ | i-C₃H₇ |
| Ia.387 2-CN-3-CF₃ | n-C₄H₉ |
| Ia.388 2-CN-3-CF₃ | i-C₄H₉ |
| Ia.389 2-CN-3-CF₃ | sec-C₄H₉ |
| Ia.390 2-CN-3-CF₃ | 3-methylbutyl |
| Ia.391 2-CN-3-CF₃ | n-C₅H₁₁ |
| Ia.392 2-CN-3-CF₃ | CH₂—C(CH₃)=CH₂ |
| Ia.393 2-CN-3-CF₃ | CH₂-c-C₃H₅ |
| Ia.394 2-CN-3-CF₃ | 1-ethylcyclopropyl |
| Ia.395 2-CH₃-3-Cl-6-CH₃O—CO | n-C₃H₇ |
| Ia.396 2-CH₃-3-Cl-6-CH₃O—CO | i-C₃H₇ |
| Ia.397 2-CH₃-3-Cl-6-CH₃O—CO | n-C₄H₉ |
| Ia.398 2-CH₃-3-Cl-6-CH₃O—CO | i-C₄H₉ |
| Ia.399 2-CH₃-3-Cl-6-CH₃O—CO | sec-C₄H₉ |
| Ia.400 2-CH₃-3-Cl-6-CH₃O—CO | 3-methylbutyl |
| Ia.401 2-CH₃-3-Cl-6-CH₃O—CO | n-C₅H₁₁ |
| Ia.402 2-CH₃-3-Cl-6-CH₃O—CO | CH₂—C(CH₃)=CH₂ |
| Ia.403 2-CH₃-3-Cl-6-CH₃O—CO | CH₂-c-C₃H₅ |
| Ia.404 2-CH₃-3-Cl-6-CH₃O—CO | 1-ethylcyclopropyl |
| Ia.405 2-CH₃O—(CO)-3,6(CH₃)₂ | n-C₃H₇ |
| Ia.406 2-CH₃O—(CO)-3,6(CH₃)₂ | i-C₃H₇ |
| Ia.407 2-CH₃O—(CO)-3,6(CH₃)₂ | n-C₄H₉ |
| Ia.408 2-CH₃O—(CO)-3,6(CH₃)₂ | i-C₄H₉ |
| Ia.409 2-CH₃O—(CO)-3,6(CH₃)₂ | sec-C₄H₉ |
| Ia.410 2-CH₃O—(CO)-3,6(CH₃)₂ | 3-methylbutyl |
| Ia.411 2-CH₃O—(CO)-3,6(CH₃)₂ | n-C₅H₁₁ |
| Ia.412 2-CH₃O—(CO)-3,6(CH₃)₂ | CH₂—C(CH₃)=CH₂ |
| Ia.413 2-CH₃O—(CO)-3,6(CH₃)₂ | CH₂-c-C₃H₅ |
| Ia.414 2-CH₃O—(CO)-3,6(CH₃)₂ | 1-ethylcyclopropyl |
| Ia.415 2-NH₂—(CO)-3-Cl-6-CH₃ | n-C₃H₇ |
| Ia.416 2-NH₂—(CO)-3-Cl-6-CH₃ | i-C₃H₇ |
| Ia.417 2-NH₂—(CO)-3-Cl-6-CH₃ | n-C₄H₉ |
| Ia.418 2-NH₂—(CO)-3-Cl-6-CH₃ | i-C₄H₉ |
| Ia.419 2-NH₂—(CO)-3-Cl-6-CH₃ | sec-C₄H₉ |
| Ia.420 2-NH₂—(CO)-3-Cl-6-CH₃ | 3-methylbutyl |
| Ia.421 2-NH₂—(CO)-3-Cl-6-CH₃ | n-C₅H₁₁ |
| Ia.422 2-NH₂—(CO)-3-Cl-6-CH₃ | CH₂—C(CH₃)=CH₂ |
| Ia.423 2-NH₂—(CO)-3-Cl-6-CH₃ | CH₂-c-C₃H₅ |
| Ia.424 2-NH₂—(CO)-3-Cl-6-CH₃ | 1-ethylcyclopropyl |
| Ia.425 2-CH₃O—(CO)-3,6-Cl₂ | n-C₃H₇ |
| Ia.426 2-CH₃O—(CO)-3,6-Cl₂ | i-C₃H₇ |
| Ia.427 2-CH₃O—(CO)-3,6-Cl₂ | n-C₄H₉ |
| Ia.428 2-CH₃O—(CO)-3,6-Cl₂ | i-C₄H₉ |
| Ia.429 2-CH₃O—(CO)-3,6-Cl₂ | sec-C₄H₉ |
| Ia.430 2-CH₃O—(CO)-3,6-Cl₂ | 3-methylbutyl |
| Ia.431 2-CH₃O—(CO)-3,6-Cl₂ | n-C₅H₁₁ |
| Ia.432 2-CH₃O—(CO)-3,6-Cl₂ | CH₂—C(CH₃)=CH₂ |
| Ia.433 2-CH₃O—(CO)-3,6-Cl₂ | CH₂-c-C₃H₅ |
| Ia.434 2-CH₃O—(CO)-3,6-Cl₂ | 1-ethylcyclopropyl |
| Ia.435 2-CN-3-CH₃-6-Cl | n-C₃H₇ |
| Ia.436 2-CN-3-CH₃-6-Cl | i-C₃H₇ |
| Ia.437 2-CN-3-CH₃-6-Cl | n-C₄H₉ |
| Ia.438 2-CN-3-CH₃-6-Cl | i-C₄H₉ |
| Ia.439 2-CN-3-CH₃-6-Cl | sec-C₄H₉ |
| Ia.440 2-CN-3-CH₃-6-Cl | 3-methylbutyl |
| Ia.441 2-CN-3-CH₃-6-Cl | n-C₅H₁₁ |
| Ia.442 2-CN-3-CH₃-6-Cl | CH₂—C(CH₃)=CH₂ |
| Ia.443 2-CN-3-CH₃-6-Cl | CH₂-c-C₃H₅ |
| Ia.444 2-CN-3-CH₃-6-Cl | 1-ethylcyclopropyl |
| Ia.445 2-CH₃O—(CO)-3-CH₃-6-Cl | n-C₃H₇ |

TABLE 1-continued

Ia

| | (R²)ₒ | R⁶ |
|---|---|---|
| Ia.446 | 2-CH₃O—(CO)-3-CH₃-6-Cl | i-C₃H₇ |
| Ia.447 | 2-CH₃O—(CO)-3-CH₃-6-Cl | n-C₄H₉ |
| Ia.448 | 2-CH₃O—(CO)-3-CH₃-6-Cl | i-C₄H₉ |
| Ia.449 | 2-CH₃O—(CO)-3-CH₃-6-Cl | sec-C₄H₉ |
| Ia.450 | 2-CH₃O—(CO)-3-CH₃-6-Cl | 3-methylbutyl |
| Ia.451 | 2-CH₃O—(CO)-3-CH₃-6-Cl | n-C₅H₁₁ |
| Ia.452 | 2-CH₃O—(CO)-3-CH₃-6-Cl | CH₂—C(CH₃)=CH₂ |
| Ia.453 | 2-CH₃O—(CO)-3-CH₃-6-Cl | CH₂-c-C₃H₅ |
| Ia.454 | 2-CH₃O—(CO)-3-CH₃-6-Cl | 1-ethylcyclopropyl |
| Ia.455 | 2-CN-3,6-Cl₂ | n-C₃H₇ |
| Ia.456 | 2-CN-3,6-Cl₂ | i-C₃H₇ |
| Ia.457 | 2-CN-3,6-Cl₂ | n-C₄H₉ |
| Ia.458 | 2-CN-3,6-Cl₂ | i-C₄H₉ |
| Ia.459 | 2-CN-3,6-Cl₂ | sec-C₄H₉ |
| Ia.460 | 2-CN-3,6-Cl₂ | 3-methylbutyl |
| Ia.461 | 2-CN-3,6-Cl₂ | n-C₅H₁₁ |
| Ia.462 | 2-CN-3,6-Cl₂ | CH₂—C(CH₃)=CH₂ |
| Ia.463 | 2-CN-3,6-Cl₂ | CH₂-c-C₃H₅ |
| Ia.464 | 2-CN-3,6-Cl₂ | 1-ethylcyclopropyl |
| Ia.465 | 2-CN-3,6(CH₃)₂ | n-C₃H₇ |
| Ia.466 | 2-CN-3,6(CH₃)₂ | i-C₃H₇ |
| Ia.467 | 2-CN-3,6(CH₃)₂ | n-C₄H₉ |
| Ia.468 | 2-CN-3,6(CH₃)₂ | i-C₄H₉ |
| Ia.469 | 2-CN-3,6(CH₃)₂ | sec-C₄H₉ |
| Ia.470 | 2-CN-3,6(CH₃)₂ | 3-methylbutyl |
| Ia.471 | 2-CN-3,6(CH₃)₂ | n-C₅H₁₁ |
| Ia.472 | 2-CN-3,6(CH₃)₂ | CH₂—C(CH₃)=CH₂ |
| Ia.473 | 2-CN-3,6(CH₃)₂ | CH₂-c-C₃H₅ |
| Ia.474 | 2-CN-3,6(CH₃)₂ | 1-ethylcyclopropyl |
| Ia.475 | 2-CH₃-3-CH₃O—(CO)-6-Cl | n-C₃H₇ |
| Ia.476 | 2-CH₃-3-CH₃O—(CO)-6-Cl | i-C₃H₇ |
| Ia.477 | 2-CH₃-3-CH₃O—(CO)-6-Cl | n-C₄H₉ |
| Ia.478 | 2-CH₃-3-CH₃O—(CO)-6-Cl | i-C₄H₉ |
| Ia.479 | 2-CH₃-3-CH₃O—(CO)-6-Cl | sec-C₄H₉ |
| Ia.480 | 2-CH₃-3-CH₃O—(CO)-6-Cl | 3-methylbutyl |
| Ia.481 | 2-CH₃-3-CH₃O—(CO)-6-Cl | n-C₅H₁₁ |
| Ia.482 | 2-CH₃-3-CH₃O—(CO)-6-Cl | CH₂—C(CH₃)=CH₂ |
| Ia.483 | 2-CH₃-3-CH₃O—(CO)-6-Cl | CH₂-c-C₃H₅ |
| Ia.484 | 2-CH₃-3-CH₃O—(CO)-6-Cl | 1-ethylcyclopropyl |
| Ia.485 | 2,6-(CH₃)₂-3-CH₃O—(CO)— | n-C₃H₇ |
| Ia.486 | 2,6-(CH₃)₂-3-CH₃O—(CO)— | i-C₃H₇ |
| Ia.487 | 2,6-(CH₃)₂-3-CH₃O—(CO)— | n-C₄H₉ |
| Ia.488 | 2,6-(CH₃)₂-3-CH₃O—(CO)— | i-C₄H₉ |
| Ia.489 | 2,6-(CH₃)₂-3-CH₃O—(CO)— | sec-C₄H₉ |
| Ia.490 | 2,6-(CH₃)₂-3-CH₃O—(CO)— | 3-methylbutyl |
| Ia.491 | 2,6-(CH₃)₂-3-CH₃O—(CO)— | n-C₅H₁₁ |
| Ia.492 | 2,6-(CH₃)₂-3-CH₃O—(CO)— | CH₂—C(CH₃)=CH₂ |
| Ia.493 | 2,6-(CH₃)₂-3-CH₃O—(CO)— | CH₂-c-C₃H₅ |
| Ia.494 | 2,6-(CH₃)₂-3-CH₃O—(CO)— | 1-ethylcyclopropyl |
| Ia.495 | 2-CN-3-CH₃ | n-C₃H₇ |
| Ia.496 | 2-CN-3-CH₃ | i-C₃H₇ |
| Ia.497 | 2-CN-3-CH₃ | n-C₄H₉ |
| Ia.498 | 2-CN-3-CH₃ | i-C₄H₉ |
| Ia.499 | 2-CN-3-CH₃ | sec-C₄H₉ |
| Ia.500 | 2-CN-3-CH₃ | 3-methylbutyl |
| Ia.501 | 2-CN-3-CH₃ | n-C₅H₁₁ |
| Ia.502 | 2-CN-3-CH₃ | CH₂—C(CH₃)=CH₂ |
| Ia.503 | 2-CN-3-CH₃ | CH₂-c-C₃H₅ |
| Ia.504 | 2-CN-3-CH₃ | 1-ethylcyclopropyl |
| Ia.505 | 2-CH₃O—CO-3-CH₃ | n-C₃H₇ |
| Ia.506 | 2-CH₃O—CO-3-CH₃ | i-C₃H₇ |
| Ia.507 | 2-CH₃O—CO-3-CH₃ | n-C₄H₉ |
| Ia.508 | 2-CH₃O—CO-3-CH₃ | i-C₄H₉ |
| Ia.509 | 2-CH₃O—CO-3-CH₃ | sec-C₄H₉ |
| Ia.510 | 2-CH₃O—CO-3-CH₃ | 3-methylbutyl |
| Ia.511 | 2-CH₃O—CO-3-CH₃ | n-C₅H₁₁ |
| Ia.512 | 2-CH₃O—CO-3-CH₃ | CH₂—C(CH₃)=CH₂ |
| Ia.513 | 2-CH₃O—CO-3-CH₃ | CH₂-c-C₃H₅ |
| Ia.514 | 2-CH₃O—CO-3-CH₃ | 1-ethylcyclopropyl |
| Ia.515 | 2-CH₃-3-Cl-6-CN | n-C₃H₇ |
| Ia.516 | 2-CH₃-3-Cl-6-CN | i-C₃H₇ |
| Ia.517 | 2-CH₃-3-Cl-6-CN | n-C₄H₉ |
| Ia.518 | 2-CH₃-3-Cl-6-CN | i-C₄H₉ |
| Ia.519 | 2-CH₃-3-Cl-6-CN | sec-C₄H₉ |
| Ia.520 | 2-CH₃-3-Cl-6-CN | 3-methylbutyl |
| Ia.521 | 2-CH₃-3-Cl-6-CN | n-C₅H₁₁ |
| Ia.522 | 2-CH₃-3-Cl-6-CN | CH₂—C(CH₃)=CH₂ |
| Ia.523 | 2-CH₃-3-Cl-6-CN | CH₂-c-C₃H₅ |
| Ia.524 | 2-CH₃-3-Cl-6-CN | 1-ethylcyclopropyl |
| Ia.525 | 2-Cl-3-CH₃-6-CN | n-C₃H₇ |
| Ia.526 | 2-Cl-3-CH₃-6-CN | i-C₃H₇ |
| Ia.527 | 2-Cl-3-CH₃-6-CN | n-C₄H₉ |
| Ia.528 | 2-Cl-3-CH₃-6-CN | i-C₄H₉ |
| Ia.529 | 2-Cl-3-CH₃-6-CN | sec-C₄H₉ |
| Ia.530 | 2-Cl-3-CH₃-6-CN | 3-methylbutyl |
| Ia.531 | 2-Cl-3-CH₃-6-CN | n-C₅H₁₁ |
| Ia.532 | 2-Cl-3-CH₃-6-CN | CH₂—C(CH₃)=CH₂ |
| Ia.533 | 2-Cl-3-CH₃-6-CN | CH₂-c-C₃H₅ |
| Ia.534 | 2-Cl-3-CH₃-6-CN | 1-ethylcyclopropyl |
| Ia.535 | 2-Cl-3-CH₃-6-CH₃O—CO— | n-C₃H₇ |
| Ia.536 | 2-Cl-3-CH₃-6-CH₃O—CO— | i-C₃H₇ |
| Ia.537 | 2-Cl-3-CH₃-6-CH₃O—CO— | n-C₄H₉ |
| Ia.538 | 2-Cl-3-CH₃-6-CH₃O—CO— | i-C₄H₉ |
| Ia.539 | 2-Cl-3-CH₃-6-CH₃O—CO— | sec-C₄H₉ |
| Ia.540 | 2-Cl-3-CH₃-6-CH₃O—CO— | 3-methylbutyl |
| Ia.541 | 2-Cl-3-CH₃-6-CH₃O—CO— | n-C₅H₁₁ |
| Ia.542 | 2-Cl-3-CH₃-6-CH₃O—CO— | CH₂—C(CH₃)=CH₂ |
| Ia.543 | 2-Cl-3-CH₃-6-CH₃O—CO— | CH₂-c-C₃H₅ |
| Ia.544 | 2-Cl-3-CH₃-6-CH₃O—CO— | 1-ethylcyclopropyl |
| Ia.545 | 2-CH₃O—(CO)-3-Br-6-C₂H₅ | n-C₃H₇ |
| Ia.546 | 2-CH₃O—(CO)-3-Br-6-C₂H₅ | i-C₃H₇ |
| Ia.547 | 2-CH₃O—(CO)-3-Br-6-C₂H₅ | n-C₄H₉ |
| Ia.548 | 2-CH₃O—(CO)-3-Br-6-C₂H₅ | i-C₄H₉ |
| Ia.549 | 2-CH₃O—(CO)-3-Br-6-C₂H₅ | sec-C₄H₉ |
| Ia.550 | 2-CH₃O—(CO)-3-Br-6-C₂H₅ | 3-methylbutyl |
| Ia.551 | 2-CH₃O—(CO)-3-Br-6-C₂H₅ | n-C₅H₁₁ |
| Ia.552 | 2-CH₃O—(CO)-3-Br-6-C₂H₅ | CH₂—C(CH₃)=CH₂ |
| Ia.553 | 2-CH₃O—(CO)-3-Br-6-C₂H₅ | CH₂-c-C₃H₅ |
| Ia.554 | 2-CH₃O—(CO)-3-Br-6-C₂H₅ | 1-ethylcyclopropyl |
| Ia.555 | 2-CH₃O—CO-3-Cl-6-CN | n-C₃H₇ |
| Ia.556 | 2-CH₃O—CO-3-Cl-6-CN | i-C₃H₇ |
| Ia.557 | 2-CH₃O—CO-3-Cl-6-CN | n-C₄H₉ |
| Ia.558 | 2-CH₃O—CO-3-Cl-6-CN | i-C₄H₉ |
| Ia.559 | 2-CH₃O—CO-3-Cl-6-CN | sec-C₄H₉ |
| Ia.560 | 2-CH₃O—CO-3-Cl-6-CN | 3-methylbutyl |
| Ia.561 | 2-CH₃O—CO-3-Ci-6-CN | n-C₅H₁₁ |
| Ia.562 | 2-CH₃O—CO-3-Cl-6-CN | CH₂—C(CH₃)=CH₂ |
| Ia.563 | 2-CH₃O—CO-3-Cl-6-CN | CH₂-c-C₃H₅ |
| Ia.564 | 2-CH₃O—CO-3-Cl-6-CN | 1-ethylcyclopropyl |
| Ia.565 | 2-CN-3-Cl-6-CH₃O—(CO) | n-C₃H₇ |
| Ia.566 | 2-CN-3-Cl-6-CH₃O—(CO) | i-C₃H₇ |
| Ia.567 | 2-CN-3-Cl-6-CH₃O—(CO) | n-C₄H₉ |
| Ia.568 | 2-CN-3-Cl-6-CH₃O—(CO) | i-C₄H₉ |
| Ia.569 | 2-CN-3-Cl-6-CH₃O—(CO) | sec-C₄H₉ |
| Ia.570 | 2-CN-3-Cl-6-CH₃O—(CO) | 3-methylbutyl |
| Ia.571 | 2-CN-3-Cl-6-CH₃O—(CO) | n-C₅H₁₁ |
| Ia.572 | 2-CN-3-Cl-6-CH₃O—(CO) | CH₂—C(CH₃)=CH₂ |
| Ia.573 | 2-CN-3-Cl-6-CH₃O—(CO) | CH₂-c-C₃H₅ |

TABLE 1-continued

Ia (structure: pyridine with H3C at 5-position, H3C at 6-position, C(O)NH-phenyl(R2)o at 3-position, C(O)NHR6 at 2-position)

| | (R²)ₒ | R⁶ |
|---|---|---|
| Ia.574 | 2-CN-3-Cl-6-CH₃O—(CO) | 1-ethylcyclopropyl |
| Ia.575 | 2-CH₃O—(CO)-3-Cl-6-C₂H₅ | n-C₃H₇ |
| Ia.576 | 2-CH₃O—(CO)-3-Cl-6-C₂H₅ | i-C₃H₇ |
| Ia.577 | 2-CH₃O—(CO)-3-Cl-6-C₂H₅ | n-C₄H₉ |
| Ia.578 | 2-CH₃O—(CO)-3-Cl-6-C₂H₅ | i-C₄H₉ |
| Ia.579 | 2-CH₃O—(CO)-3-Cl-6-C₂H₅ | sec-C₄H₉ |
| Ia.580 | 2-CH₃O—(CO)-3-Cl-6-C₂H₅ | 3-methylbutyl |
| Ia.581 | 2-CH₃O—(CO)-3-Cl-6-C₂H₅ | n-C₅H₁₁ |
| Ia.582 | 2-CH₃O—(CO)-3-Cl-6-C₂H₅ | CH₂—C(CH₃)=CH₂ |
| Ia.583 | 2-CH₃O—(CO)-3-Cl-6-C₂H₅ | CH₂-c-C₃H₅ |
| Ia.584 | 2-CH₃O—(CO)-3-Cl-6-C₂H₅ | 1-ethylcyclopropyl |
| Ia.585 | 2-CH₃O—(CO)-3-Cl-6-C₂H₅ | (CH₂)₃Cl |
| Ia.586 | 2-CH₃O—(CO)-3-Br-6-CH₃ | n-C₃H₇ |
| Ia.587 | 2-CH₃O—(CO)-3-Br-6-CH₃ | i-C₃H₇ |
| Ia.588 | 2-CH₃O—(CO)-3-Br-6-CH₃ | n-C₄H₉ |
| Ia.589 | 2-CH₃O—(CO)-3-Br-6-CH₃ | i-C₄H₉ |
| Ia.590 | 2-CH₃O—(CO)-3-Br-6-CH₃ | sec-C₄H₉ |
| Ia.591 | 2-CH₃O—(CO)-3-Br-6-CH₃ | 3-methylbutyl |
| Ia.592 | 2-CH₃O—(CO)-3-Br-6-CH₃ | n-C₅H₁₁ |
| Ia.593 | 2-CH₃O—(CO)-3-Br-6-CH₃ | CH₂—C(CH₃)=CH₂ |
| Ia.594 | 2-CH₃O—(CO)-3-Br-6-CH₃ | CH₂-c-C₃H₅ |
| Ia.595 | 2-CH₃O—(CO)-3-Br-6-CH₃ | 1-ethylcyclopropyl |
| Ia.596 | 2-CH₃O—(CO)-3-Br-6-CH₃ | (CH₂)₃Cl |
| Ia.597 | 2-C₂H₅-3-Cl-6-CN | n-C₃H₇ |
| Ia.598 | 2-C₂H₅-3-Cl-6-CN | i-C₃H₇ |
| Ia.599 | 2-C₂H₅-3-Cl-6-CN | n-C₄H₉ |
| Ia.600 | 2-C₂H₅-3-Cl-6-CN | i-C₄H₉ |
| Ia.601 | 2-C₂H₅-3-Cl-6-CN | sec-C₄H₉ |
| Ia.602 | 2-C₂H₅-3-Cl-6-CN | 3-methylbutyl |
| Ia.603 | 2-C₂H₅-3-Cl-6-CN | n-C₅H₁₁ |
| Ia.604 | 2-C₂H₅-3-Cl-6-CN | CH₂—C(CH₃)=CH₂ |
| Ia.605 | 2-C₂H₅-3-Cl-6-CN | CH₂-c-C₃H₅ |
| Ia.606 | 2-C₂H₅-3-Cl-6-CN | 1-ethylcyclopropyl |
| Ia.607 | 2-C₂H₅-3-Cl-6-CN | (CH₂)₃Cl |
| Ia.608 | 2-C₂H₅-3-Cl-6-CH₃O—(CO) | n-C₃H₇ |
| Ia.609 | 2-C₂H₅-3-Cl-6-CH₃O—(CO) | i-C₃H₇ |
| Ia.610 | 2-C₂H₅-3-Cl-6-CH₃O—(CO) | n-C₄H₉ |
| Ia.611 | 2-C₂H₅-3-Cl-6-CH₃O—(CO) | i-C₄H₉ |
| Ia.612 | 2-C₂H₅-3-Cl-6-CH₃O—(CO) | sec-C₄H₉ |
| Ia.613 | 2-C₂H₅-3-Cl-6-CH₃O—(CO) | 3-methylbutyl |
| Ia.614 | 2-C₂H₅-3-Cl-6-CH₃O—(CO) | n-C₅H₁₁ |
| Ia.615 | 2-C₂H₅-3-Cl-6-CH₃O—(CO) | CH₂—C(CH₃)=CH₂ |
| Ia.616 | 2-C₂H₅-3-Cl-6-CH₃O—(CO) | CH₂-c-C₃H₅ |
| Ia.617 | 2-C₂H₅-3-Cl-6-CH₃O—(CO) | 1-ethylcyclopropyl |
| Ia.618 | 2-C₂H₅-3-Cl-6-CH₃O—(CO) | (CH₂)₃Cl |
| Ia.619 | 2-CH₃O-C(O)-3-Cl-6-CH₃O | n-C₃H₇ |
| Ia.620 | 2-CH₃O-C(O)-3-Cl-6-CH₃O | i-C₃H₇ |
| Ia.621 | 2-CH₃O-C(O)-3-Cl-6-CH₃O | n-C₄H₉ |
| Ia.622 | 2-CH₃O-C(O)-3-Cl-6-CH₃O | i-C₄H₉ |
| Ia.623 | 2-CH₃O-C(O)-3-Cl-6-CH₃O | sec-C₄H₉ |
| Ia.624 | 2-CH₃O-C(O)-3-Cl-6-CH₃O | 3-methylbutyl |
| Ia.625 | 2-CH₃O-C(O)-3-Cl-6-CH₃O | n-C₅H₁₁ |
| Ia.626 | 2-CH₃O-C(O)-3-Cl-6-CH₃O | CH₂—C(CH₃)=CH₂ |
| Ia.627 | 2-CH₃O-C(O)-3-Cl-6-CH₃O | CH₂-c-C₃H₅ |
| Ia.628 | 2-CH₃O-C(O)-3-Cl-6-CH₃O | 1-ethylcyclopropyl |
| Ia.629 | 2-CH₃O-C(O)-3-Cl-6-CH₃O | (CH₂)₃Cl |
| Ia.630 | 2-CN-3-Cl-6-CH₃O | n-C₃H₇ |
| Ia.631 | 2-CN-3-Cl-6-CH₃O | i-C₃H₇ |
| Ia.632 | 2-CN-3-Cl-6-CH₃O | n-C₄H₉ |
| Ia.633 | 2-CN-3-Cl-6-CH₃O | i-C₄H₉ |
| Ia.634 | 2-CN-3-Cl-6-CH₃O | sec-C₄H₉ |
| Ia.635 | 2-CN-3-Cl-6-CH₃O | 3-methylbutyl |
| Ia.636 | 2-CN-3-Cl-6-CH₃O | n-C₅H₁₁ |
| Ia.637 | 2-CN-3-Cl-6-CH₃O | CH₂—C(CH₃)=CH₂ |
| Ia.638 | 2-CN-3-Cl-6-CH₃O | CH₂-c-C₃H₅ |
| Ia.639 | 2-CN-3-Cl-6-CH₃O | 1-ethylcyclopropyl |
| Ia.640 | 2-CN-3-Cl-6-CH₃O | (CH₂)₃Cl |
| Ia.641 | 2-CH₃O-CH₂-3-Cl-6-CH₃ | n-C₃H₇ |
| Ia.642 | 2-CH₃O-CH₂-3-Cl-6-CH₃ | i-C₃H₇ |
| Ia.643 | 2-CH₃O-CH₂-3-Cl-6-CH₃ | n-C₄H₉ |
| Ia.644 | 2-CH₃O-CH₂-3-Cl-6-CH₃ | i-C₄H₉ |
| Ia.645 | 2-CH₃O-CH₂-3-Cl-6-CH₃ | sec-C₄H₉ |
| Ia.646 | 2-CH₃O-CH₂-3-Cl-6-CH₃ | 3-methylbutyl |
| Ia.647 | 2-CH₃O-CH₂-3-Cl-6-CH₃ | n-C₅H₁₁ |
| Ia.648 | 2-CH₃O-CH₂-3-Cl-6-CH₃ | CH₂—C(CH₃)=CH₂ |
| Ia.649 | 2-CH₃O-CH₂-3-Cl-6-CH₃ | CH₂-c-C₃H₅ |
| Ia.650 | 2-CH₃O-CH₂-3-Cl-6-CH₃ | 1-ethylcyclopropyl |
| Ia.651 | 2-CH₃O-CH₂-3-Cl-6-CH₃ | (CH₂)₃Cl |
| Ia.652 | 2-CH₃-3-Cl-6-CH₃O—CH₂ | n-C₃H₇ |
| Ia.653 | 2-CH₃-3-Cl-6-CH₃O—CH₂ | i-C₃H₇ |
| Ia.654 | 2-CH₃-3-Cl-6-CH₃O—CH₂ | n-C₄H₉ |
| Ia.655 | 2-CH₃-3-Cl-6-CH₃O—CH₂ | i-C₄H₉ |
| Ia.656 | 2-CH₃-3-Cl-6-CH₃O—CH₂ | sec-C₄H₉ |
| Ia.657 | 2-CH₃-3-Cl-6-CH₃O—CH₂ | 3-methylbutyl |
| Ia.658 | 2-CH₃-3-Cl-6-CH₃O—CH₂ | n-C₅H₁₁ |
| Ia.659 | 2-CH₃-3-Cl-6-CH₃O—CH₂ | CH₂—C(CH₃)=CH₂ |
| Ia.660 | 2-CH₃-3-Cl-6-CH₃O—CH₂ | CH₂-c-C₃H₅ |
| Ia.661 | 2-CH₃-3-Cl-6-CH₃O—CH₂ | 1-ethylcyclopropyl |
| Ia.662 | 2-CH₃-3-Cl-6-CH₃O—CH₂ | (CH₂)₃Cl |
| Ia.663 | 2-CH₃O—CH₂-3-Br-6-CH₃ | n-C₃H₇ |
| Ia.664 | 2-CH₃O—CH₂-3-Br-6-CH₃ | i-C₃H₇ |
| Ia.665 | 2-CH₃O—CH₂-3-Br-6-CH₃ | n-C₄H₉ |
| Ia.666 | 2-CH₃O—CH₂-3-Br-6-CH₃ | i-C₄H₉ |
| Ia.667 | 2-CH₃O—CH₂-3-Br-6-CH₃ | sec-C₄H₉ |
| Ia.668 | 2-CH₃O—CH₂-3-Br-6-CH₃ | 3-methylbutyl |
| Ia.669 | 2-CH₃O—CH₂-3-Br-6-CH₃ | n-C₅H₁₁ |
| Ia.670 | 2-CH₃O—CH₂-3-Br-6-CH₃ | CH₂—C(CH₃)=CH₂ |
| Ia.671 | 2-CH₃O—CH₂-3-Br-6-CH₃ | CH₂-c-C₃H₅ |
| Ia.672 | 2-CH₃O—CH₂-3-Br-6-CH₃ | 1-ethylcyclopropyl |
| Ia.673 | 2-CH₃O—CH₂-3-Br-6-CH₃ | (CH₂)₃Cl |
| Ia.674 | 2-CH₃O—N=CH-3-Cl | n-C₃H₇ |
| Ia.675 | 2-CH₃O—N=CH-3-Cl | i-C₃H₇ |
| Ia.676 | 2-CH₃O—N=CH-3-Cl | n-C₄H₉ |
| Ia.677 | 2-CH₃O—N=CH-3-Cl | i-C₄H₉ |
| Ia.678 | 2-CH₃O—N=CH-3-Cl | sec-C₄H₉ |
| Ia.679 | 2-CH₃O—N=CH-3-Cl | 3-methylbutyl |
| Ia.680 | 2-CH₃O—N=CH-3-Cl | n-C₅H₁₁ |
| Ia.681 | 2-CH₃O—N=CH-3-Cl | CH₂—C(CH₃)=CH₂ |
| Ia.682 | 2-CH₃O—N=CH-3-Cl | CH₂-c-C₃H₅ |
| Ia.683 | 2-CH₃O—N=CH-3-Cl | 1-ethylcyclopropyl |
| Ia.684 | 2-CH₃O—N=CH-3-Cl | (CH₂)₃Cl |
| Ia.685 | 2-CH₃O—N=CH-3-Cl-6-CH₃ | n-C₃H₇ |
| Ia.686 | 2-CH₃O—N=CH-3-Cl-6-CH₃ | i-C₃H₇ |
| Ia.687 | 2-CH₃O—N=CH-3-Cl-6-CH₃ | n-C₄H₉ |
| Ia.688 | 2-CH₃O—N=CH-3-Cl-6-CH₃ | i-C₄H₉ |
| Ia.689 | 2-CH₃O—N=CH-3-Cl-6-CH₃ | sec-C₄H₉ |
| Ia.690 | 2-CH₃O—N=CH-3-Cl-6-CH₃ | 3-methylbutyl |
| Ia.691 | 2-CH₃O—N=CH-3-Cl-6-CH₃ | n-C₅H₁₁ |
| Ia.692 | 2-CH₃O—N=CH-3-Cl-6-CH₃ | CH₂—C(CH₃)=CH₂ |
| Ia.693 | 2-CH₃O—N=CH-3-Cl-6-CH₃ | CH₂-c-C₃H₅ |
| Ia.694 | 2-CH₃O—N=CH-3-Cl-6-CH₃ | 1-ethylcyclopropyl |
| Ia.695 | 2-CH₃O—N=CH-3-Cl-6-CH₃ | (CH₂)₃Cl |

TABLE 2

![Structure Ib: pyridine with 5-CH3, 6-CH3 substituents, 3-position C(=O)NH-O-Q, and 2-position C(=O)NHR6]

Ib

| | Q | R6 |
|---|---|---|
| Ib.1 | 1-naphthyl | n-C$_3$H$_7$ |
| Ib.2 | 1-naphthyl | iso-C$_3$H$_7$ |
| Ib.3 | 1-naphthyl | n-C$_4$H$_9$ |
| Ib.4 | 1-naphthyl | iso-C$_4$H$_9$ |
| Ib.5 | 1-naphthyl | sec-C$_4$H$_9$ |
| Ib.6 | 1-naphthyl | 3-methylbutyl |
| Ib.7 | 1-naphthyl | n-C$_5$H$_{11}$ |
| Ib.8 | 1-naphthyl | CH$_2$—C(CH$_3$)=CH$_2$ |
| Ib.9 | 1-naphthyl | CH$_2$-c-C$_3$H$_5$ |
| Ib.10 | 1-naphthyl | 1-ethylcyclopropyl |
| Ib.11 | 1-naphthyl | c-C$_6$H$_{11}$ |
| Ib.12 | 2-naphthyl | n-C$_3$H$_7$ |
| Ib.13 | 2-naphthyl | iso-C$_3$H$_7$ |
| Ib.14 | 2-naphthyl | n-C$_4$H$_9$ |
| Ib.15 | 2-naphthyl | iso-C$_4$H$_9$ |
| Ib.16 | 2-naphthyl | sec-C$_4$H$_9$ |
| Ib.17 | 2-naphthyl | 3-methylbutyl |
| Ib.18 | 2-naphthyl | n-C$_5$H$_{11}$ |
| Ib.19 | 2-naphthyl | CH$_2$—C(CH$_3$)=CH$_2$ |
| Ib.20 | 2-naphthyl | CH$_2$-c-C$_3$H$_5$ |
| Ib.21 | 2-naphthyl | 1-ethylcyclopropyl |
| Ib.22 | 2-naphthyl | c-C$_6$H$_{11}$ |
| Ib.23 | 2-CH$_3$-naphth-1-yl | n-C$_3$H$_7$ |
| Ib.24 | 2-CH$_3$-naphth-1-yl | iso-C$_3$H$_7$ |
| Ib.25 | 2-CH$_3$-naphth-1-yl | n-C$_4$H$_9$ |
| Ib.26 | 2-CH$_3$-naphth-1-yl | iso-C$_4$H$_9$ |
| Ib.27 | 2-CH$_3$-naphth-1-yl | sec-C$_4$H$_9$ |
| Ib.28 | 2-CH$_3$-naphth-1-yl | 3-methylbutyl |
| Ib.29 | 2-CH$_3$-naphth-1-yl | n-C$_5$H$_{11}$ |
| Ib.30 | 2-CH$_3$-naphth-1-yl | CH$_2$—C(CH$_3$)=CH$_2$ |
| Ib.31 | 2-CH$_3$-naphth-1-yl | CH$_2$-c-C$_3$H$_5$ |
| Ib.32 | 2-CH$_3$-naphth-1-yl | 1-ethylcyclopropyl |
| Ib.33 | 2-CH$_3$-naphth-1-yl | c-C$_6$H$_{11}$ |
| Ib.34 | 2,4-(CH$_3$)$_2$-naphth-1-yl | n-C$_3$H$_7$ |
| Ib.35 | 2,4-(CH$_3$)$_2$-naphth-1-yl | iso-C$_3$H$_7$ |
| Ib.36 | 2,4-(CH$_3$)$_2$-naphth-1-yl | n-C$_4$H$_9$ |
| Ib.37 | 2,4-(CH$_3$)$_2$-naphth-1-yl | iso-C$_4$H$_9$ |
| Ib.38 | 2,4-(CH$_3$)$_2$-naphth-1-yl | sec-C$_4$H$_9$ |
| Ib.39 | 2,4-(CH$_3$)$_2$-naphth-1-yl | 3-methylbutyl |
| Ib.40 | 2,4-(CH$_3$)$_2$-naphth-1-yl | n-C$_5$H$_{11}$ |
| Ib.41 | 2,4-(CH$_3$)$_2$-naphth-1-yl | CH$_2$—C(CH$_3$)=CH$_2$ |
| Ib.42 | 2,4-(CH$_3$)$_2$-naphth-1-yl | CH$_2$-c-C$_3$H$_5$ |
| Ib.43 | 2,4-(CH$_3$)$_2$-naphth-1-yl | 1-ethylcyclopropyl |
| Ib.44 | 2,4-(CH$_3$)$_2$-naphth-1-yl | c-C$_6$H$_{11}$ |
| Ib.45 | 4-Cl-naphth-1-yl | n-C$_3$H$_7$ |
| Ib.46 | 4-Cl-naphth-1-yl | iso-C$_3$H$_7$ |
| Ib.47 | 4-Cl-naphth-1-yl | n-C$_4$H$_9$ |
| Ib.48 | 4-Cl-naphth-1-yl | iso-C$_4$H$_9$ |
| Ib.49 | 4-Cl-naphth-1-yl | sec-C$_4$H$_9$ |
| Ib.50 | 4-Cl-naphth-1-yl | 3-methylbutyl |
| Ib.51 | 4-Cl-naphth-1-yl | n-C$_5$H$_{11}$ |
| Ib.52 | 4-Cl-naphth-1-yl | CH$_2$—C(CH$_3$)=CH$_2$ |
| Ib.53 | 4-Cl-naphth-1-yl | CH$_2$-c-C$_3$H$_5$ |
| Ib.54 | 4-Cl-naphth-1-yl | 1-ethylcyclopropyl |
| Ib.55 | 4-Cl-naphth-1-yl | c-C$_6$H$_{11}$ |
| Ib.56 | 1,3-(CH$_3$)$_2$-naphth-2-yl | n-C$_3$H$_7$ |
| Ib.57 | 1,3-(CH$_3$)$_2$-naphth-2-yl | iso-C$_3$H$_7$ |
| Ib.58 | 1,3-(CH$_3$)$_2$-naphth-2-yl | n-C$_4$H$_9$ |
| Ib.59 | 1,3-(CH$_3$)$_2$-naphth-2-yl | iso-C$_4$H$_9$ |
| Ib.60 | 1,3-(CH$_3$)$_2$-naphth-2-yl | sec-C$_4$H$_9$ |
| Ib.61 | 1,3-(CH$_3$)$_2$-naphth-2-yl | 3-methylbutyl |
| Ib.62 | 1,3-(CH$_3$)$_2$-naphth-2-yl | n-C$_5$H$_{11}$ |
| Ib.63 | 1,3-(CH$_3$)$_2$-naphth-2-yl | CH$_2$—C(CH$_3$)=CH$_2$ |
| Ib.64 | 1,3-(CH$_3$)$_2$-naphth-2-yl | CH$_2$-c-C$_3$H$_5$ |
| Ib.65 | 1,3-(CH$_3$)$_2$-naphth-2-yl | 1-ethylcyclopropyl |
| Ib.66 | 1,3-(CH$_3$)$_2$-naphth-2-yl | c-C$_6$H$_{11}$ |
| Ib.67 | quinol-4-yl | n-C$_3$H$_7$ |
| Ib.68 | quinol-4-yl | iso-C$_3$H$_7$ |
| Ib.69 | quinol-4-yl | n-C$_4$H$_9$ |
| Ib.70 | quinol-4-yl | iso-C$_4$H$_9$ |
| Ib.71 | quinol-4-yl | sec-C$_4$H$_9$ |
| Ib.72 | quinol-4-yl | 3-methylbutyl |
| Ib.73 | quinol-4-yl | n-C$_5$H$_{11}$ |
| Ib.74 | quinol-4-yl | CH$_2$—C(CH$_3$)=CH$_2$ |
| Ib.75 | quinol-4-yl | CH$_2$-c-C$_3$H$_5$ |
| Ib.76 | quinol-4-yl | 1-ethylcyclopropyl |
| Ib.77 | quinol-4-yl | c-C$_6$H$_{11}$ |
| Ib.78 | 2-CH$_3$-quinol-4-yl | n-C$_3$H$_7$ |
| Ib.79 | 2-CH$_3$-quinol-4-yl | iso-C$_3$H$_7$ |
| Ib.80 | 2-CH$_3$-quinol-4-yl | n-C$_4$H$_9$ |
| Ib.81 | 2-CH$_3$-quinol-4-yl | iso-C$_4$H$_9$ |
| Ib.82 | 2-CH$_3$-quinol-4-yl | sec-C$_4$H$_9$ |
| Ib.83 | 2-CH$_3$-quinol-4-yl | 3-methylbutyl |
| Ib.84 | 2-CH$_3$-quinol-4-yl | n-C$_5$H$_{11}$ |
| Ib.85 | 2-CH$_3$-quinol-4-yl | CH$_2$—C(CH$_3$)=CH$_2$ |
| Ib.86 | 2-CH$_3$-quinol-4-yl | CH$_2$-c-C$_3$H$_5$ |
| Ib.87 | 2-CH$_3$-quinol-4-yl | 1-ethylcyclopropyl |
| Ib.88 | 2-CH$_3$-quinol-4-yl | c-C$_6$H$_{11}$ |
| Ib.89 | quinol-5-yl | n-C$_3$H$_7$ |
| Ib.90 | quinol-5-yl | iso-C$_3$H$_7$ |
| Ib.91 | quinol-5-yl | n-C$_4$H$_9$ |
| Ib.92 | quinol-5-yl | iso-C$_4$H$_9$ |
| Ib.93 | quinol-5-yl | sec-C$_4$H$_9$ |
| Ib.94 | quinol-5-yl | 3-methylbutyl |
| Ib.95 | quinol-5-yl | n-C$_5$H$_{11}$ |
| Ib.96 | quinol-5-yl | CH$_2$—C(CH$_3$)=CH$_2$ |
| Ib.97 | quinol-5-yl | CH$_2$-c-C$_3$H$_5$ |
| Ib.98 | quinol-5-yl | 1-ethylcyclopropyl |
| Ib.99 | quinol-5-yl | c-C$_6$H$_{11}$ |
| Ib.100 | isoquinol-5-yl | n-C$_3$H$_7$ |
| Ib.101 | isoquinol-5-yl | iso-C$_3$H$_7$ |
| Ib.102 | isoquinol-5-yl | n-C$_4$H$_9$ |
| Ib.103 | isoquinol-5-yl | iso-C$_4$H$_9$ |
| Ib.104 | isoquinol-5-yl | sec-C$_4$H$_9$ |
| Ib.105 | isoquinol-5-yl | 3-methylbutyl |
| Ib.106 | isoquinol-5-yl | n-C$_5$H$_{11}$ |
| Ib.107 | isoquinol-5-yl | CH$_2$—C(CH$_3$)=CH$_2$ |
| Ib.108 | isoquinol-5-yl | CH$_2$-c-C$_3$H$_5$ |
| Ib.109 | isoquinol-5-yl | 1-ethylcyclopropyl |
| Ib.110 | isoquinol-5-yl | c-C$_6$H$_{11}$ |
| Ib.111 | 3-CH$_3$-isoquinol-5-yl | n-C$_3$H$_7$ |
| Ib.112 | 3-CH$_3$-isoquinol-5-yl | iso-C$_3$H$_7$ |
| Ib.113 | 3-CH$_3$-isoquinol-5-yl | n-C$_4$H$_9$ |
| Ib.114 | 3-CH$_3$-isoquinol-5-yl | iso-C$_4$H$_9$ |
| Ib.115 | 3-CH$_3$-isoquinol-5-yl | sec-C$_4$H$_9$ |
| Ib.116 | 3-CH$_3$-isoquinol-5-yl | 3-methylbutyl |
| Ib.117 | 3-CH$_3$-isoquinol-5-yl | n-C$_5$H$_{11}$ |
| Ib.118 | 3-CH$_3$-isoquinol-5-yl | CH$_2$—C(CH$_3$)=CH$_2$ |
| Ib.119 | 3-CH$_3$-isoquinol-5-yl | CH$_2$-c-C$_3$H$_5$ |
| Ib.120 | 3-CH$_3$-isoquinol-5-yl | 1-ethylcyclopropyl |
| Ib.121 | 3-CH$_3$-isoquinol-5-yl | c-C$_6$H$_{11}$ |
| Ib.122 | benzoxazol-7-yl | n-C$_3$H$_7$ |
| Ib.123 | benzoxazol-7-yl | iso-C$_3$H$_7$ |
| Ib.124 | benzoxazol-7-yl | n-C$_4$H$_9$ |
| Ib.125 | benzoxazol-7-yl | iso-C$_4$H$_9$ |
| Ib.126 | benzoxazol-7-yl | sec-C$_4$H$_9$ |
| Ib.127 | benzoxazol-7-yl | 3-methylbutyl |
| Ib.128 | benzoxazol-7-yl | n-C$_5$H$_{11}$ |
| Ib.129 | benzoxazol-7-yl | CH$_2$—C(CH$_3$)=CH$_2$ |
| Ib.130 | benzoxazol-7-yl | CH$_2$-c-C$_3$H$_5$ |
| Ib.131 | benzoxazol-7-yl | 1-ethylcyclopropyl |
| Ib.132 | benzoxazol-7-yl | c-C$_6$H$_{11}$ |

TABLE 2-continued

| | Q | R6 |
|---|---|---|
| Ib.133 | 2-CH3-benzoxazol-7-yl | n-C3H7 |
| Ib.134 | 2-CH3-benzoxazol-7-yl | iso-C3H7 |
| Ib.135 | 2-CH3-benzoxazol-7-yl | n-C4H9 |
| Ib.136 | 2-CH3-benzoxazol-7-yl | iso-C4H9 |
| Ib.137 | 2-CH3-benzoxazol-7-yl | sec-C4H9 |
| Ib.138 | 2-CH3-benzoxazol-7-yl | 3-methylbutyl |
| Ib.139 | 2-CH3-benzoxazol-7-yl | n-C5H11 |
| Ib.140 | 2-CH3-benzoxazol-7-yl | CH2—C(CH3)=CH2 |
| Ib.141 | 2-CH3-benzoxazol-7-yl | CH2-c-C3H5 |
| Ib.142 | 2-CH3-benzoxazol-7-yl | 1-ethylcyclopropyl |
| Ib.143 | 2-CH3-benzoxazol-7-yl | c-C6H11 |
| Ib.144 | 2-CF3-benzoxazol-7-yl | n-C3H7 |
| Ib.145 | 2-CF3-benzoxazol-7-yl | iso-C3H7 |
| Ib.146 | 2-CF3-benzoxazol-7-yl | n-C4H9 |
| Ib.147 | 2-CF3-benzoxazol-7-yl | iso-C4H9 |
| Ib.148 | 2-CF3-benzoxazol-7-yl | sec-C4H9 |
| Ib.149 | 2-CF3-benzoxazol-7-yl | 3-methylbutyl |
| Ib.150 | 2-CF3-benzoxazol-7-yl | n-C5H11 |
| Ib.151 | 2-CF3-benzoxazol-7-yl | CH2—C(CH3)=CH2 |
| Ib.152 | 2-CF3-benzoxazol-7-yl | CH2-c-C3H5 |
| Ib.153 | 2-CF3-benzoxazol-7-yl | 1-ethylcyclopropyl |
| Ib.154 | 2-CF3-benzoxazol-7-yl | c-C6H11 |
| Ib.155 | 2-c-C3H5-benzoxazol-7-yl | n-C3H7 |
| Ib.156 | 2-c-C3H5-benzoxazol-7-yl | iso-C3H7 |
| Ib.157 | 2-c-C3H5-benzoxazol-7-yl | n-C4H9 |
| Ib.158 | 2-c-C3H5-benzoxazol-7-yl | iso-C4H9 |
| Ib.159 | 2-c-C3H5-benzoxazol-7-yl | sec-C4H9 |
| Ib.160 | 2-c-C3H5-benzoxazol-7-yl | 3-methylbutyl |
| Ib.161 | 2-c-C3H5-benzoxazol-7-yl | n-C5H11 |
| Ib.162 | 2-c-C3H5-benzoxazol-7-yl | CH2—C(CH3)=CH2 |
| Ib.163 | 2-c-C3H5-benzoxazol-7-yl | CH2-c-C3H5 |
| Ib.164 | 2-c-C3H5-benzoxazol-7-yl | 1-ethylcyclopropyl |
| Ib.165 | 2-c-C3H5-benzoxazol-7-yl | c-C6H11 |
| Ib.166 | 2-(tetrahydrofur-2-yl)benzoxazol-7-yl | n-C3H7 |
| Ib.167 | 2-(tetrahydrofur-2-yl)benzoxazol-7-yl | iso-C3H7 |
| Ib.168 | 2-(tetrahydrofur-2-yl)benzoxazol-7-yl | n-C4H9 |
| Ib.169 | 2-(tetrahydrofur-2-yl)benzoxazol-7-yl | iso-C4H9 |
| Ib.170 | 2-(tetrahydrofur-2-yl)benzoxazol-7-yl | sec-C4H9 |
| Ib.171 | 2-(tetrahydrofur-2-yl)benzoxazol-7-yl | 3-methylbutyl |
| Ib.172 | 2-(tetrahydrofur-2-yl)benzoxazol-7-yl | n-C5H11 |
| Ib.173 | 2-(tetrahydrofur-2-yl)benzoxazol-7-yl | CH2—C(CH3)=CH2 |
| Ib.174 | 2-(tetrahydrofur-2-yl)benzoxazol-7-yl | CH2-c-C3H5 |
| Ib.175 | 2-(tetrahydrofur-2-yl)benzoxazol-7-yl | 1-ethylcyclopropyl |
| Ib.176 | 2-(tetrahydrofur-2-yl)benzoxazol-7-yl | c-C6H11 |
| Ib.177 | benzothiazol-7-yl | n-C3H7 |
| Ib.178 | benzothiazol-7-yl | iso-C3H7 |
| Ib.179 | benzothiazol-7-yl | n-C4H9 |
| Ib.180 | benzothiazol-7-yl | iso-C4H9 |
| Ib.181 | benzothiazol-7-yl | sec-C4H9 |
| Ib.182 | benzothiazol-7-yl | 3-methylbutyl |
| Ib.183 | benzothiazol-7-yl | n-C5H11 |
| Ib.184 | benzothiazol-7-yl | CH2—C(CH3)=CH2 |
| Ib.185 | benzothiazol-7-yl | CH2-c-C3H5 |
| Ib.186 | benzothiazol-7-yl | 1-ethylcyclopropyl |
| Ib.187 | benzothiazol-7-yl | c-C6H11 |
| Ib.188 | 2-CH3-benzothiazol-7-yl | n-C3H7 |
| Ib.189 | 2-CH3-benzothiazol-7-yl | iso-C3H7 |
| Ib.190 | 2-CH3-benzothiazol-7-yl | n-C4H9 |
| Ib.191 | 2-CH3-benzothiazol-7-yl | iso-C4H9 |
| Ib.192 | 2-CH3-benzothiazol-7-yl | sec-C4H9 |
| Ib.193 | 2-CH3-benzothiazol-7-yl | 3-methylbutyl |
| Ib.194 | 2-CH3-benzothiazol-7-yl | n-C5H11 |
| Ib.195 | 2-CH3-benzothiazol-7-yl | CH2—C(CH3)=CH2 |
| Ib.196 | 2-CH3-benzothiazol-7-yl | CH2-c-C3H5 |
| Ib.197 | 2-CH3-benzothiazol-7-yl | 1-ethylcyclopropyl |
| Ib.198 | 2-CH3-benzothiazol-7-yl | c-C6H11 |
| Ib.199 | 2-CF3-benzothiazol-7-yl | n-C3H7 |
| Ib.200 | 2-CF3-benzothiazol-7-yl | iso-C3H7 |
| Ib.201 | 2-CF3-benzothiazol-7-yl | n-C4H9 |
| Ib.202 | 2-CF3-benzothiazol-7-yl | iso-C4H9 |
| Ib.203 | 2-CF3-benzothiazol-7-yl | sec-C4H9 |
| Ib.204 | 2-CF3-benzothiazol-7-yl | 3-methylbutyl |
| Ib.205 | 2-CF3-benzothiazol-7-yl | n-C5H11 |
| Ib.206 | 2-CF3-benzothiazol-7-yl | CH2—C(CH3)=CH2 |
| Ib.207 | 2-CF3-benzothiazol-7-yl | CH2-c-C3H5 |
| Ib.208 | 2-CF3-benzothiazol-7-yl | 1-ethylcyclopropyl |
| Ib.209 | 2-CF3-benzothiazol-7-yl | c-C6H11 |
| Ib.210 | 2-c-C3H5-benzothiazol-7-yl | n-C3H7 |
| Ib.211 | 2-c-C3H5-benzothiazol-7-yl | iso-C3H7 |
| Ib.212 | 2-c-C3H5-benzothiazol-7-yl | n-C4H9 |
| Ib.213 | 2-c-C3H5-benzothiazol-7-yl | iso-C4H9 |
| Ib.214 | 2-c-C3H5-benzothiazol-7-yl | sec-C4H9 |
| Ib.215 | 2-c-C3H5-benzothiazol-7-yl | 3-methylbutyl |
| Ib.216 | 2-c-C3H5-benzothiazol-7-yl | n-C5H11 |
| Ib.217 | 2-c-C3H5-benzothiazol-7-yl | CH2—C(CH3)=CH2 |
| Ib.218 | 2-c-C3H5-benzothiazol-7-yl | CH2-c-C3H5 |
| Ib.219 | 2-c-C3H5-benzothiazol-7-yl | 1-ethylcyclopropyl |
| Ib.220 | 2-c-C3H5-benzothiazol-7-yl | c-C6H11 |
| Ib.221 | 2-(tetrahydrofur-2-yl)benzothiazol-7-yl | n-C3H7 |
| Ib.222 | 2-(tetrahydrofur-2-yl)benzothiazol-7-yl | iso-C3H7 |
| Ib.223 | 2-(tetrahydrofur-2-yl)benzothiazol-7-yl | n-C4H9 |
| Ib.224 | 2-(tetrahydrofur-2-yl)benzothiazol-7-yl | iso-C4H9 |
| Ib.225 | 2-(tetrahydrofur-2-yl)benzothiazol-7-yl | sec-C4H9 |
| Ib.226 | 2-(tetrahydrofur-2-yl)benzothiazol-7-yl | 3-methylbutyl |
| Ib.227 | 2-(tetrahydrofur-2-yl)benzothiazol-7-yl | n-C5H11 |
| Ib.228 | 2-(tetrahydrofur-2-yl)benzothiazol-7-yl | CH2—C(CH3)=CH2 |
| Ib.229 | 2-(tetrahydrofur-2-yl)benzothiazol-7-yl | CH2-c-C3H5 |
| Ib.230 | 2-(tetrahydrofur-2-yl)benzothiazol-7-yl | 1-ethylcyclopropyl |
| Ib.231 | 2-(tetrahydrofur-2-yl)benzothiazol-7-yl | c-C6H11 |
| Ib.232 | 2-(pyran-2-yl)benzoxazol-7-yl | n-C3H7 |
| Ib.233 | 2-(pyran-2-yl)benzoxazol-7-yl | iso-C3H7 |
| Ib.234 | 2-(pyran-2-yl)benzoxazol-7-yl | n-C4H9 |
| Ib.235 | 2-(pyran-2-yl)benzoxazol-7-yl | iso-C4H9 |
| Ib.236 | 2-(pyran-2-yl)benzoxazol-7-yl | sec-C4H9 |
| Ib.237 | 2-(pyran-2-yl)benzoxazol-7-yl | 3-methylbutyl |
| Ib.238 | 2-(pyran-2-yl)benzoxazol-7-yl | n-C5H11 |
| Ib.239 | 2-(pyran-2-yl)benzoxazol-7-yl | CH2—C(CH3)=CH2 |
| Ib.240 | 2-(pyran-2-yl)benzoxazol-7-yl | CH2-c-C3H5 |
| Ib.241 | 2-(pyran-2-yl)benzoxazol-7-yl | 1-ethylcyclopropyl |
| Ib.242 | 2-(pyran-2-yl)benzoxazol-7-yl | c-C6H11 |
| Ib.243 | 2,2-difluorobenzodioxol-4-yl | n-C3H7 |
| Ib.244 | 2,2-difluorobenzodioxol-4-yl | i-C3H7 |
| Ib.245 | 2,2-difluorobenzodioxol-4-yl | n-C4H9 |
| Ib.246 | 2,2-difluorobenzodioxol-4-yl | i-C4H9 |
| Ib.247 | 2,2-difluorobenzodioxol-4-yl | sec-C4H9 |
| Ib.248 | 2,2-difluorobenzodioxol-4-yl | 3-methylbutyl |
| Ib.249 | 2,2-difluorobenzodioxol-4-yl | n-C5H11 |
| Ib.250 | 2,2-difluorobenzodioxol-4-yl | CH2—C(CH3)=CH2 |
| Ib.251 | 2,2-difluorobenzodioxol-4-yl | CH2-c-C3H5 |

TABLE 2-continued

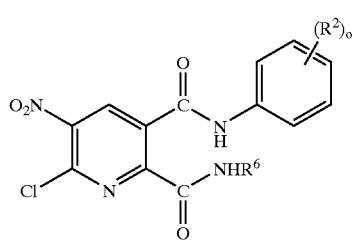

Ib

| | Q | R⁶ |
|---|---|---|
| Ib.252 | 2,2-difluorobenzodioxol-4-yl | 1-ethylcyclopropyl |
| Ib.253 | 2,2-difluorobenzodioxol-4-yl | c-C₆H₁₁ |

Furthermore, particular preference is given to the substituted pyridine-2,3-dicarboxamides below:

the compounds of the formulae II a, Nos 2 a.1 to 2 a.695 and II b, Nos 2 b.1 to 2 b.253, which differ from the corresponding compounds of the formulae I a, Nos 1 a.1 to 1 a.695 and I b, Nos 1 b.1 to 1 b.253 only in that $(R^1)_n$ is 5-NO$_2$-6-Cl:

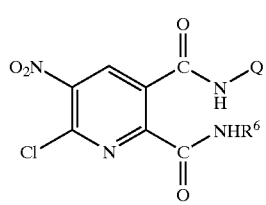

IIa

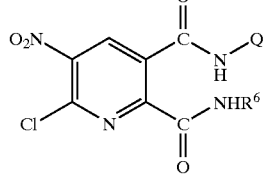

IIb the compounds of the formulae III a, Nos 3 a.1 to 3 a.695 and III b, Nos 3 b.1 to 3 b.253, which differ from the corresponding compounds of the formulae I a, Nos 1 a.1 to 1 a.695 and I b, Nos 1 b.1 to 1 b.253 only in that $(R^1)_n$ is 5-NH$_2$-6-Cl:

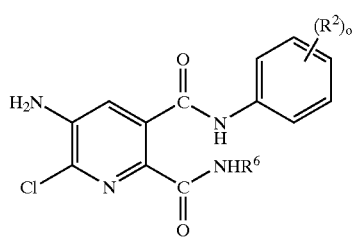

IIIa

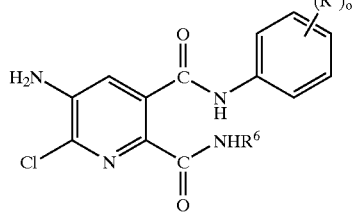

IIIb the compounds of the formulae IV a, Nos 4 a.1 to 4 a.695 and IV b, Nos.4 b.1 to 4 b.253, which differ from the corresponding compounds of the formulae I a, Nos 1 a.1 to 1 a.695 and I b, Nos 1 b.1 to 1 b.253 only in that $(R^1)_n$ is 5,6-Cl$_2$:

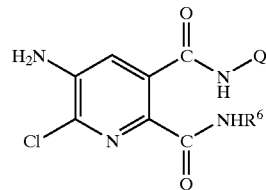

IVa

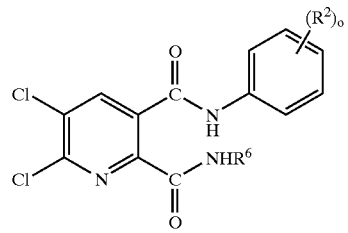

IVb the compounds of the formulae V a, Nos 5 a.1 to 5 a.695, and V b, Nos 5 b.1 to 5 b.253, which differ from the corresponding compounds of the formulae I a, Nos 1 a.1 to 1 a.695 and I b, Nos 1 b.1 to 1 b.253 only in that $(R^1)_n$ is 5-Cl-6-CH$_3$O:

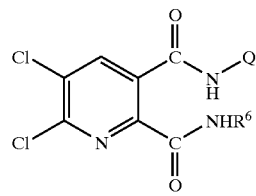

Va

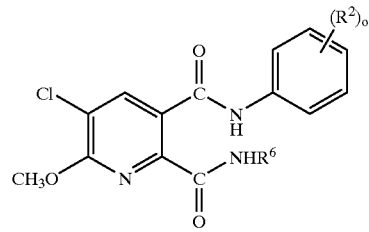

Vb

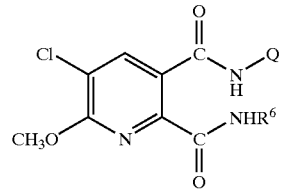

the compounds of the formulae VI a, Nos 6 a.1 to 6 a.695, and VI b, Nos 6 b.1 to 6 b.253, which differ from the corresponding compounds of the formulae I a, Nos 1 a.1 to 1 a.695 and I b, Nos 1 b.1 to 1 b.253 only in that $(R^1)_n$ is 5-CH$_3$O-6-Cl:

VIa

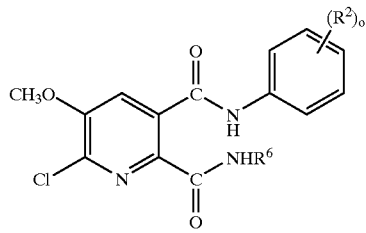

VIb

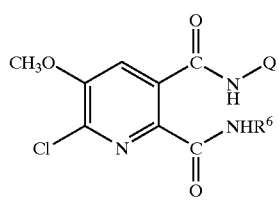

the compounds of the formulae VII a, Nos 7 a.1 to 7 a.695, and VII b, Nos 7 b.1 to 7 b.253, which differ from the corresponding compounds of the formulae I a, Nos 1 a.1 to 1 a.695 and I b, Nos 1 b.1 to 1 b.253 only in that $(R^1)_n$ is 5-CH$_3$-6-Cl:

VIIa

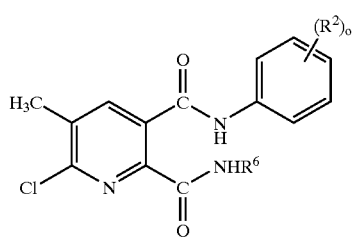

VIIb

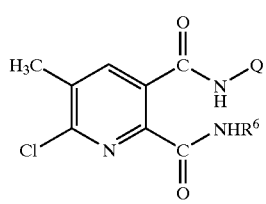

the compounds of the formulae VIIIa, Nos 8 a.1 to 8 a.695, and VIII b, Nos 8 b.1 to 8 b.253, which differ from the corresponding compounds of the formulae I a, Nos 1 a.1 to 1 a.695 and I b, Nos 1 b.1 to 1 b.253 only in that $(R^1)_n$ is 5-Cl-6-CH$_3$:

VIIIa

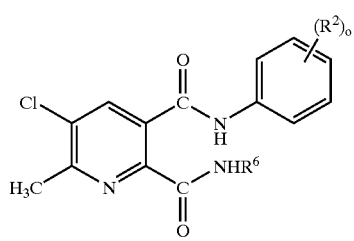

VIIIb

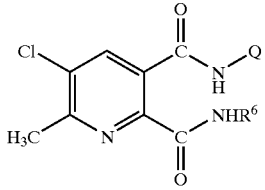

the compounds of the formulae IX a, Nos 9 a.1 to 9 a.695, and IX b, Nos 9 b.1 to 9 b.253, which differ from the corresponding compounds of the formulae I a, Nos 1 a.1 to 1 a.695 and I b, Nos 1 b.1 to 1 b.253 only in that $(R^1)_n$ is 5-NO$_2$-6-CH$_3$:

IXa

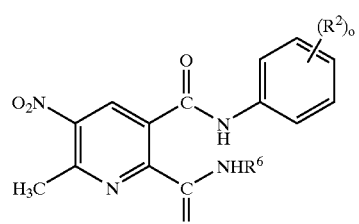

IXb

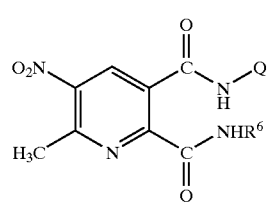

the compounds of the formulae X a, Nos 10 a.1 to 10 a.695, and X b, Nos 10 b.1 to 10 b.253, which differ from the corresponding compounds of the formulae I a, Nos 1 a.1 to 1 a.695 and I b, Nos 1 b.1 to 1 b.253 only in that $(R^1)_n$ is 5-CH$_3$-6-NO$_2$:

Xa

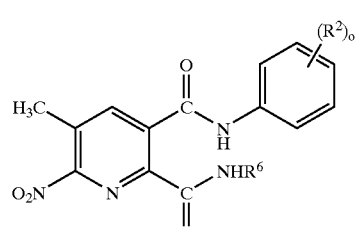

Xb

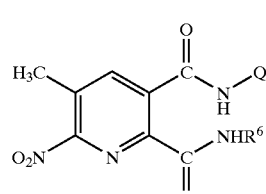

the compounds of the formulae XI a, Nos 11 a.1 to 11 a.695, and XI b, Nos 11 b.1 to 11 b.253, which differ from the corresponding compounds of the formulae I a, Nos 1 a.1 to 1 a.695 and I b, Nos 1 b.1 to 1 b.253 only in that $(R^1)_n$ is 5-NO$_2$-6-CH$_3$O:

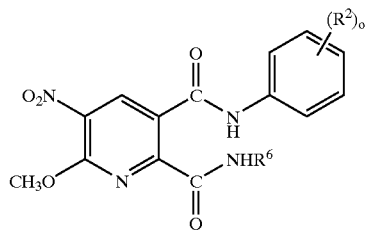
XIa

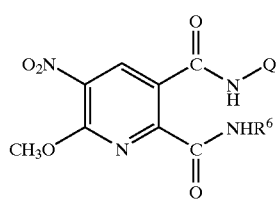
XIb the compounds of the formulae XII a, Nos 12 a.1 to 12 a.695, and XII b, Nos 12 b.1 to 12 b.253, which differ from the corresponding compounds of the formulae I a, Nos 1 a.1 to 1 a.695 and I b, Nos 1 b.1 to 1 b.253 only in that $(R^1)_n$ is 5-CH$_3$O-6-NO$_2$:

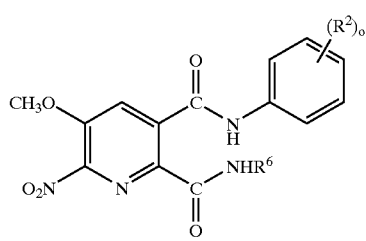
XIIa

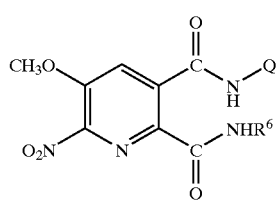
XIIb the compounds of the formulae XIII a, Nos 13 a.1 to 13 a.695, and XIII b, Nos 13 b.1 to 13 b.253, which differ from the corresponding compounds of the formulae I a, Nos 1 a.1 to 1 a.695 and I b, Nos 1 b.1 to 1 b.253 only in that $(R^1)_n$ is 5-CH$_3$-6-CH$_3$O:

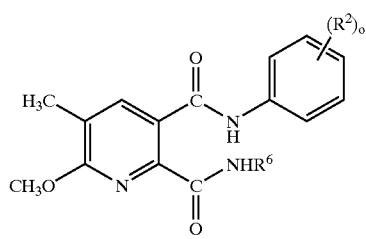
XIIIa

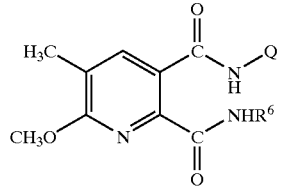
XIIIb the compounds of the formulae XIV a, Nos 14 a.1 to 14 a.695, and XIV b, Nos 14 b.1 to 14 b.253, which differ from the corresponding compounds of the formulae I a, Nos 1 a.1 to 1 a.695 and I b, Nos 1 b.1 to 1 b.253 only in that $(R^1)_n$ is 5-CH$_3$O-6-CH$_3$:

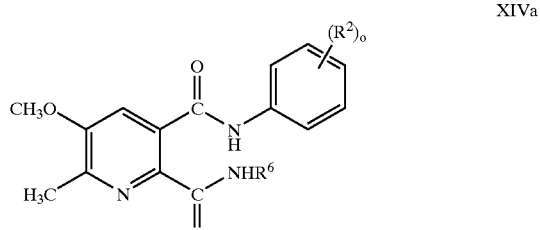
XIVa

XIVb the compounds of the formulae XV a, Nos 15 a.1 to 15 a.695, and XV b, Nos 15 b.1 to 15 b.253, which differ from the corresponding compounds of the formulae I a, Nos 1 a.1 to 1 a.695 and I b, Nos 1 b.1 to 1 b.253 only in that $(R^1)_n$ is 5,6-(CH$_3$O)$_2$:

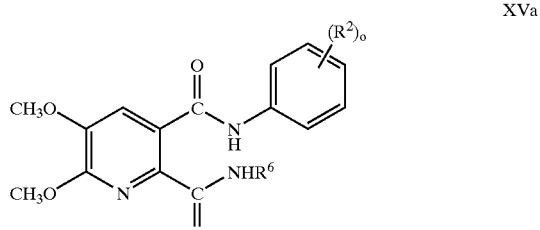
XVa

XVb the compounds of the formulae XVI a, Nos 16 a.1 to 16 a.695, and XVI b, Nos 16 b.1 to 16 b.253, which differ from the corresponding compounds of the formulae I a, Nos 1 a.1 to 1 a.695 and I b, Nos 1 b.1 to 1 b.253 only in that $(R^1)_n$ is 5-CH$_3$-6-NH$_2$:

XVIa

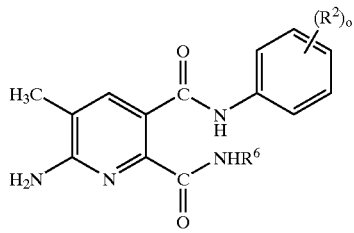

XVIb

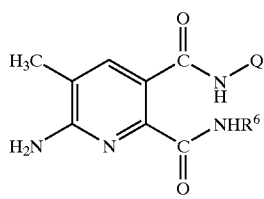

the compounds of the formulae XVII a, Nos 17 a.1 to 17 a.695, and XVII b, Nos 17 b.1 to 17 b.253, which differ from the corresponding compounds of the formulae I a, Nos 1 a.1 to 1 a.695 and I b, Nos 1 b.1 to 1 b.253 only in that $(R^1)_n$ is 5-NH$_2$-6-CH$_3$:

XVIIa

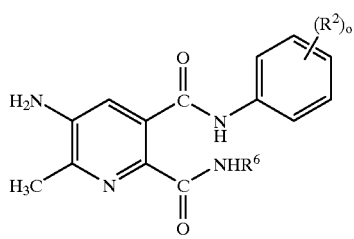

XVIIb

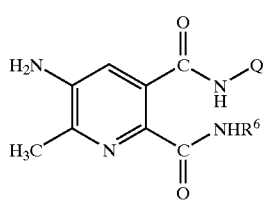

the compounds of the formulae XVIII a, Nos 18 a.1 to 18 a.695, and XVIII b, Nos 18 b.1 to 18 b.253, which differ from the corresponding compounds of the formulae I a, Nos 1 a.1 to 1 a.695 and I b, Nos 1 b.1 to 1 b.253 only in that $(R^1)_n$ is 5-CH$_3$O-6-NH$_2$:

XVIIIa

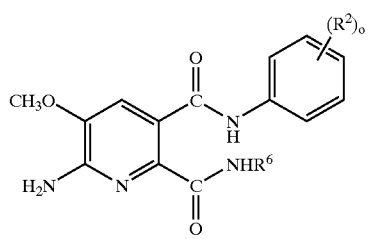

XVIIIb

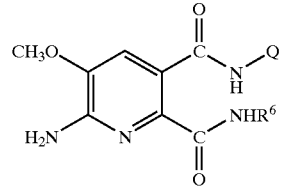

the compounds of the formulae XIX a, Nos 19 a.1 to 19 a.695, and XIX b, NOs 19 b.1 to 19 b.253, which differ from the corresponding compounds of the formulae I a, Nos 1 a.1 to 1 a.695 and I b, Nos 1 b.1 to 1 b.253 only in that $(R^1)_n$ is 5-NH$_2$-6-CH$_3$O:

XIXa

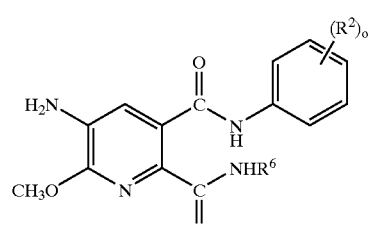

XIXb

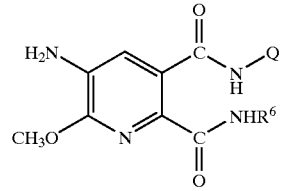

the compounds of the formulae XX a, Nos 20 a.1 to 20 a.695, and XX b, Nos 20 b.1 to 20 b.253, which differ from the corresponding compounds of the formulae I a, Nos 1 a.1 to 1 a.695 and I b, Nos 1 b.1 to 1 b.253 only in that $(R^1)_n$ is 5-CN-6-CH$_3$:

XXa

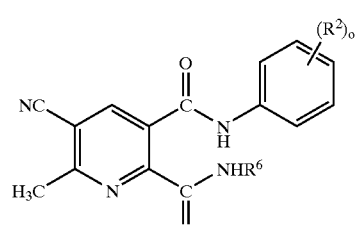

XXb

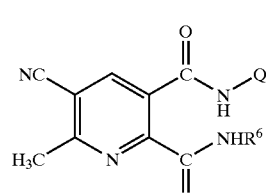

the compounds of the formulae XXI a, Nos 21 a.1 to 21 a.695, and XXI b, Nos 21 b.1 to 21 b.253, which differ from the corresponding compounds of the formulae I a, Nos 1 a.1 to 1 a.695 and I b, Nos 1 b.1 to 1 b.253 only in that $(R^1)_n$ is 5-CH$_3$-6-CN:

XXIa

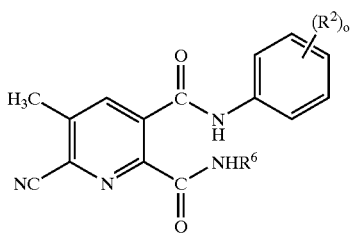

XXIb

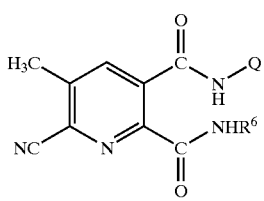

the compounds of the formulae XXII a, Nos 22 a.1 to 22 a.695, and XXII b, Nos 22 b.1 to 22 b.253, which differ from the corresponding compounds of the formulae I a, Nos 1 a.1 to 1 a.695 and I b, Nos 1 b.1 to 1 b.253 only in that $(R^1)_n$ is 4-Cl-6-NH$_2$:

XXIIa

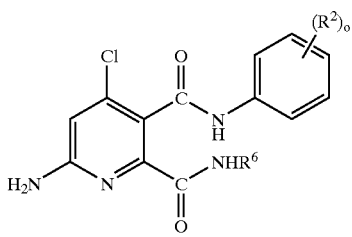

XXIIb

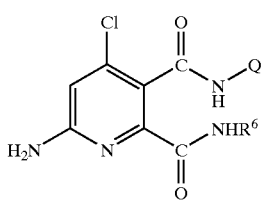

the compounds of the formulae XXIII a, Nos 23 a.1 to 23 a.695, and XXIII b, Nos 23 b.1 to 23 b.253, which differ from the corresponding compounds of the formulae I a, Nos 1 a.1 to 1 a.695 and I b, Nos 1 b.1 to 1 b.253 only in that $(R^1)_n$ is 4-NH$_2$-6-Cl:

XXIIIa

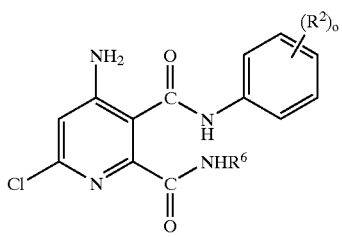

XXIIIb

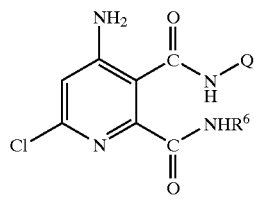

the compounds of the formulae I c, Nos 1 c.1 to 1 c.253, which differ from the corresponding compounds of the formulae I b., Nos 1 b.1 to 1 b.253 only in that $(R^1)_n$ is 6-methyl:

Ic

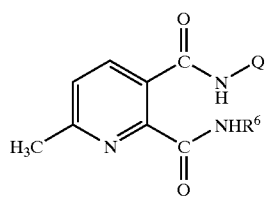

the compounds of the formulae I d, Nos 1 d.1 to 1 d.11, which differ from the corresponding compounds of the formulae I a., Nos 1 a.221 to 1 a.231 only in that $(R^1)_n$ is 6-CH$_3$:

Id

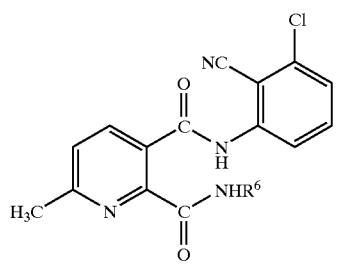

the compounds of the formulae I e, Nos 1 e.1 to 1 e.11, which differ from the corresponding compounds of the formulae I a., Nos 1 a.221 to 1 a.231 only in that $(R^1)_n$ is 6-OCH$_3$:

Ie

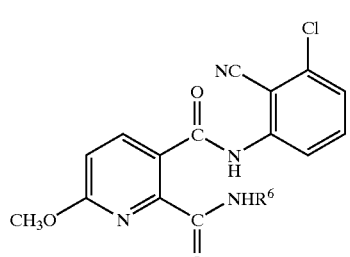

the compounds of the formulae I f, which differ from the corresponding compounds of the formula Ia, Nos Ia.364 to Ia.374 in that $(R^1)_n$ is 6-CH$_3$ and $R^{21}$ and $R^{22}$ are $R(^2)_o$ (o=2) and are as defined below:

If

| $R^{21}$ | $R^{22}$ |
|---|---|
| CN | Cl |
| $CH_3$ | $CH_3$ |
| Cl | $CF_3$ |
| $NO_2$ | $CF_3$ |
| CN | $CH_3$ |
| CN | $OCH_3$ |
| CN | $OCHF_2$ |
| CN | $CF_3$ |
| Cl | $CH_3$ |
| $CH_3$ | $OCH_3$ |
| $OCH_3$ | Cl |
| $CO_2CH_3$ | Cl |
| $CF_3$ | $CH_3$ |
| $CF_3$ | Cl |
| $CF_3$ | Br |
| $CO_2CH_3$ | $CH_3$ |
| CH=N—O—$CH_3$ | Cl |
| CH=N—O—$CH_3$ | Br |
| CH=N—O—$C_2H_5$ | Cl |
| CH=N—O—$C_2H_5$ | Cl |
| $CH_2$—O—$CH_3$ | Cl |
| $CH_2$—O—$CH_3$ | Br |
| $CH_2$—O—$C_2H_5$ | Cl |
| $CH_2$—O—$C_2H_5$ | Br | the compounds I g, which differ from the compounds Ia., Nos. Ia.685 to Ia.695 in that $(R^1)_n$ is 6-$CH_3$ and $R^{21}$, $R^{22}$ and $R^{23}$ are present for $(R^2)_o$ and are as defined below:

Ig

| $R^{21}$ | $R^{22}$ | $R^{23}$ |
|---|---|---|
| $CH_3$ | Cl | $CO_2CH_3$ |
| $CO_2CH_3$ | $CH_3$ | $CH_3$ |
| CN | Cl | $CH_3$ |
| $CO_2CH_3$ | Cl | $CH_3$ |
| $CO_2CH_3$ | Cl | Cl |
| CN | $CH_3$ | Cl |
| $CO_2CH_3$ | $CH_3$ | Cl |
| CN | Cl | Cl |
| Cl | $CH_3$ | CN |
| Cl | $CH_3$ | $CO_2CH_3$ |
| $CO_2CH_3$ | Cl | $C_2H_5$ |
| CN | $CH_3$ | $CH_3$ |
| $CO_2CH_3$ | Br | $CH_3$ |

-continued

Ig

| $R^{21}$ | $R^{22}$ | $R^{23}$ |
|---|---|---|
| $CO_2CH_3$ | Br | $C_2H_5$ |
| $C_2H_5$ | Cl | $CO_2CH_3$ |
| Cl | $CH_3$ | $CO_2CH_3$ |
| $CH_3$ | Cl | CN |
| $C_2H_5$ | Cl | CN |
| Cl | $CH_3$ | CN |
| $CO_2CH_3$ | Cl | $CO_2CH_3$ |
| $CO_2CH_3$ | Cl | $OCH_3$ |
| CN | Cl | $OCH_3$ |
| CN | Cl | $C_2H_5$ |
| $CH_2$—$OCH_3$ | Cl | $CH_3$ |
| $CH_2$—$OCH_3$ | Cl | $C_2H_5$ |
| $CH_2$—$OCH_3$ | Br | $CH_3$ |
| $CH_3$ | Cl | $CH_2$—$OCH_3$ |
| $CO_2CH_3$ | Cl | CN |
| CN | Cl | $CO_2CH_3$ |
| CN | Cl | $CH_2$—$OCH_3$ |
| CN | Br | $CH_2$—$OCH_3$ |
| $C_2H_5$ | Cl | $CH_2$—$OCH_3$ |
| $C_2H_5$ | Br | $CH_2$—$OCH_3$ |

The compounds I and their agriculturally useful salts, both as isomer mixtures and in the form of the pure isomers, are suitable as herbicides. The herbicidal compositions comprising I effect very good control of vegetation on non-crop areas, especially at high rates of application. In crops such as wheat, rice, maize, soybeans and cotton, they act against broad-leaved weeds and grass weeds without damaging the crop plants substantially. This effect is observed especially at low rates of application.

Depending on the application method in question, the compounds I, or the compositions comprising them, can additionally be employed in a further number of crop plants for eliminating undesirable plants. Suitable crops are, for example, the following: *Allium cepa, Ananas comosus, Arachis hypogaea, Asparagus officinalis, Beta vulgaris* spec. *altissima, Beta vulgaris* spec. *rapa, Brassicus napus* var. *napus, Brassicus napus* var. *napobrassica, Brassica rapa* var. *silvestris, Camellia sinensis, Carthamus tinctorius, Carya illinoinensis, citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides due to breeding, including genetic engineering methods.

The herbicidal compositions or the active ingredients can be applied pre- or post-emergence. If the active ingredients are less well tolerated by certain crop plants, it is possible to use application techniques in which the herbicidal compositions are sprayed, with the aid of the spraying equipment, in such a way that they come into as little contact as possible, if any, with the leaves of the sensitive crop plants while reaching the leaves of undesirable plants which are growing underneath, or the bare soil surface (post-directed, lay-by).

The compounds I, or the herbicidal compositions comprising them, can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol, cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the pyridine-2,3-dicarboxamides, as such or dissolved in an oil or solvent, can be homogenized in water by means of wetting agent, tackifier, dispersant or emulsifier. Alternatively, it is possible to prepare concentrates from active substances, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignin-sulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentration of the active ingredients I in the ready-to-use products can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The compounds I according to the invention can be formulated, for example, as follows:

I 20 parts by weight of the compound No. 1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II 20 parts by weight of the compound No. 4 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III 20 parts by weight of the active ingredient No. 5 are dissolved in a mixture of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of active ingredient.

IV 20 parts by weight of the active ingredient No. 9 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V 3 parts by weight of the active ingredient No. 40 are mixed with 97 parts by weight of finely divided kaolin. This gives a dust which comprises 3% by weight of the active ingredient.

VI 20 parts by weight of the active ingredient No. 50 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the active ingredient No. 51 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active ingredient No. 72 is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the spectrum of action and to achieve synergistic effects, the pyridine-2,3-dicarboxamides may be mixed, and applied jointly, with a large number of representatives of other groups of herbicidally or growth-regulating active ingredients. Suitable examples of components in mixtures are 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexandiones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halogencarboxylic acids and their derivatives, ureas, 3-phenyluracils, imidazoles, imidazolines, N-phenyl-3,4,5,6-tetrahydrophthalimides, oxadiazoles, oxirans, phenols, aryloxy- and heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, in the form of a mixture with even further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

Depending on the intended aim, the season, the target plants and the growth stage, the rates of application of active ingredient I are from 0.001 to 3.0, preferably 0.01 to 1.0 kg/ha active substance (a.s.)/ha.

The examples below illustrate the invention without limiting it.

Preparation of the Starting Materials

EXAMPLE A1

3-Chloro-2-methoxyiminomethylaniline a) 3-Chloro-2-methoxyiminomethylanilinenitrobenzene With stirring, 25.4 g (0.302 mol) of sodium bicarbonate were added a little at a time at 22° C. to a mixture of 126 g (0.302 mol) of 20% o-methylhydroxylamine hydrochloride in 140 ml of water, over a period of 10 min. This solution was then, at 50–55° C., added with stirring to 50 g of 2-chloro-6-nitrobenzaldehyde in 270 ml of toluene, over a period of 30 min, and the mixture was stirred at 50° C. for another 2 h. After cooling, 250 ml of water and 250 ml of toluene were added to the reaction mixture to separate the phases. The aqueous phase was re-extracted with toluene. The organic extracts were washed with water and diluted sodium chloride solution, dried over magnesium sulfate and concentrated under reduced pressure. This gave 52 g (84% of theory) of the title compound as a yellowish oil with $n_D^{23}$=1.5691.

b) 3-Chloro-2-methoxyiminomethylaniline 35.1 g (0.629 mol) of iron powder were initially charged in a mixture of 100 ml of acetic acid and 140 ml of methanol, and the mixture was heated to 70° C. At 70–75° C., 45 g (0.21 mol) of the compound from 1a) in 100 ml of acetic acid and 140 ml of methanol were then added with stirring over a period of 45 min, and the mixture was stirred at 70° C. for another 3 h. After cooling, the suspension was poured into 3 of water and extracted with 0.5 l of ethyl acetate. The precipitate was filtered off with suction and washed with 0.5 l of ethyl acetate, and the phases were separated. The aqueous phase was extracted two more times with ethyl acetate and the organic extracts were combined, dried over magnesium sulfate and concentrated under reduced pressure. This gave 38.7 g (95% of theory) of the title compound as a yellowish oil with $n_D^{23}$=1.6140.

EXAMPLE A2

Methyl 2-amino-6-chloro-3-methylbenzoate

At 22° C., 110 g (0.52 mol of 6-chloro-3-methylisatoic anhydride were introduced into a mixture of 750 ml of methanol and 47.6 g (0.47 mol) of triethylamine, and the mixture was then stirred at 65° C. for 2 h. The reaction mixture was concentrated under reduced pressure and the residue was taken up in methylene chloride and extracted 3 times with 0.5 N aqueous sodium hydroxide solution. The mixture was dried over magnesium sulfate, filtered through silica gel and concentrated under reduced pressure, giving 45.5 g (43.8% of theory) of the title compound as a colorless oil with $n_D^{23}$=1.5765.

EXAMPLE A3

2-Amino-3-chloro-6-methylbenzamide

Using two dropping funnels, a solution of 59 ml (0.78 mol) of a 25% strength solution of ammonia in 207 ml of water and a mixture of 135.2 g (0.64 mol) of 3-chloro-6-methylisatoic anhydride in 705 ml of DMF were added simultaneously over a period of 30 min with stirring at 85–90° C. to 150 ml of water, resulting in a strong evolution of gas. The mixture was stirred at 90° C. for 2 h and at 22° C. for 10 h. The reaction solution was concentrated under reduced pressure and the residue was triturated with methyl tert-butyl ether, filtered off with suction and dried. This gave 67.4 g (57% of theory) of the title compound as a yellowish powder of m.p. 124–128° C.

EXAMPLE A4

2-Amino-3-chloro-6-methylbenzonitrile

With stirring, 1.18 g (0.033 mol) of hydrogen chloride, dissolved in 35 ml of diethyl ether, were added to a suspension of 5 g (0.027 mol) of the compound from Example A3 in 50 ml of 1,2-dichloroethane at 22–30° C., and the mixture was then concentrated under reduced pressure. The residue was admixed with 150 ml of phosphorus oxychloride and stirred at 120° C. for 3 h. The reaction mixture was then concentrated under reduced pressure and the residue was dissolved in methylene chloride, admixed with water and neutralized using 2 N aqueous sodium hydroxide solution. Following phase separation, the mixture was once again washed with water and then with saturated sodium chloride solution and dried over magnesium sulfate. Concentration gave 2.4 g (48% of theory) of the title compound as a yellowish powder of m.p. 77–80° C.

EXAMPLE A5

2-Amino-4-chloro-3-methylbenzamide

Using two inlets, at 80° C. a suspension of 4.64 g (0.0219 mol) of 3-methyl-4-chloroisatoic anhydride in 21 ml of DMF and 3.1 g (0.0219 mol) of 25% strength ammonia water in 6 ml of water were added simultaneously with stirring and over a period of 15 min to 8 ml of water. The mixture was stirred at 80° C. for 1 h and then cooled and extracted twice with ethyl acetate. The organic phase was dried over magnesium sulfate and concentrated under reduced pressure, giving 2.61 g (64.4% of theory) of the title compound as colorless crystals of m.p. 206–208° C.

EXAMPLE A6

2-Amino-4-chloro-3-methylbenzonitrile

Using the procedure of Example A4, the reaction of 5 g (27.1 mmol) of the compound from Example A5, 1.18 g (32.5 mmol) of hydrogen chloride and 100 ml of 1,2-dichloroethane and then 150 ml of phosphorus oxychloride, 2.39 g (52.9% of theory) of the title compound were obtained as a yellowish powder of m.p. 98–99° C.

EXAMPLE A7

2-Amino-6-chloro-3-methylbenzamide

Using the procedure of Example A3, the reaction of 98.8 g (0.467 mol) of 6-chloro-3-methylisatoic anhydride in 330 ml of DMF with 42 ml (0.560 mol) of 25% strength aqueous ammonia solution in 140 ml of water and a further 110 ml of water gave 24 g (37% of theory) of the title compound as a yellowish powder of m.p. 149–152° C.

EXAMPLE A8

2-Amino-6-chloro-3-methylbenzonitrile

Using the procedure of Example A4, the reaction of 2.85 g (0.0154 mol) of the compound from Example A7, 0.68 g (0.0185 mol) of hydrogen chloride in 50 ml of 1,2-dichloroethane and then 100 ml of phosphorus oxychloride gave 1.3 g (47.5% of theory) of the title compound as a yellowish powder of m.p. 95–98° C.

EXAMPLE A9

N-(2-Carbamoyl-5-chloro-6-methylphenyl)-3-carboxy-6-methylpyridine-2-carboxamide (A) and N-(2-cyano-5-chloro-6-methyl-phenyl)-6-methylpyridine-2,3-dicarboximide (B)

2.6 g (0.141 mol) of the compound from Example A5 were added to a mixture of 2.3 g (0.0141 mol) of 6-methylpyridine-2,3-dicarboxylic anhydride and 150 ml of 1,2-dichloroethane, and the mixture was stirred at 83° C. for 15 h. 1.76 g (0.0148 mol) of thionyl chloride were then added, and the mixture was stirred at 83° C. for 16 h. 200 ml of methylene chloride and 150 ml of water were added to the reaction mixture, and the phases were separated. The insoluble residue was filtered off with suction and dried, giving 0.91 g (18.5% of theory) of title compound A as a yellowish powder of m.p. 252° C. (decomp.).

The organic phase was dried and chromatographed on silica gel, giving 1.45 g (33% of theory) of the title compound B as a tacky powder.

$^1$H-NMR (270 MHz, d$_6$-DMSO): δ8.44 (d/1H), 7.9 (d/1H) Pyr; 8.0 (d/1H), 7.8 (d/1H) Ph; 2.3 (s/3H) CH$_3$

EXAMPLE A10

N-(6-Chloro-2-cyano-3-methylphenyl)-6-methylpyridine-2,3-dicarboximide 3.1 g (18.61 mmol) of the compound from Example A4 were added to 2.9 g (17.7 mmol) of 6-methylpyridine-2,3-dicarboxylic anhydride and, after heating to 170° C., stirred as a melt for a total of 8 h. After cooling, the residue was taken up in methylene chloride, and activated carbon and magnesium sulfate were added. The mixture was filtered off with suction and chromatographed on silica gel giving, after concentration, 1.3 g (24.4% of theory) of the title compound as beige crystals of m.p. 173–176° C.

EXAMPLE A11

3-Chloro-6-methylisatoic anhydride 184 g (0.94 mol) of 3-chloro-6-methylisatin were introduced into a mixture of 750 ml of glacial acetic acid and 10 ml of conc. sulfuric acid, and the mixture was heated with stirring to 70° C. At the same temperature, 145 ml (1.279 mol) of 30% hydrogen peroxide were then introduced over a period of 30 min, and the mixture was stirred at 70–75° C. for 2 h. After cooling, the precipitate was filtered off with suction, washed with water and dried. This gave 146.6 g (73.7% of theory) as a beige powder of m.p. 248–250° C.

EXAMPLE A12

N-n-Propyl-3-(6-chloro-2-cyano-3-methylphenyl) aminocarbonyl-6-methylpyridine-2-carboxamide With stirring, 0.46 g (7.699 mmol) of n-propylamine was added at 22° C. to a mixture of 0.6 g (1.92 mmol) of the compound from Example A10 in 30 ml of tetrahydrofuran, and the mixture was stirred for 12 h. The reaction mixture was concentrated under reduced pressure and the residue was stirred with diisopropyl ether/diethyl ether 20:1. Filtration with suction and drying gave 0.6 g (82.4% of theory) of the title compound as colorless crystals of m.p. 129–131° C.

EXAMPLE A13

3-Chloro-6-methylisatin a) With stirring, 984 g (6.0 mol) of hydroxylammonium sulfate were added a little at a time, at 22° C., to a mixture of 343 g (2.0 mol) of 2-chloro-5-methylaniline in 4 l of water. 124.5 g (1.22 mol) of 96% strength sulfuric acid and 295 g (2.0 mol) of chloral were successively added dropwise with stirring, in each case over a period of 20 min, the mixture was then stirred at 50° C. for 1 h. After cooling to 22° C., the pH was adjusted to 1.8 by adding 1.2 l of 20% strength aqueous sodium hydroxide solution. The mixture was allowed to stand overnight and then extracted with methylene chloride.

b) With stirring, 36.9 g (0.173 mol) of the compound from A13a were introduced at 22 to 70° C. into a mixture of 185.2 g (1.89 mol) of conc. sulfuric acid and 12.3 g of ice, and the mixture was stirred at 80° C. for 3 h. The reaction mixture was cooled to 30° C. and stirred into 3 l of ice-water. The resulting precipitate was filtered off with suction, washed with water and dried, giving 26.3 g (73% of theory) of the title compound of m.p. 236–238° C.

EXAMPLE A14

Methyl 2-amino-3-chloro-6-methylbenzoate

With stirring, 28.8 g (0.16 mol) of 30% sodium methoxide were added at 22° C. and over a period of 10 min to a suspension of 25 g (0.128 mol) of the compound from Example A13b. After cooling to 0° C., 10.9 g (0.16 mol) of 50% hydrogen peroxide were then added with stirring at 0–5° C. over a period of 30 min, and the mixture was stirred at 22° C. for 1 h. The reaction mixture was neutralized by addition of a 1 molar solution of hydrogen chloride in ether and concentrated under reduced pressure. The residue was partitioned between methylene chloride and water and the organic phase was washed two more times with dilute sodium bicarbonate solution. The organic phase was dried over magnesium sulfate, filtered with suction through neutral alumina and concentrated. This gave 17.7 g (69.4% of theory) of the title compound as a colorless oil with $n_D^{23}$= 1.5761.

Preparation of the End Products

EXAMPLE 1

N-n-Propyl-3-(1-naphthyl)aminocarbonyl-6-methylpyridine-2-carboxamide 1.1. N-(1-Naphthyl)-3-carboxy-6-methylpyridine-2-carboxamide Over a period of 3 min, 2.6 g (18.4 mmol) of 1-naphthylamine were added with stirring at 22–27° C. to 3.0 g (18.4 mmol) of 6-methylpyridine-2,3-dicarboxylic anhydride in 100 ml of 1,2-dichloroethane, and the mixture was then stirred at 70° C. for 1 h. After cooling to 23° C., the precipitate was filtered off with suction and dried, giving 4.5 g (79.9% of theory) of the title compound of m.p. 198–200° C.

The organic filtrate gave, on concentration and trituration of the residue with diethyl ether, a further 0.8 g of the title compound.

1.2. N-(1-Naphthyl)-6-methylpyridine-2,3-dicarboximide 4.6 g (15.02 mmol) of the compound 1.1 were added to 100 ml of acetic anhydride, and the mixture was stirred at 140° C. for 1 h. The reaction mixture was concentrated under reduced pressure and the residue was taken up in methylene chloride. Extraction with saturated sodium bicarbonate solution and with water, drying over magnesium sulfate and concentration gave 4.2 g (97% of theory) of the title compound of m.p. 200–205° C.

1.3. N-n-Propyl-3-(1-naphthyl)aminocarbonyl-6-methylpyridine-2-carboxamide

At 23° C., 0.615 mg (10.41 mmol) of n-propylamine were added with stirring to 1.5 g (5.2 mmol) of the compound 1.2. in 100 ml of THF, and the mixture was stirred for 12 h. The reaction mixture was concentrated under reduced pressure, the residue was stirred with ether, filtered off with suction and dried, giving 1.5 g (83% of theory) of the title compound of m.p. 175–178° C.

EXAMPLE 2

N-n-Propyl-3-(2-methyl-3-methylthiophenyl)aminocarbonyl-6-methylpyridine-2-carboxamide 2.1 2-Methyl-3-methylthioaniline At 20° C., 4.3 g (61.81 mmol) of sodium thiomethoxide were added with stirring and ice-cooling to 10 g (53.75 mmol) of 3-bromo-2-methylaniline in 100 ml of N-methylpyrrolidine. After addition of 200 mg of copper powder, the reaction mixture was transferred into an autoclave and stirred at 240° C. for 16 h. The reaction solution was subsequently poured into 300 ml of ice-water and extracted 3× with methyl tert-butyl ether. The organic extracts were washed with water, dried and concentrated. The residue was chromatographed over silica gel using methylene chloride, giving 1.7 g (20.6% of theory) of the title compound as a colorless oil.

$^1$H-NMR (270 MHz, $d_6$-DMSO) δ (ppm) 6.9, 6.45 (m/3) Ar, 4.85 (s/2) $NH_2$, 2.35 (s/3) $SCH_3$, 2.03 (s/3) $CH_3$ 2.2 N-(2-Methyl-3-methylthiophenyl)-6-methylpyridine-2,3-dicarboximide At 22° C., 1.6 g (10.44 mmol) of the compound 2.1. were added with stirring to 1.5 g (9.079 mmol) of 6-methylpyridine-2,3-dicarboxylic anhydride in 100 ml of methylene chloride, and the mixture was stirred at 70° C. for 2 h.

The reaction mixture was concentrated under reduced pressure, stirred with ether/pentane and filtered off with suction, giving 0.2 g of N-(2-methyl-3-methylthiophenyl)-3-carboxy-6-methylpyridine-2-carboxamide of m.p. 170–172° C. At 22–28° C., 1.64 g (13.78 mmol) of thionyl chloride were added with stirring to the filtrate, and the mixture was stirred at 22° C. for another 12 h. The reaction mixture was subsequently poured into 50 ml of ice-water, and the phases were separated. The organic phase was washed successively with saturated sodium bicarbonate solution and sodium chloride solution. The organic phase was then dried over magnesium sulfate and concentrated under reduced pressure, and the residue was stirred with ether/pentane, filtered off with suction and dried, giving 1.9 g (70.2% of theory of the title compound of m.p. 192–194° C.

2.3 N-n-Propyl-3-(2-methyl)-3-methylthiophenyl) aminocarbonyl-6-methylpyridine-2-carboxamide At 22° C., 0.20 g (0.67 mmol) of N-(2-methyl-3-methylthiophenyl)-6-methylpyridine-2,3-dicarboximide in 5 ml of 1,2-dichloroethane was stirred with 0.16 g (2.68 mmol) of n-propylamine for 16 hours. The reaction mixture was extracted with 5 ml of 2 N hydrochloric acid, and the organic phase was concentrated under reduced pressure. This gave 0.239 g (100%) of the title compound. Retention time in the HPLC: 4.75 min (see Table 3).

EXAMPLE 3

N-(2-Methyl-3-methylsulfonylphenyl)-6-methylpyridine-2,3-dicarboximide

At 35–40° C., 0.75 g (11.06 mmol) of 50% strength hydrogen peroxide was added over a period of 15 minutes to a mixture of 1.5 g (5.027 mmol) of the compound of Example 2.2 in 50 ml of acetic acid, and the mixture was stirred at 40° C. for another 6 hours. The same amount of hydrogen peroxide was added, and the mixture was stirred at 40° C. for another 30 hours, during which the progress of the reaction was monitored by thin-layer chromatography. After cooling, 150 ml of water were added with stirring to the reaction mixture, and the precipitate was filtered off with suction, washed with water and dried. This gave 1.1 g (66.2% of theory) of the title compound of m.p. 237–239° C.

In addition to the compounds described above, other pyridine-2,3-dicarboxamides of the formula I which were, or can be, prepared in a similar manner are listed in Table 3 below.

The listed physical data include, in addition to the melting points, also the chromatographically determined retention times of individual compounds which were measured under the following HPLC conditions:

HPLC column: 40×2 mm Grom-Sil 8 ODS-7 pH 4 μ

Mobile phase: water, acetonitrile, 0.1% trifluoroacetic acid

Method: water→acetonitrile (0%→100%) in 6 minutes

Sample concentration: 1 mg/ml

Solvent for the sample: water/acetonitrile 1:1 (+0.1% trifluoroacetic acid)

TABLE 3

| No. | $(R^1)_n$ | Q | $R^6$ | mp. [° C.] or retention time [min] |
|---|---|---|---|---|
| 1 | 6-$CH_3$ | 1-naphthyl | n-$C_3H_7$ | 175–178 |
| 2 | 6-$CH_3$ | 2-$CH_3$-3-$SCH_3$-phenyl | n-$C_3H_7$ | 151–152 4.750 |
| 3 | 6-$CH_3$ | 2-$CH_3$-3-$SO_2CH_3$-phenyl | n-$C_3H_7$ | 180–181 4.301 |
| 4 | 5,6-$(CH_3)_2$ | 2-$CH_3$-3-Cl-phenyl | n-$C_3H_7$ | 144–148 |
| 5 | 5-$CH_3$-6-Cl | 2-$CH_3$-3-Cl-phenyl | n-$C_3H_7$ | 185–187 |
| 6 | 5,6-$(CH_3)_2$ | 2-$CH_3$-3-Cl-phenyl | n-$C_3H_7$ | 148–151 |
| 7 | 6-$CH_3$ | 5-quinolyl | n-$C_3H_7$ | 198–202 |
| 8 | 6-$CH_3$ | 5-isoquinolyl | n-$C_3H_7$ | 174–177 |
| 9 | 5-Cl-6-$CH_3O$ | 2-$CH_3$-3-Cl-phenyl | n-$C_3H_7$ | 165–166 |
| 10 | 5-Cl-6-$CH_3O$ | 2-$CH_3$-3-Cl-phenyl | i-$C_4H_9$ | 170–171 |
| 11 | 5-Cl-6-$CH_3O$ | 2-$CH_3$-3-Cl-phenyl | n-$C_4H_9$ | 165–167 |
| 12 | 5-$CH_3$-6-Cl | 2-$CH_3$-3-Cl-phenyl | i-$C_4H_9$ | 170–174 |
| 13 | 5-$CH_3$-6-Cl | 2-$CH_3$-3-Cl-phenyl | n-$C_4H_9$ | 163–166 |
| 14 | 6-$CH_3$ | 2-CN-3-Cl-phenyl | c-$C_3H_5$ | |
| 15 | 6-$CH_3$ | 2-$CH_3$-3-$SO_2CH_3$-phenyl | n-$C_4H_9$ | |
| 16 | 6-$CH_3$ | 2-$CH_3$-3-$SO_2CH_3$-phenyl | $CH_2$—$C_3H_5$ | |
| 17 | 5-$CH_3$-6-Cl | 2-$CH_3$-3-$SO_2CH_3$-phenyl | n-$C_3H_7$ | |
| 18 | 6-$CH_3$ | 2-$CH_3$-3-$SO_2CF_3$-phenyl | n-$C_3H_7$ | |
| 19 | 6-$CH_3$ | 2-$CH_3$-3-$SO_2CHF_2$-phenyl | n-$C_3H_7$ | |
| 20 | 6-$CH_3$ | 2-CHO-3-Cl-phenyl | n-$C_3H_7$ | |
| 21 | 6-$CH_3$ | 2-Cl-3-CHO-phenyl | n-$C_3H_7$ | |
| 22 | 6-$CH_3$ | 2-Cl-3-C[O]$CH_3$-phenyl | n-$C_3H_7$ | |
| 23 | 6-$CH_3$ | 2-Cl-3-C[O]$C_2H_5$-phenyl | n-$C_3H_7$ | |
| 24 | 6-$CH_3$ | 2-C[O]$CH_3$-3-Cl-phenyl | n-$C_3H_7$ | |
| 25 | 6-$CH_3$ | 2-Cl-3-$CH_3$O—N=CH-phenyl | n-$C_3H_7$ | |
| 26 | 5-$CH_3$-6-Cl | 2-Cl-3-$CH_3$O—N=CH-phenyl | n-$C_3H_7$ | |
| 27 | 5-Cl-6-$CH_3O$ | 2-Cl-3-$CH_3$O—N=CH-phenyl | n-$C_3H_7$ | |
| 28 | 6-$CH_3$ | 2-$CH_3$O—N=CH-3-Cl-phenyl | n-$C_3H_7$ | 135–138 |
| 29 | 6-$CH_3$ | 2-Cl-3-$C_2H_5$O—N=CH-phenyl | n-$C_3H_7$ | |
| 30 | 6-$CH_3$ | 2-O—$CH_2$—CH=$CH_2$-3-Cl-phenyl | n-$C_3H_7$ | |
| 31 | 6-$CH_3$ | 2-Cl-3-O—$CH_2$—CH=$CH_2$-phenyl | n-$C_3H_7$ | |
| 32 | 6-$CH_3$ | 2-O—$CH_2$—CH=CHCl-3-Cl-phenyl | n-$C_4H_9$ | |
| 33 | 6-$CH_3$ | 2-O—$CH_2$C≡CH-3-Cl-phenyl | n-$C_3H_7$ | |
| 34 | 6-$CH_3$ | 2-Cl-3-O—$CH_2$C≡CH-phenyl | n-$C_3H_7$ | |
| 35 | 5-$CH_3$-6-Cl | 2-O—$CH_2$C≡CH-3-Cl-phenyl | n-$C_3H_7$ | |
| 36 | 5-Cl-6-$CH_3O$ | 2-O—$CH_2$—C≡CH-3-Cl-phenyl | n-$C_3H_7$ | |
| 37 | 6-$CH_3$ | 2-$CH_3$-3-$SO_2CH_3$-phenyl | $(CH_2)_3$Cl | |
| 38 | 6-$CH_3$ | 2-$CH_3$-3-$SO_2CF_3$-phenyl | $(CH_2)_3$Cl | |
| 39 | 5-$CH_3$-6-$C_2H_5$ | 2-$CH_3$-3-Cl-phenyl | n-$C_3H_7$ | 135–137 |
| 40 | 5-$CH_3$-6-Cl | 2-$CH_3$-5-Cl-phenyl | n-$C_3H_7$ | 197–199 |
| 41 | 5-Cl-6-$CH_3O$ | 2-$CH_3$-3-$CF_3$-phenyl | n-$C_3H_7$ | |
| 42 | 5-$CH_3$-6-Cl | 2-$CH_3$-3-$CF_3$-phenyl | n-$C_3H_7$ | |
| 43 | 6-$CH_3$ | 2-$CH_3$O-3-Cl-phenyl | n-$C_3H_7$ | 124–125 |
| 44 | 6-$CH_3$ | 2-F-3-$CF_3$-phenyl | i-$C_4H_9$ | 3.994 |
| 45 | 6-$CH_3$ | 2,3-$(CH_3)_2$-phenyl | n-$C_4H_9$ | 3.652 |
| 46 | 6-$CH_3$ | 2,3-$(CH_3)_2$-phenyl | $CH_2$—$C_3H_5$ | 3.463 |
| 47 | 6-$CH_3$ | 1-tetralinyl | i-$C_4H_9$ | 3.885 |
| 48 | 6-$CH_3$ | 1-tetralinyl | sek-$C_4H_9$ | 3.864 |
| 49 | 6-$CH_3$ | 1-tetralinyl | $CH_2$—$C_3H_5$ | 3.740 |
| 50 | 6-$CH_3$ | 2-CN-3-Cl-phenyl | i-$C_4H_9$ | 3.607 |
| 51 | 6-$CH_3$ | 2-CN-3-Cl-phenyl | $CH_2$—$C_3H_5$ | 3.421 |

TABLE 3-continued

| No. | $(R^1)_n$ | Q | $R^6$ | mp. [° C.] or retention time [min] |
|---|---|---|---|---|
| 52 | 6-$CH_3$ | 2-CN-3-F-phenyl | i-$C_4H_9$ | 3.782 |
| 53 | 6-$CH_3$ | 2-$NO_2$-3-$CF_3$-phenyl | i-$C_4H_9$ | 4.264 |
| 54 | 6-$CH_3$ | 2-$NO_2$-3-$CF_3$-phenyl | $CH_2$—$C_3H_5$ | 4.085 |
| 55 | 6-$CH_3$ | 2-CN-3-Br-phenyl | n-$C_3H_7$ | |
| 56 | 6-$CH_3$ | 2-Cl-3-$CF_3$-phenyl | n-$C_3H_7$ | |
| 57 | 6-$CH_3$ | 2-Br-3-$CF_3$-phenyl | n-$C_3H_7$ | |
| 58 | 6-$CH_3$ | 2-$NO_2$-3-$CF_3$-phenyl | n-$C_3H_7$ | |
| 59 | 6-$CH_3$ | 2-CN-3-$CH_3$-phenyl | n-$C_3H_7$ | |
| 60 | 6-$CH_3$ | 2-CN-3-$CH_3$O-phenyl | n-$C_3H_7$ | 180–183 |
| 61 | 6-$CH_3$ | 2-CN-3-$C_2H_5$O-phenyl | n-$C_3H_7$ | |
| 62 | 6-$CH_3$ | 2-CN-3-$OCH_2$—C≡CH-phenyl | n-$C_3H_7$ | |
| 63 | 6-$CH_3$ | 2-CN-3-O—$CH_2$—CH=CHCl-phenyl | n-$C_3H_7$ | |
| 64 | 6-$CH_3$ | 2-CN-3-$OCHF_2$-phenyl | n-$C_3H_7$ | |
| 65 | 6-$CH_3$ | 2-CN-3-$CF_3$-phenyl | n-$C_3H_7$ | |
| 66 | 6-$CH_3$ | 2-CHO-3-$CF_3$-phenyl | n-$C_3H_7$ | |
| 67 | 6-$CH_3$ | 2-CHO-3-$CH_3$O-phenyl | n-$C_3H_7$ | |
| 68 | 6-$CH_3$ | 2-$CH_3$O—N=CH-3-Br-phenyl | n-$C_3H_7$ | |
| 69 | 6-$CH_3$ | 2-Cl-3-$CH_3$-phenyl | n-$C_3H_7$ | 146–150 |
| 70 | 6-$CH_3$ | 2-Br-3-$CH_3$-phenyl | n-$C_3H_7$ | |
| 71 | 6-$CH_3$ | 2-$CH_3$-3-$CH_3$O-phenyl | n-$C_3H_7$ | |
| 72 | 6-$CH_3$ | 2-$CH_3$O-3-F-phenyl | n-$C_3H_7$ | 109–111 |
| 73 | 6-$CH_3$ | 2-$CH_3$O-3-Br-phenyl | n-$C_3H_7$ | |
| 74 | 6-$CH_3$ | 2-$CH_3$O—C[O]-3-Cl-phenyl | n-$C_3H_7$ | 98–103 4.776 |
| 75 | 6-$CH_3$ | 2-$C_2H_5$O—C[O]-3-Cl-phenyl | n-$C_3H_7$ | |
| 76 | 6-$CH_3$ | 2-$CH_3$O—C[O]-3-Br-phenyl | n-$C_3H_7$ | 129–132 |
| 77 | 6-$CH_3$ | 2-$CF_3$-3-$CH_3$-phenyl | n-$C_3H_7$ | |
| 78 | 6-$CH_3$ | 2-$SO_2CH_3$-3-$CH_3$-phenyl | n-$C_3H_7$ | |
| 79 | 6-$CH_3$ | 2-$SO_2CH_3$-3-Cl-phenyl | n-$C_3H_7$ | |
| 80 | 6-$CH_3$ | 2-$SO_2CH_3$-3-Br-phenyl | n-$C_3H_7$ | |
| 81 | 6-$CH_3$ | 2-$CF_3$-3-Cl-phenyl | n-$C_3H_7$ | |
| 82 | 6-$CH_3$ | 2-benzoxazolyl | n-$C_3H_7$ | |
| 83 | 6-$CH_3$ | 2-benzthiazolyl | n-$C_3H_7$ | |
| 84 | 6-$CH_3$ | 2-$CH_3$-3-$SO_2CH_3$-phenyl | i-$C_4H_9$ | |
| 85 | 5-$CH_3$-6-Cl | 2-$CH_3$-3-$SO_2CH_3$-phenyl | n-$C_4H_9$ | |
| 86 | 5-Cl-6-$CH_3$O | 2-$CH_3$-3-$SO_2CH_3$-phenyl | n-$C_4H_9$ | |
| 87 | 6-$CH_3$ | 2-$CH_3$-3-$SO_2CF_3$-phenyl | i-$C_4H_9$ | |
| 88 | 6-$CH_3$ | 2-$CH_3$-3-$SO_2CF_3$-phenyl | $CH_2$—$C_3H_5$ | |
| 89 | 6-$CH_3$ | 2-CHO-3-Cl-phenyl | n-$C_4H_9$ | |
| 90 | 5-$CH_3$-6-Cl | 2-CHO-3-Cl-phenyl | n-$C_4H_9$ | |
| 91 | 5-Cl-6-$CH_3$O | 2-CHO-3-Cl-phenyl | n-$C_4H_9$ | |
| 92 | 6-$CH_3$ | 2-Cl-3-CHO-phenyl | n-$C_4H_9$ | |
| 93 | 6-$CH_3$ | 2-Cl-3-CHO-phenyl | $CH_2$—$C_3H_5$ | |
| 94 | 6-$CH_3$ | 2-Cl-3-C(O)$CH_3$-phenyl | n-$C_4H_9$ | |
| 95 | 6-$CH_3$ | 2-Cl-3-$CH_3$O—N=CH-phenyl | n-$C_4H_9$ | |
| 96 | 5-$CH_3$-6-Cl | 2-Cl-3-$CH_3$—O—N=CH-phenyl | $CH_2$—$C_3H_5$ | |
| 97 | 6-$CH_3$ | 2-$CH_3$O—N=CH-3-Cl-phenyl | n-$C_4H_9$ | |
| 98 | 6-$CH_3$ | 2-$CH_3$O—N=CH-3-Cl-phenyl | i-$C_4H_9$ | |
| 99 | 5-$CH_3$-6-Cl | 2-$CH_3$O—N=CH-3-Cl-phenyl | $CH_2$—$C_3H_5$ | |
| 100 | 6-$CH_3$ | 2-O—$CH_2$—CH=$CH_2$-3-Cl-phenyl | i-$C_4H_9$ | |
| 101 | 6-$CH_3$ | 2-Cl-3-O—$CH_2CH$=$CH_2$-phenyl | $CH_2$—$C_3H_5$ | |
| 102 | 6-$CH_3$ | 2-O—$CH_2$—CH=CH-Cl-3-Cl-phenyl | n-$C_4H_9$ | |
| 103 | 5-$CH_3$-6-Cl | 2-O—$CH_2$—CH=CH—Cl-3-Cl-phenyl | i-$C_4H_9$ | |
| 104 | 6-$CH_3$ | 2-O—$CH_2$—C≡CH-3-Cl-phenyl | n-$C_4H_9$ | |
| 105 | 6-$CH_3$ | 2-O—$CH_2$—C≡CH-3-Cl-phenyl | $CH_2$—$C_3H_5$ | |
| 106 | 5-Cl-6-$CH_3$O | 2-O—$CH_2$—C≡CH-3-Cl-phenyl | n-$C_4H_9$ | |
| 107 | 5-$CH_3$-6-Cl | 2-$CH_3$-3-Cl-phenyl | $CH_2$—$C_3H_5$ | |
| 108 | 5-Cl-6-$CH_3$O | 2-$CH_3$-3-$CF_3$-phenyl | n-$C_4H_9$ | |
| 109 | 5-Cl-6-$CH_3$O | 2-$CH_3$-3-$CF_3$-phenyl | $(CH_2)_3Cl$ | |
| 110 | 5-$CH_3$-6-Cl | 2-$CH_3$-3-$CF_3$-phenyl | $(CH_2)_3Cl$ | |
| 111 | 6-$CH_3$ | 2-$CH_3$O-3-Cl-phenyl | i-$C_4H_9$ | |
| 112 | 6-$CH_3$ | 2-$CH_3$O-3-Cl-phenyl | $(CH_2)_3Cl$ | |
| 113 | 6-$CH_3$ | 2-F-3-$CF_3$-phenyl | n-$C_4H_9$ | |
| 114 | 6-$CH_3$ | 2-CN-3-Br-phenyl | i-$C_4H_9$ | |

TABLE 3-continued

[Structure: pyridine ring with (R¹)n substituent, bearing C(=O)-NH-Q and C(=O)-NHR⁶ groups at adjacent positions]

| No. | (R¹)n | Q | R⁶ | mp. [° C.] or retention time [min] |
|---|---|---|---|---|
| 115 | 6-CH₃ | 2-CN-3-Br-phenyl | CH₂—C₃H₅ | |
| 116 | 6-CH₃ | 2-Cl-3-CF₃-phenyl | n-C₄H₉ | |
| 117 | 6-CH₃ | 2-Cl-3-CF₃-phenyl | CH₂—C₃H₅ | |
| 118 | 5-Cl-6-CH₃O | 2-Cl-3-CF₃-phenyl | i-C₄H₉ | |
| 119 | 6-CH₃ | 2-Br-3-CF₃-phenyl | n-C₄H₉ | |
| 120 | 6-CH₃ | 2-Br-3-CF₃-phenyl | CH₂—C₃H₅ | |
| 121 | 6-CH₃ | 2-NO₂-3-CF₃-phenyl | n-C₄H₉ | |
| 122 | 6-CH₃ | 2-NO₂-3-CF₃-phenyl | C₃H₅ | |
| 123 | 6-CH₃ | 2-CN-3-CH₃-phenyl | n-C₄H₉ | |
| 124 | 6-CH₃ | 2-CN-3-CH₃-phenyl | i-C₄H₉ | |
| 125 | 6-CH₃ | 2-CN-3-CH₃-phenyl | CH₂—C₃H₅ | |
| 126 | 5-Cl-6-CH₃ | 2-CN-3-CH₃-phenyl | n-C₄H₉ | |
| 127 | 6-CH₃ | 2-CN-3-CH₃O-phenyl | n-C₄H₉ | |
| 128 | 6-CH₃ | 2-CN-3-CH₃O-phenyl | C₃H₅ | |
| 129 | 6-CH₃ | 2-CN-3-CH₃O-phenyl | i-C₄H₉ | |
| 130 | 5-CH₃-6-Cl | 2-CN-3-CH₃O-phenyl | n-C₄H₉ | |
| 131 | 6-CH₃ | 2-CN-3-OCHF₂-phenyl | i-C₄H₉ | |
| 132 | 6-CH₃ | 2-CN-3-OCHF₂-phenyl | CH₂—C₃H₅ | |
| 133 | 5-Cl-6-CH₃O | 2-CN-3-OCHF₂-phenyl | n-C₄H₉ | |
| 134 | 5-CH₃-6-Cl | 2-CN-3-OCHF₂-phenyl | n-C₃H₇ | |
| 135 | 6-CH₃ | 2-CN-3-CF₃-phenyl | (CH₂)₃Cl | |
| 136 | 6-CH₃ | 2-CN-3-CF₃-phenyl | n-C₄H₉ | |
| 137 | 6-CH₃ | 2-CN-3-CF₃-phenyl | i-C₄H₉ | |
| 138 | 6-CH₃ | 2-CN-3-CF₃-phenyl | CH₂—C₃H₅ | |
| 139 | 5-Cl-6-CH₃O | 2-CN-3-CF₃-phenyl | n-C₃H₇ | |
| 140 | 5-CH₃-6-Cl | 2-CN-3-CF₃-phenyl | (CH₂)₃Cl | |
| 141 | 6-CH₃ | 2-CHO-3-CF₃-phenyl | n-C₄H₉ | |
| 142 | 6-CH₃ | 2-CHO-3-CF₃-phenyl | (CH₂)₃Cl | |
| 143 | 6-CH₃ | 2-CHO-3-CF₃-phenyl | i-C₄H₉ | |
| 144 | 6-CH₃ | 2-CHO-3-CF₃-phenyl | CH₂—C₃H₅ | |
| 145 | 5-CH₃-6-Cl | 2-CHO-3-CF₃-phenyl | n-C₃H₇ | |
| 146 | 6-CH₃ | 2-CHO-3-CH₃O-phenyl | n-C₄H₉ | |
| 147 | 6-CH₃ | 2-CHO-3-CH₃O-phenyl | i-C₄H₉ | |
| 148 | 6-CH₃ | 2-CHO-3-CH₃O-phenyl | CH₂—C₃H₅ | |
| 149 | 5-CH₃-6-Cl | 2-CHO-3-CH₃O-phenyl | (CH₂)₃Cl | |
| 150 | 5-Cl-6-CH₃O | 2-CHO-3-CH₃O-phenyl | n-C₃H₇ | |
| 151 | 6-CH₃ | 2-CH₃ON=CH-3-Br-phenyl | n-C₄H₉ | |
| 152 | 6-CH₃ | 2-CH₃ON=CH-3-Br-phenyl | i-C₄H₉ | |
| 153 | 6-CH₃ | 2-CH₃ON=CH-3-Br-phenyl | CH₂—C₃H₅ | |
| 154 | 6-CH₃ | 2-CH₃ON=CH-3-Br-phenyl | (CH₂)₃Cl | |
| 155 | 6-CH₃ | 2-Cl-3-CH₃-phenyl | n-C₄H₉ | |
| 156 | 6-CH₃ | 2-Cl-3-CH₃-phenyl | i-C₄H₉ | |
| 157 | 5-Cl-6-CH₃O | 2-Cl-3-CH₃-phenyl | C₃H₅ | |
| 158 | 6-CH₃ | 2-Br-3-CH₃-phenyl | n-C₄H₉ | |
| 159 | 6-CH₃ | 2-Br-3-CH₃-phenyl | CH₂—C₃H₅ | |
| 160 | 5-CH₃-6-Cl | 2-Br-3-CH₃-phenyl | (CH₂)₃Cl | |
| 161 | 6-CH₃ | 2-CH₃-3-CH₃O-phenyl | n-C₄H₉ | 149–151 4.771 |
| 162 | 6-CH₃ | 2-CH₃-3-CH₃O-phenyl | i-C₄H₉ | |
| 163 | 5-CH₃-6-Cl | 2-CH₃-3-CH₃O-phenyl | C₃H₅ | |
| 164 | 6-CH₃ | 2-CH₃O-3-Br-phenyl | n-C₄H₉ | |
| 165 | 6-CH₃ | 2-CH₃O-3-Br-phenyl | CH₂—C₃H₅ | |
| 166 | 5-Cl-6-CH₃O | 2-CH₃O-3-Br-phenyl | n-C₃H₇ | |
| 167 | 6-CH₃ | 2-CF₃-3-CH₃-phenyl | (CH₂)₃Cl | |
| 168 | 6-CH₃ | 2-CF₃-3-CH₃-phenyl | n-C₄H₉ | |
| 169 | 6-CH₃ | 2-CF₃-3-CH₃-phenyl | i-C₄H₉ | |
| 170 | 6-CH₃ | 2-SO₂CH₃-3-CH₃-phenyl | n-C₄H₉ | |
| 171 | 6-CH₃ | 2-SO₂CH₃-3-CH₃-phenyl | (CH₂)₃Cl | |
| 172 | 5-Cl-6-CH₃O | 2-SO₂CH₃-3-CH₃-phenyl | i-C₄H₉ | |
| 173 | 6-CH₃ | 2-SO₂CH₃-3-Cl-phenyl | n-C₄H₉ | |
| 174 | 6-CH₃ | 2-SO₂CH₃-3-Cl-phenyl | CH₂—C₃H₅ | |
| 175 | 6-CH₃ | 2-SO₂CH₃-3-Cl-phenyl | (CH₂)₃Cl | |
| 176 | 5-CH₃-6-Cl | 2-SO₂CH₃-3-Cl-phenyl | n-C₄H₉ | |
| 177 | 6-CH₃ | 2-CF₃-3-Cl-phenyl | n-C₄H₉ | |

TABLE 3-continued

| No. | $(R^1)_n$ | Q | $R^6$ | mp. [° C.] or retention time [min] |
|---|---|---|---|---|
| 178 | 6-CH$_3$ | 2-CF$_3$-3-Cl-phenyl | i-C$_4$H$_9$ | |
| 179 | 6-CH$_3$ | 2-CF$_3$-3-Cl-phenyl | CH$_2$—C$_3$H$_5$ | |
| 180 | 5-CH$_3$-6-Cl | 2-CF$_3$-3-Cl-phenyl | n-C$_3$H$_7$ | |
| 181 | 6-CH$_3$ | 2-CN-3-Cl-phenyl | n-C$_3$H$_7$ | 176–178 4.654 |
| 182 | 5-CH$_3$-6-Cl | 2-CN-3-Cl-phenyl | n-C$_3$H$_7$ | 172–173 |
| 183 | 5-CH$_3$-6-Cl | 2-CH$_3$-3-CN-phenyl | n-C$_3$H$_7$ | 207–209 |
| 184 | 4,6-Cl$_2$-5-CH$_3$ | 2-CH$_3$-3-Cl-phenyl | n-C$_3$H$_7$ | 217–220 5.144 |
| 185 | 6-CH$_3$ | 2,3,6-(CH$_3$)$_3$-phenyl | n-C$_3$H$_7$ | 124–126 |
| 186 | 6-CH$_3$ | 2-CH$_3$O-3-F-phenyl | n-C$_3$H$_7$ | 109–111 |
| 187 | 6-CH$_3$ | 2-CN-3-Cl-phenyl | n-C$_3$H$_7$ | 176–178 |
| 188 | 6-CH$_3$ | 2,3,6-(CH$_3$)$_3$-phenyl | CH$_2$-c-C$_3$H$_5$ | |
| 189 | 6-CH$_3$ | 2,3,6-(CH$_3$)$_3$-phenyl | i-C$_4$H$_9$ | |
| 190 | 6-CH$_3$ | 2,3,6-(CH$_3$)$_3$-phenyl | sec-C$_4$H$_9$ | |
| 191 | 6-CH$_3$ | 2-CH$_3$O—CO-3-CH$_3$-phenyl | n-C$_3$H$_7$ | 130–131 |
| 192 | 6-CH$_3$ | 2-CH$_3$O—CO-3-CH$_3$-phenyl | CH$_2$-c-C$_3$H$_5$ | 137–139 |
| 193 | 6-CH$_3$ | 2-CH$_3$O—CO-3-CH$_3$-phenyl | i-C$_4$H$_9$ | |
| 194 | 6-CH$_3$ | 2-CH$_3$O—CO-3-CH$_3$-phenyl | sec-C$_4$H$_9$ | |
| 195 | 6-CH$_3$ | 2-CH$_3$-3-Cl-6-CH$_3$NH—CO-phenyl | n-C$_3$H$_7$ | 225–228 |
| 196 | 6-CH$_3$ | 2-CH$_3$-3-Cl-6-CN-phenyl | n-C$_3$H$_7$ | 174–175 |
| 197 | 6-CH$_3$ | 2-CH$_3$-3-Cl-6-CN-phenyl | CH$_2$-c-C$_3$H$_5$ | 188–190 |
| 198 | 6-CH$_3$ | 2-CH$_3$-3-Cl-6-CN-phenyl | i-C$_4$H$_9$ | |
| 199 | 6-CH$_3$ | 2-CH$_3$-3-Cl-6-CN-phenyl | sec-C$_4$H$_9$ | |
| 200 | 6-CH$_3$ | 2-CN-3-Cl-phenyl | sec-C$_4$H$_9$ | |
| 201 | 6-CH$_3$ | 2-CH$_3$O—CO-3,6-(CH$_3$)$_2$-phenyl | n-C$_3$H$_7$ | 128–131 |
| 202 | 6-CH$_3$ | 2-CH$_3$O—CO-3,6-(CH$_3$)$_2$-phenyl | n-C$_4$H$_9$ | |
| 203 | 6-CH$_3$ | 2-CH$_3$O—CO-3,6-(CH$_3$)$_2$-phenyl | CH$_2$-c-C$_3$H$_5$ | 158–161 |
| 204 | 6-CH$_3$ | 2-CF$_3$-3-Cl-phenyl | n-C$_3$H$_7$ | 122–123 |
| 205 | 6-CH$_3$ | 2-CH$_3$O-3-Cl-phenyl | sec-C$_4$H$_9$ | |
| 206 | 6-CH$_3$ | 2,2-difluorobenzodioxol-4-yl | n-C$_3$H$_7$ | 127–130 |
| 207 | 6-CH$_3$ | 2,2-difluorobenzodioxol-4-yl | (CH$_2$)$_3$Cl | |
| 208 | 6-CH$_3$ | 2-CH$_3$O—CO-3-Cl-phenyl | 1-cyclopropyl-ethyl | 113–115 |
| 209 | 6-CH$_3$ | 2-CH$_3$O—CO-3-Cl-phenyl | i-C$_4$H$_9$ | |
| 210 | 6-CH$_3$ | 2-CH$_3$O—CO-3-Cl-phenyl | n-C$_4$H$_9$ | |
| 211 | 6-CH$_3$ | 2-CH$_3$O—CO-3-Cl-phenyl | sec-C$_4$H$_9$ | |
| 212 | 6-CH$_3$ | 2-CH$_3$O—CO-3-Cl-phenyl | CH$_2$-c-C$_3$H$_5$ | 120–122 |
| 213 | 6-CH$_3$ | 2-CH$_3$O—CO-3,6-(CH$_3$)$_2$-phenyl | 1-cyclopropyl-ethyl | |
| 214 | 6-CH$_3$ | 2-CH$_3$O—CO-3,6-(CH$_3$)$_2$-phenyl | (CH$_2$)$_3$Cl | |
| 215 | 6-CH$_3$ | 2-CH$_3$O—CO-3,6-(CH$_3$)$_2$-phenyl | sec-C$_4$H$_9$ | |
| 216 | 6-CH$_3$ | 2-CN-3-Cl-6-CH$_3$-phenyl | CH$_2$-c-C$_3$H$_5$ | 160–165 |
| 217 | 6-CH$_3$ | 2-CN-3-Cl-6-CH$_3$-phenyl | n-C$_3$H$_7$ | 202–204 |
| 218 | 6-CH$_3$ | 2-CN-3-Cl-6-CH$_3$-phenyl | n-C$_4$H$_9$ | |
| 219 | 6-CH$_3$ | 2-CN-3-Cl-6-CH$_3$-phenyl | i-C$_4$H$_9$ | |
| 220 | 6-CH$_3$ | 2-CN-3-Cl-6-CH$_3$-phenyl | sec-C$_4$H$_9$ | |
| 221 | 6-CH$_3$ | 2-CN-3-Cl-6-CH$_3$-phenyl | (CH$_2$)$_3$Cl | |
| 222 | 6-CH$_3$ | 2-NH$_2$—CO-3-Cl-6-CH$_3$-phenyl | CH$_2$-c-C$_3$H$_5$ | 240–242 |
| 223 | 6-CH$_3$ | 2-NH$_2$—CO-3-Cl-6-CH$_3$-phenyl | n-C$_3$H$_7$ | 241–243 |
| 224 | 6-CH$_3$ | 2-CH$_3$O—N=CH-3-Cl-phenyl | CH$_2$-c-C$_3$H$_5$ | 118–120 |
| 225 | 6-CH$_3$ | 2-CH$_3$O—N=CH-3-Cl-phenyl | (CH$_2$)$_3$Cl | |
| 226 | 6-CH$_3$ | 2-CH$_3$-3-Cl-6-CH$_3$O—CO-phenyl | n-C$_3$H$_7$ | 155–158 decomp. |
| 227 | 6-CH$_3$ | 2-CH$_3$-3-Cl-6-CH$_3$O—CO-phenyl | n-C$_4$H$_9$ | |
| 228 | 6-CH$_3$ | 2-CH$_3$-3-Cl-6-CH$_3$O—CO-phenyl | sec-C$_4$H$_9$ | |
| 229 | 6-CH$_3$ | 2-CH$_3$-3-Cl-6-CH$_3$O—CO-phenyl | i-C$_4$H$_9$ | |
| 230 | 6-CH$_3$ | 2-CH$_3$-3-Cl-6-CH$_3$O—CO-phenyl | CH$_2$-c-C$_3$H$_5$ | 129–133 decomp. |
| 231 | 6-CH$_3$ | 2-CH$_3$-3-Cl-6-CH$_3$O—CO-phenyl | C$_3$H$_5$ | |
| 232 | 6-CH$_3$ | 2-CH$_3$-3-Cl-6-CH$_3$O—CO-phenyl | 1-cyclopropyl-ethyl | |
| 233 | 6-CH$_3$ | 2-CH$_3$O—(CO)-3-Cl-6-CH$_3$-phenyl | n-C$_3$H$_7$ | 160–163 |
| 234 | 6-CH$_3$ | 2-CH$_3$O—(CO)-3-Cl-6-CH$_3$-phenyl | n-C$_4$H$_9$ | |

TABLE 3-continued

| No. | $(R^1)_n$ | Q | $R^6$ | mp. [° C.] or retention time [min] |
|---|---|---|---|---|
| 235 | 6-CH$_3$ | 2-CH$_3$O—(CO)-3-Cl-6-CH$_3$-phenyl | sec-C$_4$H$_9$ | |
| 236 | 6-CH$_3$ | 2-CH$_3$O—(CO)-3-Cl-6-CH$_3$-phenyl | i-C$_4$H$_9$ | |
| 237 | 6-CH$_3$ | 2-CH$_3$O—(CO)-3-Cl-6-CH$_3$-phenyl | CH$_2$-c-C$_3$H$_5$ | 168–169 |
| 238 | 6-CH$_3$ | 2-CH$_3$O—(CO)-3-Cl-6-CH$_3$-phenyl | (CH$_2$)$_3$Cl | |
| 239 | 6-CH$_3$ | 2-CH$_3$O—(CO)-3,6-(Cl$_2$)-phenyl | n-C$_3$H$_7$ | |
| 240 | 6-CH$_3$ | 2-CH$_3$O—(CO)-3,6-(Cl$_2$)-phenyl | CH$_2$-c-C$_3$H$_5$ | |
| 241 | 6-CH$_3$ | 2-CN-3-CH$_3$-6-Cl-phenyl | n-C$_3$H$_7$ | 129–131 |
| 242 | 6-CH$_3$ | 2-CN-3-CH$_3$-6-Cl-phenyl | n-C$_4$H$_9$ | |
| 243 | 6-CH$_3$ | 2-CN-3-CH$_3$-6-Cl-phenyl | sec-C$_4$H$_9$ | |
| 244 | 6-CH$_3$ | 2-CN-3-CH$_3$-6-Cl-phenyl | CH$_2$-c-C$_3$H$_5$ | 131–133 |
| 245 | 6-CH$_3$ | 2-CN-3-CH$_3$-6-Cl-phenyl | i-C$_4$H$_9$ | |
| 246 | 6-CH$_3$ | 2-CN-3-CH$_3$-6-Cl-phenyl | (CH$_2$)$_3$Cl | |
| 247 | 6-CH$_3$ | 2-CH$_3$O—(CO)-3-CH$_3$-6-Cl-phenyl | n-C$_3$H$_7$ | |
| 248 | 6-CH$_3$ | 2-CH$_3$O—(CO)-3-CH$_3$-6-Cl-phenyl | n-C$_4$H$_9$ | |
| 249 | 6-CH$_3$ | 2-CH$_3$O—(CO)-3-CH$_3$-6-Cl-phenyl | CH$_2$-c-C$_3$H$_5$ | |
| 250 | 6-CH$_3$ | 2-CN-3,6-(Cl$_2$)-phenyl-phenyl | n-C$_3$H$_7$ | |
| 251 | 6-CH$_3$ | 2-CN-3,6-(Cl$_2$)-phenyl | CH$_2$-c-C$_3$H$_5$ | |
| 252 | 6-CH$_3$ | 2-Cl-3-CH$_3$-6-CN-phenyl | n-C$_3$H$_7$ | |
| 253 | 6-CH$_3$ | 2-Cl-3-CH$_3$-6-CN-phenyl | n-C$_4$H$_9$ | |
| 254 | 6-CH$_3$ | 2-Cl-3-CH$_3$-6-CN-phenyl | CH$_2$-c-C$_3$H$_5$ | |
| 255 | 6-CH$_3$ | 2-Cl-3-CH$_3$-6-CH$_3$O—(CO)-phenyl | n-C$_3$H$_7$ | |
| 256 | 6-CH$_3$ | 2-Cl-3-CH$_3$-6-CH$_3$O—(CO)-phenyl | CH$_2$-c-C$_3$H$_5$ | |
| 257 | 6-CH$_3$ | 2-CH$_3$O—(CO)-3-Cl-6-C$_2$H$_5$-phenyl | n-C$_3$H$_7$ | |
| 258 | 6-CH$_3$ | 2-CH$_3$O—(CO)-3-Cl-6-C$_2$H$_5$-phenyl | n-C$_4$H$_9$ | |
| 259 | 6-CH$_3$ | 2-CH$_3$O—(CO)-3-Cl-6-C$_2$H$_5$-phenyl | i-C$_4$H$_9$ | |
| 260 | 6-CH$_3$ | 2-CH$_3$O—(CO)-3-Cl-6-C$_2$H$_5$-phenyl | sec-C$_4$H$_9$ | |
| 261 | 6-CH$_3$ | 2-CH$_3$O—(CO)-3-Cl-6-C$_2$H$_5$-phenyl | CH$_2$-c-C$_3$H$_5$ | |
| 262 | 6-CH$_3$ | 2-CH$_3$O—(CO)-3-Cl-6-C$_2$H$_5$-phenyl | (CH$_2$)$_3$Cl | |
| 263 | 6-CH$_3$ | 2-CH$_3$O—(CO)-3-Br-6-CH$_3$-phenyl | n-C$_3$H$_7$ | |
| 264 | 6-CH$_3$ | 2-CH$_3$O—(CO)-3-Br-6-CH$_3$-phenyl | n-C$_4$H$_9$ | |
| 265 | 6-CH$_3$ | 2-CH$_3$O—(CO)-3-Br-6-CH$_3$-phenyl | CH$_2$-c-C$_3$H$_5$ | |
| 266 | 6-CH$_3$ | 2-CH$_3$O—(CO)-3-Br-6-CH$_3$-phenyl | (CH$_2$)$_3$Cl | |
| 267 | 6-CH$_3$ | 2-CH$_3$O—(CO)-3-Br-6-CH$_3$-phenyl | i-C$_4$H$_9$ | |
| 268 | 6-CH$_3$ | 2-CH$_3$O—(CO)-3-Br-6-C$_2$H$_5$-phenyl | n-C$_3$H$_7$ | |
| 269 | 6-CH$_3$ | 2-CH$_3$O—(CO)-3-Br-6-C$_2$H$_5$-phenyl | n-C$_4$H$_9$ | |
| 270 | 6-CH$_3$ | 2-CH$_3$O—(CO)-3-Br-6-C$_2$H$_5$-phenyl | CH$_2$-c-C$_3$H$_5$ | |
| 271 | 6-CH$_3$ | 2-CH$_3$O—(CO)-3-Br-6-C$_2$H$_5$-phenyl | i-C$_4$H$_9$ | |
| 272 | 6-CH$_3$ | 2-CH$_3$O—(CO)-3-Br-6-C$_2$H$_5$-phenyl | sec-C$_4$H$_9$ | |
| 273 | 6-CH$_3$ | 2-CH$_3$O—(CO)-3-Br-6-C$_2$H$_5$-phenyl | (CH$_2$)$_3$Cl | |
| 274 | 6-CH$_3$ | 2-C$_2$H$_5$-3-Cl-6-CH$_3$O—(CO)-phenyl | n-C$_3$H$_7$ | |
| 275 | 6-CH$_3$ | 2-C$_2$H$_5$-3-Cl-6-CH$_3$O—(CO)-phenyl | CH$_2$-c-C$_3$H$_5$ | |
| 276 | 6-CH$_3$ | 2-Cl-3-CH$_3$-6-CH$_3$O—(CO)-phenyl | n-C$_3$H$_7$ | |
| 277 | 6-CH$_3$ | 2-Cl-3-CH$_3$-6-CH$_3$O—(CO)-phenyl | CH$_2$-c-C$_3$H$_5$ | |
| 278 | 6-CH$_3$ | 2-Br-3-Cl-6-CH$_3$O—(CO)-phenyl | n-C$_3$H$_7$ | |
| 279 | 6-CH$_3$ | 2-Br-3-Cl-6-CH$_3$O—(CO)-phenyl | CH$_2$-c-C$_3$H$_5$ | |
| 280 | 6-CH$_3$ | 2-C$_2$H$_5$-3-Cl-6-CN-phenyl | n-C$_3$H$_7$ | |
| 281 | 6-CH$_3$ | 2-C$_2$H$_5$-3-Cl-6-CN-phenyl | CH$_2$-c-C$_3$H$_5$ | |
| 282 | 6-CH$_3$ | 2-C$_2$H$_5$-3-Cl-6-CN-phenyl | n-C$_4$H$_9$ | |
| 283 | 6-CH$_3$ | 2-C$_2$H$_5$-3-Cl-6-CN-phenyl | i-C$_4$H$_9$ | |
| 284 | 6-CH$_3$ | 2-C$_2$H$_5$-3-Cl-6-CN-phenyl | (CH$_2$)$_3$Cl | |
| 285 | 6-CH$_3$ | 2-CH$_3$-3-Cl-6-CN-phenyl | n-C$_4$H$_9$ | |
| 286 | 6-CH$_3$ | 2-CH$_3$-3-Cl-6-CN-phenyl | (CH$_2$)$_3$Cl | |
| 287 | 6-CH$_3$ | 2-Cl-3-CH$_3$-6-CN-phenyl | n-C$_3$H$_7$ | |
| 288 | 6-CH$_3$ | 2-Cl-3-CH$_3$-6-CN-phenyl | CH$_2$-c-C$_3$H$_5$ | |
| 289 | 6-CH$_3$ | 2,3-Cl$_2$-6-CN-phenyl | n-C$_3$H$_7$ | |
| 290 | 6-CH$_3$ | 2,3-(CH$_3$)$_2$-6-CN-phenyl | n-C$_3$H$_7$ | |
| 291 | 6-CH$_3$ | 2,6-[CH$_3$O—(CO)]$_2$-3-Cl-phenyl | n-C$_3$H$_7$ | |
| 292 | 6-CH$_3$ | 2,6-[CH$_3$O—(CO)]$_2$-3-Cl-phenyl | CH$_2$-c-C$_3$H$_5$ | |
| 293 | 6-CH$_3$ | 2-CH$_3$O—(CO)-3-Cl-6-CH$_3$O-phenyl | n-C$_3$H$_7$ | |

TABLE 3-continued $$\text{(structure shown: pyridine ring with } (R^1)_n, \text{ C(O)NH-Q, and C(O)NHR}^6 \text{ substituents)}$$

| No. | $(R^1)_n$ | Q | $R^6$ | mp. [° C.] or retention time [min] |
|---|---|---|---|---|
| 294 | 6-CH₃ | 2-CH₃O—(CO)-3-Cl-6-CH₃O-phenyl | CH₂-c-C₃H₅ | |
| 295 | 6-CH₃ | 2-CN-3-Cl-6-CH₃O-phenyl | n-C₃H₇ | |
| 296 | 6-CH₃ | 2-CN-3-Cl-6-CH₃O-phenyl | n-C₄H₉ | |
| 297 | 6-CH₃ | 2-CN-3-Cl-6-CH₃O-phenyl | i-C₄H₉ | |
| 298 | 6-CH₃ | 2-CN-3-Cl-6-CH₃O-phenyl | sec-C₄H₉ | |
| 299 | 6-CH₃ | 2-CN-3-Cl-6-CH₃O-phenyl | CH₂-c-C₃H₅ | |
| 300 | 6-CH₃ | 2-CN-3-Cl-6-CH₃O-phenyl | (CH₂)₃Cl | |
| 301 | 6-CH₃ | 2-CH₃OCH₂-3-Cl-6-CH₃-phenyl | n-C₃H₇ | |
| 302 | 6-CH₃ | 2-CH₃OCH₂-3-Cl-6-CH₃-phenyl | n-C₄H₉ | |
| 303 | 6-CH₃ | 2-CH₃OCH₂-3-Cl-6-CH₃-phenyl | i-C₄H₉ | |
| 304 | 6-CH₃ | 2-CH₃OCH₂-3-Cl-6-CH₃-phenyl | sec-C₄H₉ | |
| 305 | 6-CH₃ | 2-CH₃OCH₂-3-Cl-6-CH₃-phenyl | CH₂-c-C₃H₅ | |
| 306 | 6-CH₃ | 2-CH₃OCH₂-3-Cl-6-CH₃-phenyl | (CH₂)₃Cl | |
| 307 | 6-CH₃ | 2-CH₃OCH₂-3-Cl-6-C₂H₅-phenyl | n-C₃H₇ | |
| 308 | 6-CH₃ | 2-CH₃OCH₂-3-Cl-6-C₂H₅-phenyl | n-C₄H₉ | |
| 309 | 6-CH₃ | 2-CH₃OCH₂-3-Cl-6-C₂H₅-phenyl | i-C₄H₉ | |
| 310 | 6-CH₃ | 2-CH₃OCH₂-3-Cl-6-C₂H₅-phenyl | sec-C₄H₉ | |
| 311 | 6-CH₃ | 2-CH₃OCH₂-3-Cl-6-C₂H₅-phenyl | CH₂-c-C₃H₅ | |
| 312 | 6-CH₃ | 2-CH₃OCH₂-3-Cl-6-C₂H₅-phenyl | (CH₂)₃Cl | |
| 313 | 6-CH₃ | 2-CH₃OCH₂-3-Br-6-CH₃-phenyl | n-C₃H₇ | |
| 314 | 6-CH₃ | 2-CH₃OCH₂-3-Br-6-CH₃-phenyl | CH₂C(CH₃)=CH₂ | |
| 315 | 6-CH₃ | 2-CH₃OCH₂-3-Br-6-CH₃-phenyl | n-C₄H₉ | |
| 316 | 6-CH₃ | 2-CH₃OCH₂-3-Br-6-CH₃-phenyl | i-C₄H₉ | |
| 317 | 6-CH₃ | 2-CH₃OCH₂-3-Br-6-CH₃-phenyl | sec-C₄H₉ | |
| 318 | 6-CH₃ | 2-CH₃OCH₂-3-Br-6-CH₃-phenyl | CH₂-c-C₃H₅ | |
| 319 | 6-CH₃ | 2-CH₃OCH₂-3-Br-6-CH₃-phenyl | (CH₂)₃Cl | |
| 320 | 6-CH₃ | 2-CH₃-3-Cl-6-CH₂OCH₃-phenyl | n-C₃H₇ | |
| 321 | 6-CH₃ | 2-CH₃-3-Cl-6-CH₂OCH₃-phenyl | n-C₄H₉ | |
| 322 | 6-CH₃ | 2-CH₃-3-Cl-6-CH₂OCH₃-phenyl | i-C₄H₉ | |
| 323 | 6-CH₃ | 2-CH₃-3-Cl-6-CH₂OCH₃-phenyl | sec-C₄H₉ | |
| 324 | 6-CH₃ | 2-CH₃-3-Cl-6-CH₂OCH₃-phenyl | CH₂-c-C₃H₅ | |
| 325 | 6-CH₃ | 2-CH₃-3-Cl-6-CH₂OCH₃-phenyl | (CH₂)₃Cl | |
| 326 | 6-CH₃ | 2-CH₃O—(CO)-3-Cl-6-CN-phenyl | n-C₃H₇ | |
| 327 | 6-CH₃ | 2-CH₃O—(CO)-3-Cl-6-CN-phenyl | CH₂-c-C₃H₅ | |
| 328 | 6-CH₃ | 2-CN-3-Cl-6-CH₃O(CO)-phenyl | n-C₃H₇ | |
| 329 | 6-CH₃ | 2-CN-3-Cl-6-CH₃O(CO)-phenyl | CH₂-c-C₃H₅ | |
| 330 | 6-CH₃ | 2-CH=N—OCH₃-3-Cl-6-CH₃-phenyl | n-C₃H₇ | |
| 331 | 6-CH₃ | 2-CH=N—OCH₃-3-Cl-6-CH₃-phenyl | n-C₄H₉ | |
| 332 | 6-CH₃ | 2-CH=N—OCH₃-3-Cl-6-CH₃-phenyl | i-C₄H₉ | |
| 333 | 6-CH₃ | 2-CH=N—OCH₃-3-Cl-6-CH₃-phenyl | sec-C₄H₉ | |
| 334 | 6-CH₃ | 2-CH=N—OCH₃-3-Cl-6-CH₃-phenyl | (CH₂)₃Cl | |
| 335 | 6-CH₃ | 2-CH=N—OCH₃-3-Cl-6-CH₃-phenyl | CH₂-c-C₃H₅ | |
| 336 | 6-CH₃ | 2-CN-5-Cl-6-CH₃-phenyl | n-C₃H₇ | 175–176 |
| 337 | 6-CH₃ | 2-CH₃O—C(O)-3-Br-phenyl | CH₂-c-C₃H₅ | 136–138 |
| 338 | 6-CH₃ | 2-CH₃O—C(O)-3-Br-phenyl | n-C₄H₉ | |
| 339 | 6-CH₃ | 2-CH₃O—C(O)-3-Br-phenyl | i-C₄H₉ | |

EXAMPLE 336

N-n-Propyl 3-(2-cyano-5-chloro-6-methylphenyl)aminocarbonyl-6-methylpyridine-2-carboxamide 0.28 g (4.8 mmol) of n-propylamine was added to a mixture of 0.5 g (1.604 mmol) of the compound B from Example A9 and 20 ml of THF, and the mixture was stirred at 22° C. for 14 h. The reaction mixture was concentrated under reduced pressure, stirred into methylene chloride and washed twice with 0.5 N aqueous sodium hydroxide solution. The organic phase was dried and concentrated, giving 0.2 g (30.3% of theory) of the title compound as a yellowish powder of m.p. 175–176° C.

USE EXAMPLES

The herbicidal action of the pyridine-2,3-dicarboxamides of the formula I was examined in greenhouse experiments:

The growing containers used were plastic pots containing loamy sand with approximately 3.0% of humus as the substrate. The seeds of the test plants were sown separately for each species.

In the pre-emergence treatment, the active ingredients which had been suspended or emulsified in water were applied immediately after sowing by means of finely distributing nozzles. The containers were irrigated lightly to promote germination and growth and subsequently covered with transparent plastic hoods until the plants had rooted. This cover causes uniform germination of the test plants, unless this was adversely affected by the active ingredients.

For the post-emergence treatment, the test plants were first grown to a plant height of 3 to 15 cm, depending on the growth habit, and then treated with the active ingredients which had been suspended or emulsified in water. The test plants were either sown directly and grown in the same containers or first grown separately as seedlings and transplanted into the test containers a few days prior to treatment. The rate of application for the post-emergence treatment was 0.5; 0.0625; 0.0313 or 0.0156 kg/ha of a.s.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants or complete destruction of at least the above-ground parts, and 0 means no damage or normal course of growth.

The plants used in the greenhouse experiments belonged to the following species:

| Common name | Code |
| --- | --- |
| lambsquarters (goosefoot) | CHEAL |
| catchweed bedstraw | GALAP |
| black nightshade | SOLNI |
| speedwell | VERSS |
| redroot pigweed | AMARE |
| barnyard grass | ECGCG |
| morning glory | IPOSS |
| violet | VIOAR |
| blackgrass | ALOMY |
| soybeans | GLXMA |

TABLE 4

Herbicidal activity when used post-emergence in a greenhouse

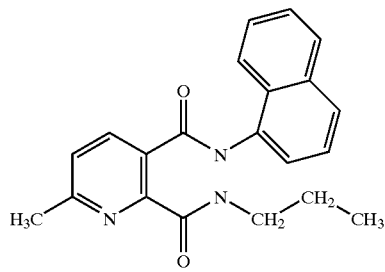

| | Application rate (kg of a.s./ha) | |
| --- | --- | --- |
| Test plants | 0.0625 | 0.0313 |
| AMARE | 100 | 98 |
| ALOMY | 85 | 75 |
| IPOSS | 100 | 98 |

TABLE 5

Herbicidal activity when used post-emergence in a greenhouse

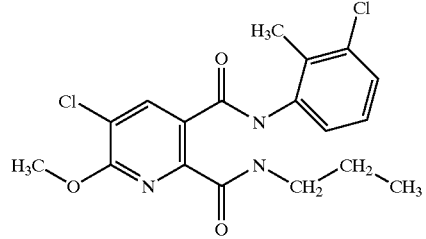

| | Application rate (kg of a.s./ha) | |
| --- | --- | --- |
| Test plants | 0.0625 | 0.0313 |
| AMARE | 100 | 98 |
| ALOMY | 85 | 75 |
| IPOSS | 100 | 98 |
| SOLNI | 100 | 100 |

TABLE 6

Herbicidal activity when used post-emergence in a greenhouse

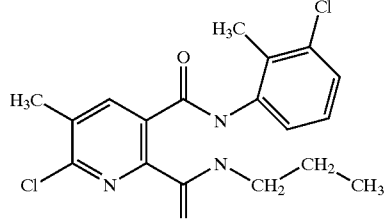

| | Application rate (kg of a.s./ha) |
| --- | --- |
| Test plants | 0.5 |
| ECHCG | 100 |
| GALAP | 100 |
| IPOSS | 100 |
| VIOAR | 100 |

TABLE 7

Herbicidal activity when used post-emergence in a greenhouse. Comparison of a compound according to the invention with the compound No. 100 from EP 799 825.

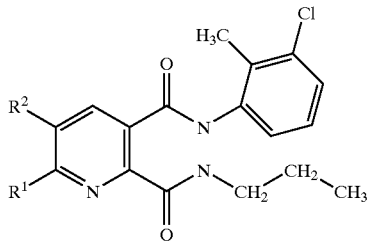

| | Invention | EP 799 825 |
|---|---|---|
| $R^1$ | Cl | $CH_3$ |
| $R^2$ | $CH_3$ | H |

| | Invention | Compound No. 100 from EP 799 825 |
|---|---|---|
| | Application rate (kg of a.s./ha) | |
| Test plants | 0.0313    0.0156 | 0.0313    0.0156 |
| GLXMA | 20    20 | 75    70 |
| AMARE | 90    75 | 85    70 |
| CHEAL | 90    85 | 95    90 |
| VERSS | 95    80 | 90    90 |

We claim:

1. A pyridine-2,3-dicarboxamide of the formula I

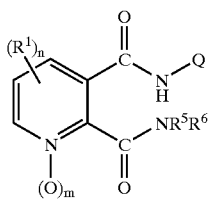

where:

$R^1$ is halogen, CN, $NO_2$, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, $C_1$–$C_3$-haloalkylthio, $C_1$–$C_3$-alkylsulfinyl, $C_1$–$C_3$-haloalkylsulfinyl, $C_1$–$C_3$-alkylsulfonyl, $C_1$–$C_3$-haloalkylsulfonyl, $C_3$–$C_6$-cycloalkyl, $C_3$–$C_6$-cycloalkyl-$C_1$–$C_3$-alkyl, $C_2$–$C_4$-alkenyl, $C_2$–$C_4$-haloalkenyl, $C_2$–$C_4$-alkynyl, $C_3$–$C_4$-haloalkynyl, amino, $C_1$–$C_3$-monoalkylamino or $C_1$–$C_3$-alkylcarbonyl;

Q is 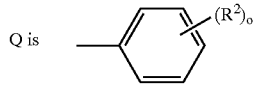

o is 2 or 3;

$R^2$ is selected from CN, $C_1$–$C_3$-alkylcarbonyl, $C_1$–$C_3$-alkylcarbamoyl, carbamoyl, $C_1$–$C_3$-alkoxycarbonyl, $C_1$–$C_3$-alkoximinomethyl, $C_1$–$C_3$-alkoxymethyl, formyl, $C_1$–$C_3$-alkyl, difluormethoxy and halogen, provided that one radical, which is selected from CN, $C_1$–$C_3$-alkylcarbonyl, carbamoyl, $C_1$–$C_3$-alkoxycarbonyl, $C_1$–$C_3$-alkoximinomethyl, $C_1$–$C_3$-alkoxymethyl and formyl, is located in the 2-position or in the 6-position, and at least one further radical is located in the 2-position, in the 3-position and/or in the 6-position;

$R^5$ is hydrogen, $C_1$–$C_3$-alkyl, OH or $C_1$–$C_4$-alkoxy;

$R^6$ is hydrogen, $C_1$–$C_6$-alkyl, $C_1$–$C_6$-haloalkyl, $C_1$–$C_6$-cyanoalkyl, $C_3$–$C_6$-cycloalkyl, $C_3$–$C_6$-cycloalkenyl, $C_3$–$C_6$-cycloalkyl-$C_1$–$C_3$-alkyl, $C_3$–$C_6$-cycloalkyl having 1 or 2 substituents which are selected independently of one another from the group consisting of halogen and $C_1$–$C_3$-alkyl, is $C_3$–$C_6$-cycloalkoxy-$C_1$–$C_3$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkoxycarbonyl-$C_1$–$C_6$-alkyl, $C_3$–$C_6$-alkenyl, $C_3$–$C_6$-alkynyl, amino, $C_1$–$C_4$-monoalkylamino, di-$C_1$–$C_4$-alkylamino or $R^6$ together with $R^5$ is a 5- or 6-membered heterocycle having 1, 2 or 3 heteroatoms which are selected independently of one another from the group consisting of N, O and S, and which is unsubstituted or has 1 or 2 substituents selected independently of one another from the group consisting of halogen, $C_1$–$C_3$-alkyl, $C_1$–$C_3$-alkoxy and $C_1$–$C_3$-haloalkyl;

m is 0 or 1;

n is 0, 1, 2 or 3;

and salts thereof.

2. A compound of the formula I as claimed in claim 1 where the further radical $R^2$ is selected from $C_1$–$C_3$-alkyl and halogen.

3. A compound of the formula I as claimed in claim 1 where n is 1 or 2 and $R^1$ is selected from the group consisting of $C_1$–$C_3$-alkyl, halogen and $C_1$–$C_3$-alkoxy.

4. A compound of the formula I as claimed in claim 1 where:

o is 2 and one radical $R^2$ is CN, $C_1$–$C_3$-alkylcarbonyl, carbamoyl, $C_1$–$C_3$-alkoxycarbonyl, $C_1$–$C_3$-alkoximinomethyl, $C_1$–$C_3$-alkoxymethyl or formyl, which is located in the 2-position and the other radical is $C_1$–$C_3$-alkyl, difluormethoxy or halogen, which is located in the 3-position.

5. A compound of the formula I as claimed in claim 4 where:

$(R^2)_o$ is selected from the group of substituent combinations, comprising:
2-cyano-3-halogen, 2-cyano-3-$C_1$–$C_3$-alkyl,
2-cyano-3-difluoromethoxy,
2-[$C_1$–$C_3$-alkoxycarbonyl]-3-halo,
2-($C_1$–$C_3$-alkoxycarbonyl)-3-$C_1$–$C_3$-alkyl,
2-methoximinomethyl-3-halo and
2-methoxymethyl-3-halo.

6. A compound of the formula I as claimed in claim 1 where:

n is 1 or 2 o is 3 and one of the radicals $R^2$ is $C_1$–$C_3$-alkoxycarbonyl, $C_1$–$C_3$-alkoxymethyl, $C_1$–$C_3$-alkylcarbamoyl, carbamoyl or cyano, which is located in the 2-position, and the two other radicals $R^2$ are halogen and/or $C_1$–$C_3$-alkyl in the 3- and/or 6-position or one of the radicals $R^2$ is $C_1$–$C_3$-alkoxycarbonyl, $C_1$–$C_3$-alkoxymethyl, $C_1$–$C_3$-alkylcarbamoyl, carbamoyl or cyano, which is located in the 6-position and the two other radicals $R^2$ are $C_1$–$C_3$-alkyl and/or halogen in the 2- and/or 3-position.

7. A compound of the formula I as claimed in claim 6, where:

n=1, o=3, one of the radicals $R^2$ is $C_1$–$C_3$-alkoxycarbonyl, $C_1$–$C_3$-alkoxymethyl, $C_1$–$C_3$-alkylcarbamoyl, carbamoyl or cyano in the 2-position, the two other radicals R2 are halogen and/or $C_1$–$C_3$-alkyl in the 3- and 6-position.

8. A compound of the formula I as claimed in claim 6, where:

n=1, o=3, one of the radicals $R^2$ is $C_1$–$C_3$-alkoxycarbonyl, $C_1$–$C_3$-alkoxymethyl, $C_1$–$C_3$-alkylcarbamoyl, carbamoyl or cyano in the 6-position, the two other radicals $R^2$ are halogen and/or $C_1$–$C_3$-alkyl in the 2- and 3-position.

9. A compound of the formula I as claimed in claim 6 where:

$(R^2)_o$ is selected from the substituent combinations, comprising:
2-($C_1$–$C_3$-alkyl)-3-halo-6-($C_1$–$C_3$-alkylcarbamoyl),
2-($C_1$–$C_3$-alkoxycarbonyl)-3,6-di-($C_1$–$C_3$-alkyl),
2-cyano-3-halo-6-($C_1$–$C_3$-alkyl),
2-($C_1$–$C_3$-alkoxycarbonyl)-3-halo-6-($C_1$–$C_3$-alkyl),
2-($C_1$–$C_3$-alkoxycarbonyl)-3,6-dihalo,
2-cyano-3-($C_1$–$C_3$-alkyl)-6-halo,
2-($C_1$–$C_3$-alkoxycarbonyl)-3-($C_1$–$C_3$-alkyl)-6-halo,
2-($C_1$–$C_3$-alkyl)-3-halo-6-($C_1$–$C_3$-alkoxycarbonyl),
2-cyano-3,6-dihalo, 2-cyano-3,6-($C_1$–$C_3$-alkyl)$_2$,
2-methyl-3-chloro-6-cyano, 2-chloro-3-methyl-6-cyano,
2-ethyl-3-chloro-6-cyano, 2-chloro-3-ethyl-6-cyano,
2-cyano-3-chloro-6-($C_1$–$C_3$-alkoxycarbonyl),
2-(carbamoyl)-3-halo-6-($C_1$–$C_3$-alkyl),
2-halo-3-($C_1$–$C_3$-alkyl)-6-($C_1$–$C_3$-alkoxycarbonyl),
2,3-dihalo-6-($C_1$–$C_3$-alkoxycarbonyl),
2,3-dihalo-6-cyano, 2,3-($C_1$–$C_3$-alkyl)$_2$-6-cyano,
2,6-($C_1$–$C_3$-alkoxycarbonyl)$_2$-3-halo,
2-($C_1$–$C_3$-alkoxycarbonyl)-3-halo-6-($C_1$–$C_3$-alkoxy),
2-cyano-3-halo-6-($C_1$–$C_3$-alkoxy),
2-methoxymethyl-3-halo-6-($C_1$–$C_3$-alkyl),
2-($C_1$–$C_3$-alkyl)-3-halo-6-methoxymethyl and
2-($C_1$–$C_3$-alkoxycarbonyl)-3-halo-6-cyano.

10. A compound of the formula I as claimed in claim 1 where:

$R^1$ is $C_1$–$C_3$-alkyl, halogen, $NO_2$, amino, mono-$C_1$–$C_3$-alkylamino, $C_1$–$C_3$-alkoxy or CN;
$R^5$ is hydrogen;
$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;
m is 0;
n is 1 or 2;
and salts thereof.

11. A compound of the formula I as claimed in claim 1 where:

$R^1$ is $C_1$–$C_3$-alkyl, halogen, or $C_1$–$C_3$-alkoxy;
$R^5$ is hydrogen;
$R^6$ is hydrogen, $C_1$–$C_6$-alkyl, $C_1$–$C_6$-haloalkyl, $C_3$–$C_6$-alkenyl, $C_3$–$C_6$-cycloalkyl or $C_3$–$C_6$-cycloalkyl-$C_1$–$C_3$-alkyl;
m is 0;
n is 1 or 2;
and salts thereof.

12. A compound of the formula I as claimed in claim 4,
3-[(3-Chloro-2-methoxycarbonyl)phenyl]aminocarbonyl-6-methylpyridine-2-carboxylic acid N-n-propylamide,
3-[(3-chloro-2-methoxycarbonyl)phenyl]aminocarbonyl-6-methylpyridine-2-carboxylic acid N-isopropylamide,
3-[(3-chloro-2-methoxycarbonyl)phenyl]aminocarbonyl-6-methylpyridine-2-carboxylic acid N-n-butylamide,
3-[(3-chloro-2-methoxycarbonyl)phenyl]aminocarbonyl-6-methylpyridine-2-carboxylic acid N-isobutylamide,
3-[(3-chloro-2-methoxycarbonyl)phenyl]aminocarbonyl-6-methylpyridine-2-carboxylic acid N-sec-butylamide,
3-[(3-chloro-2-methoxycarbonyl)phenyl]aminocarbonyl-6-methylpyridine-2-carboxylic acid N-[(cyclopropyl)methyl]-amide.

13. A compound of the formula I as claimed in claim 6,
3-[(3-Chloro-2-methoxycarbonyl-6-methyl)phenyl aminocarbonyl-6-methylpyridine-2-carboxylic acid N-n-propylamide,
3-[(3-chloro-2-methoxycarbonyl-6-methyl)phenyl] aminocarbonyl-6-methylpyridine-2-carboxylic acid N-isopropylamide,
3-[(3-chloro-2-methoxycarbonyl-6-methyl)phenyl] aminocarbonyl-6-methylpyridine-2-carboxylic acid N-n-butylamide,
3-[(3-chloro-2-methoxycarbonyl-6-methyl)phenyl] aminocarbonyl-6-methylpyridine-2-carboxylic acid N-isobutylamide,
3-[(3-chloro-2-methoxycarbonyl-6-methyl)phenyl] aminocarbonyl-6-methylpyridine-2-carboxylic acid N-sec-butylamide,
3-[(3-chloro-2-methoxycarbonyl-6-methyl)phenyl] aminocarbonyl-6-methylpyridine-2-carboxylic acid N-[(cyclopropyl)methyl]amide,
3-[(3-chloro-2-methoxycarbonyl-6-methyl)phenyl] aminocarbonyl-6-methylpyridine-2-carboxylic acid N-(3-chloropropyl)amide,
3-[(3-chloro-6-ethyl-2-methoxycarbonyl)phenyl] aminocarbonyl-6-methylpyridine-2-carboxylic acid N-n-propylamide,
3-((3-chloro-6-ethyl-2-methoxycarbonyl)phenyl] aminocarbonyl-6-methylpyridine-2-carboxylic acid N-isopropylamide,
3-[(3-chloro-6-ethyl-2-methoxycarbonyl)phenyl] aminocarbonyl-6-methylpyridine-2-carboxylic acid N-n-butylamide,
3-[(3-chloro-6-ethyl-2-methoxycarbonyl)phenyl] aminocarbonyl-6-methylpyridine-2-carboxylic acid N-isobutylamide,
3-[(3-chloro-6-ethyl-2-methoxycarbonyl)phenyl] aminocarbonyl-6-methylpyridine-2-carboxylic acid N-sec-butylamide,
3-[(3-chloro-6-ethyl-2-methoxycarbonyl)phenyl] aminocarbonyl-6-methylpyridine-2-carboxylic acid N-[(cyclopropyl)methyl]amide,
3-[(3-chloro-6-ethyl-2-methoxycarbonyl)phenyl] aminocarbonyl-6-methylpyridine-2-carboxylic acid N-(3-chloropropyl)amide,
3-[(3-bromo-2-methoxycarbonyl-6-methyl)phenyl] aminocarbonyl-6-methylpyridine-2-carboxylic acid N-n-propylamide,
3-[(3-bromo-2-methoxycarbonyl-6-methyl)phenyl] aminocarbonyl-6-methylpyridine-2-carboxylic acid N-isopropylamide,
3-[(3-bromo-2-methoxycarbonyl-6-methyl)phenyl] aminocarbonyl-6-methylpyridine-2-carboxylic acid N-n-butylamide,
3-[(3-bromo-2-methoxycarbonyl-6-methyl)phenyl] aminocarbonyl-6-methylpyridine-2-carboxylic acid N-isobutylamide,
3-[(3-bromo-2-methoxycarbonyl-6-methyl)phenyl] aminocarbonyl-6-methylpyridine-2-carboxylic acid N-sec-butylamide, 3-[(3-bromo-2-methoxycarbonyl-6-methyl)phenyl] aminocarbonyl-6-methylpyridine-2-carboxylic acid N-[(cyclopropyl)methyl]amide, 3-[(3-bromo-2-methoxycarbonyl-6-methyl)phenyl] aminocarbonyl-6-methylpyridine-2-carboxylic acid N-(3-chloropropyl)amide, 3-[(3-bromo-6-ethyl-2-methoxycarbonyl)phenyl] aminocarbonyl-6-methylpyridine-2-carboxylic acid N-n-propylamide, 3-[(3-bromo-6-ethyl-2-methoxycarbonyl)phenyl] aminocarbonyl-6-methylpyridine-2-carboxylic acid N-isopropylamide, 3-[(3-bromo-6-ethyl-2-methoxycarbonyl)phenyl] aminocarbonyl-6-methylpyridine-2-carboxylic acid N-n-butylamide, 3-[(3-bromo-6-ethyl-2-methoxycarbonyl)phenyl] aminocarbonyl-6-methylpyridine-2-carboxylic acid N-isobutylamide, 3-[(3-bromo-6-ethyl-2-methoxycarbonyl)phenyl] aminocarbonyl-6-methylpyridine-2-carboxylic acid N-sec-butylamide, 3-[(3-bromo-6-ethyl-2-methoxycarbonyl)phenyl] aminocarbonyl-6-methylpyridine-2-carboxylic acid N-[(cyclopropyl)methyl]amide, 3-[(3-bromo-6-ethyl-2-methoxycarbonyl)phenyl] aminocarbonyl-6-methylpyridine-2-carboxylic acid N-(3-chloropropyl)amide, 3-[(3-chloro-2-methoxymethyl-6-methyl)phenyl] aminocarbonyl-6-methylpyridine-2-carboxylic acid N-n-propylamide, 3-[(3-chloro-2-methoxymethyl-6-methyl)phenyl] aminocarbonyl-6-methylpyridine-2-carboxylic acid N-isopropylamide, 3-[(3-chloro-2-methoxymethyl-6-methyl)phenyl] aminocarbonyl-6-methylpyridine-2-carboxylic acid N-n-butylamide, 3-[(3-chloro-2-methoxymethyl-6-methyl)phenyl] aminocarbonyl-6-methylpyridine-2-carboxylic acid N-isobutylamide, 3-[(3-chloro-2-methoxymethyl-6-methyl)phenyl] aminocarbonyl-6-methylpyridine-2-carboxylic acid N-sec-butylamide, 3-[(3-chloro-2-methoxymethyl-6-methyl)phenyl] aminocarbonyl-6-methylpyridine-2-carboxylic acid N-[(cyclopropyl)methyl]amide, 3-[(3-chloro-2-methoxymethyl-6-methyl)phenyl] aminocarbonyl-6-methylpyridine-2-carboxylic acid N-(3-chloropropyl)amide, 3-[(3-chloro-6-ethyl-2-methoxymethyl)phenyl] aminocarbonyl-6-methylpyridine-2-carboxylic acid N-n-propylamide, 3-[(3-chloro-6-ethyl-2-methoxymethyl)phenyl] aminocarbonyl-6-methylpyridine-2-carboxylic acid N-isopropylamide, 3-[(3-chloro-6-ethyl-2-methoxymethyl)phenyl] aminocarbonyl-6-methylpyridine-2-carboxylic acid N-n-butylamide, 3-[(3-chloro-6-ethyl-2-methoxymethyl)phenyl] aminocarbonyl-6-methylpyridine-2-carboxylic acid N-isobutylamide, 3-[(3-chloro-6-ethyl-2-methoxymethyl)phenyl] aminocarbonyl-6-methylpyridine-2-carboxylic acid N-sec-butylamide,=

3-[(3-chloro-6-ethyl-2-methoxymethyl)phenyl] aminocarbonyl-6-methylpyridine-2-carboxylic acid N-[(cyclopropyl)methyl]amide, 3-[(3-chloro-6-ethyl-2-methoxymethyl)phenyl] aminocarbonyl-6-methylpyridine-2-carboxylic acid N-(3-chloropropyl)amide, 3-[(3-bromo-2-methoxymethyl-6-methyl)phenyl] aminocarbonyl-6-methylpyridine-2-carboxylic acid n-propylamide, 3-[(3-bromo-2-methoxymethyl-6-methyl)phenyl] aminocarbonyl-6-methylpyridine-2-carboxylic acid N-isopropylamide, 3-[(3-bromo-2-methoxymethyl-6-methyl)phenyl] aminocarbonyl-6-methylpyridine-2-carboxylic acid N-n-butylamide, 3-[(3-bromo-2-methoxymethyl-6-methyl)phenyl] aminocarbonyl-6-methylpyridine-2-carboxylic acid N-isobutylamide, 3-[(3-bromo-2-methoxymethyl-6-methyl)phenyl] aminocarbonyl-6-methylpyridine-2-carboxylic acid N-sec-butylamide, 3-[(3-bromo-2-methoxymethyl-6-methyl)phenyl] aminocarbonyl-6-methylpyridine-2-carboxylic acid N-[(cyclopropyl)methyl]amide, 3-[(3-bromo-2-methoxymethyl-6-methyl)phenyl] aminocarbonyl-6-methylpyridine-2-carboxylic acid N-(3-chloropropyl)amide.

14. A compound of the formula I as claimed in claim 6,

3-[(3-Chloro-2-methyl-6-methoxymethyl)phenyl] aminocarbonyl-6-methylpyridine-2-carboxylic acid N-n-propylamide, 3-[(3-chloro-2-methyl-6-methoxymethyl)phenyl] aminocarbonyl-6-methylpyridine-2-carboxylic acid N-isopropylamide, 3-[(3-chloro-2-methyl-6-methoxymethyl)phenyl] aminocarbonyl-6-methylpyridine-2-carboxylic acid N-n-butylamide, 3-[(3-chloro-2-methyl-6-methoxymethyl)phenyl] aminocarbonyl-6-methylpyridine-2-carboxylic acid N-isobutylamide, 3-[(3-chloro-2-methyl-6-methoxymethyl)phenyl] aminocarbonyl-6-methylpyridine-2-carboxylic acid N-sec-butylamide, 3-[(3-chloro-2-methyl-6-methoxymethyl)phenyl] aminocarbonyl-6-methylpyridine-2-carboxylic acid N-[(cyclopropyl)methyl]amide, 3-[(3-chloro-2-methyl-6-methoxymethyl)phenyl] aminocarbonyl-6-methylpyridine-2-carboxylic acid N-(3-chloropropyl)amide, 3-[(3-chloro-2-ethyl-6-methoxymethyl)phenyl] aminocarbonyl-6-methylpyridine-2-carboxylic acid N-n-propylamide, 3-[(3-chloro-2-ethyl-6-methoxymethyl)phenyl] aminocarbonyl-6-methylpyridine-2-carboxylic acid N-isopropylamide, 3-[(3-chloro-2-ethyl-6-methoxymethyl)phenyl] aminocarbonyl-6-methylpyridine-2-carboxylic acid N-n-butylamide, 3-[(3-chloro-2-ethyl-6-methoxymethyl)phenyl] aminocarbonyl-6-methylpyridine-2-carboxylic acid N-isobutylamide, 3-[(3-chloro-2-ethyl-6-methoxymethyl)phenyl] aminocarbonyl-6-methylpyridine-2-carboxylic acid N-sec-butylamide, 3-[(3-chloro-2-ethyl-6-methoxymethyl)phenyl] aminocarbonyl-6-methylpyridine-2-carboxylic acid N-[(cyclopropyl)methyl]amide, 3-[(3-chloro-2-ethyl-6-methoxymethyl)phenyl] aminocarbonyl-6-methylpyridine-2-carboxylic acid N-(3-chloropropyl)amide, 3-[(3-bromo-2-ethyl-6-methoxymethyl)phenyl] aminocarbonyl-6-methylpyridine-2-carboxylic acid N-n-propylamide, 3-[(3-bromo-2-ethyl-6-methoxymethyl)phenyl]
aminocarbonyl-6-methylpyridine-2-carboxylic acid
N-isopropylamide,
3-[(3-bromo-2-ethyl-6-methoxymethyl)phenyl]
aminocarbonyl-6-methylpyridine-2-carboxylic acid N-n-
butylamide,
3-[(3-bromo-2-ethyl-6-methoxymethyl)phenyl]
aminocarbonyl-6-methylpyridine-2-carboxylic acid
N-isobutylamide,
3-[(3-bromo-2-ethyl-6-methoxymethyl)phenyl]
aminocarbonyl-6-methylpyridine-2-carboxylic acid
N-sec-butylamide,
3-[(3-bromo-2-ethyl-6-methoxymethyl)phenyl]
aminocarbonyl-6-methylpyridine-2-carboxylic acid
N-[(cyclopropyl)methyl]amide,
3-[(3-bromo-2-ethyl-6-methoxymethyl)phenyl]
aminocarbonyl-6-methylpyridine-2-carboxylic acid N-(3-
chloropropyl)amide.

15. A compound of the formula I as claimed in claim 1,
3-[(3-Chloro-2-cyano-6-methoxymethyl)phenyl]
aminocarbonyl-6-methylpyridine-2-carboxylic acid N-n-
propylamide,
3-[(3-chloro-2-cyano-6-methoxymethyl)phenyl]
aminocarbonyl-6-methylpyridine-2-carboxylic acid
N-isopropylamide,
3-[(3-chloro-2-cyano-6-methoxymethyl)phenyl]
aminocarbonyl-6-methylpyridine-2-carboxylic acid N-n-
butylamide,
3-[(3-chloro-2-cyano-6-methoxymethyl)phenyl]
aminocarbonyl-6-methylpyridine-2-carboxylic acid
N-isobutylamide,
3-[(3-chloro-2-cyano-6-methoxymethyl)phenyl]
aminocarbonyl-6-methylpyridine-2-carboxylic acid
N-sec-butylamide,
3-[(3-chloro-2-cyano-6-methoxymethyl)phenyl]
aminocarbonyl-6-methylpyridine-2-carboxylic acid
N-[(cyclopropyl)methyl]amide,
3-[(3-chloro-2-cyano-6-methoxymethyl)phenyl]
aminocarbonyl-6-methylpyridine-2-carboxylic acid N-(3-
chloropropyl)amide,
3-[(3-bromo-2-cyano-6-methoxymethyl)phenyl]
aminocarbonyl-6-methylpyridine-2-carboxylic acid N-n-
propylamide,
3-[(3-bromo-2-cyano-6-methoxymethyl)phenyl]
aminocarbonyl-6-methylpyridine-2-carboxylic, acid
N-isopropylamide,
3-[(3-bromo-2-cyano-6-methoxymethyl)phenyl]
aminocarbonyl-6-methylpyridine-2-carboxylic acid N-n-
butylamide,
3-[(3-bromo-2-cyano-6-methoxymethyl)phenyl]
aminocarbonyl-6-methylpyridine-2-carboxylic acid
N-isobutylamide,
3-[(3-bromo-2-cyano-6-methoxymethyl)phenyl]
aminocarbonyl-6-methylpyridine-2-carboxylic acid
N-sec-butylamide,
3-[(3-bromo-2-cyano-6-methoxymethyl)phenyl]
aminocarbonyl-6-methylpyridine-2-carboxylic acid
N-[(cyclopropyl)methyl]amide,
3-[(3-bromo-2-cyano-6-methoxymethyl)phenyl]
aminocarbonyl-6-methylpyridine-2-carboxylic acid N-(3-
chloropropyl)amide.

16. A compound as claimed in claim 1,
N-cyclopropylmethyl-3-[(2-cyano-3-chlorophenyl)
aminocarbonyl]-6-methylpyridine-2-carboxamide,
N-n-propyl-3-[(3-chloro-2-methoxycarbonyl)phenyl]
aminocarbonyl-6-methylpyridine-2-carboxamide,
N-n-propyl-3-[(3-methyl-2-methoxycarbonyl)phenyl]
aminocarbonyl-6-methylpyridine-2-carboxamide,
N-n-propyl-3-[(3,6-dimethyl-2-methoxycarbonyl)phenyl]
aminocarbonyl-6-methylpyridine-2-carboxamide,
N-cyclopropylmethyl-3-[(3,6-dimethyl-2-
methoxycarbonyl)phenyl]aminocarbonyl-6-
methylpyridine-2-carboxamide,
N-cyclopropylmethyl-3-[(3-methyl-2-methoxycarbonyl)
phenyl]aminocarbonyl-6-methylpyridine-2-carboxamide,
N-n-propyl-3-[(2-cyano-3-chloro-6-methyl)phenyl]
aminocarbonyl-6-methylpyridine-2-carboxamide,
N-cyclopropylmethyl-3-[(3-chloro-2-methoxyiminomethyl)
phenyl]aminocarbonyl-6-methylpyridine-2-carboxamide,
N-n-propyl-3-[(3-bromo-2-methoxycarbonyl)phenyl]
aminocarbonyl-6-methylpyridine-2-carboxamide,
N-n-propyl-3-[(3-chloro-2-methyl-6-methoxycarbonyl)
phenyl]aminocarbonyl-6-methylpyridine-2-carboxamide,
N-cyclopropylmethyl-3-[(3-chloro-2-methyl-6-
methoxycarbonyl)phenyl]aminocarbonyl-6-
methylpyridine-2-carboxamide,
N-n-propyl-3-[(3-chloro-2-methoxycarbonyl-6-methyl-)
phenyl]aminocarbonyl-6-methylpyridine-2-carboxamide,
N-cyclopropylmethyl-3-[(3,6-dichloro-2-methoxycarbonyl)
phenyl]aminocarbonyl-6-methylpyridine-2-carboxamide,
N-n-propyl-3-[(6-chloro-2-methoxycarbonyl-3-methyl)
phenyl]aminocarbonyl-6-methylpyridine-2-carboxamide,
N-cyclopropylmethyl-3-[(3-chloro-6-methoxycarbonyl-2-
methyl)phenyl]aminocarbonyl-6-methylpyridine-2-
carboxamide,
N-n-propyl-3[(3-chloro-6-ethyl-2-methoxycarbonyl)
phenyl]aminocarbonyl-6-methylpyridine-2-carboxamide,
N-cyclopropylmethyl-3[(2-cyano-3,6-dimethyl)phenyl]
aminocarbonyl-6-methylpyridine-2-carboxamide,
N-n-propyl-3[(3-bromo-2-methoxycarbonyl-6-methyl)
phenyl]aminocarbonyl-6-methylpyridine-2-carboxamide,
N-cyclopropylmethyl-3[(3-bromo-2-methoxycarbonyl-6-
ethyl)phenyl]aminocarbonyl-6-methylpyridine-2-
carboxamide,
N-n-propyl-[(3-chloro-2-ethyl-6-methoxycarbonyl)phenyl]
aminocarbonyl-6-methylpyridine-2-carboxamide,
N-cyclopropylmethyl-[(3-chloro-6-cyano-2-methyl)phenyl]
aminocarbonyl-6-methylpyridine-2-carboxamide,
N-n-propyl-[(3-chloro-6-methoxy-2-methoxycarbonyl)
phenyl]aminocarbonyl-6-methylpyridine-2-carboxamide,
N-n-propyl-3-[(3-chloro-2-cyano-6-methoxy)phenyl]
aminocarbonyl-6-methylpyridine-2-carboxamide,
N-cyclopropylmethyl-3-( (3-chloro-2-methoxymethyl-6-
methyl) phenyl aminocarbonyl-6-methylpyridine-2-
carboxamide,
N-n-propyl-3-[(3-chloro-6-ethyl-2-methoxymethyl)phenyl]
aminocarbonyl-6-methylpyridine-2-carboxamide,
N-cyclopropylmethyl-3-[(3-chloro-6-methoxymethyl-2-
methyl)phenyl]aminocarbonyl-6-methylpyridine-2-
carboxamide,
N-n-propyl-3-[(3-chloro-6-cyano-2-methoxycarbonyl)
phenyl]aminocarbonyl-6-methylpyridine-2-carboxamide,
N-cyclopropylmethyl-3-[(3-chloro-2-cyano-6-
methoxycarbonyl)phenyl]aminocarbonyl-6-
methylpyridine-2-carboxamide.

17. A herbicidal composition, comprising a herbicidally effective amount of at least one pyridine-2,3-dicarboxamide as claimed in claim 1 or an agriculturally useful salt thereof and at least one inert liquid and/or solid carrier and also, if desired, at least one adjuvant.

18. A composition for the desiccation and/or defoliation of plants, comprising an amount of at least one pyridine-2,3-dicarboxamide as claimed in claim 1 or an agriculturally useful salt thereof, which acts as a desiccant and/or defoliant, and at least one inert liquid and/or solid carrier and, if desired, at least one adjuvant.

19. A method for controlling undesirable vegetation, which comprises applying a herbicidally effective amount of at least one pyridine-2,3-dicarboxamide as claimed in claim 1 or an agriculturally useful salt thereof onto plants, their habitat or on seed and allowing it to act thereon.

20. A method for the desiccation and/or defolation of plants, which comprises applying an amount of at least one pyridine-2,3-dicarboxamide as claimed in in claim 1 or an agriculturally useful salt thereof, which acts as a desiccant and/or defoliant, onto plants and allowing it to act thereon.

* * * * *